(12) United States Patent
Cohen et al.

(10) Patent No.: US 7,927,591 B2
(45) Date of Patent: Apr. 19, 2011

(54) CONFORMATION SPECIFIC ANTIBODIES

(75) Inventors: Edward H. Cohen, Belmont, MA (US); Isaac J. Rondon, San Francisco, CA (US); Timothy A. Springer, Newton, MA (US); Motomu Shimaoka, Brookline, MA (US)

(73) Assignee: The CBR Institute for Biomedical Research, Inc., Boston, MA (US)

( * ) Notice: Subject to any disclaimer, the term of this patent is extended or adjusted under 35 U.S.C. 154(b) by 516 days.

(21) Appl. No.: 10/589,956

(22) PCT Filed: Feb. 22, 2005

(86) PCT No.: PCT/US2005/005361
§ 371 (c)(1),
(2), (4) Date: Sep. 20, 2007

(87) PCT Pub. No.: WO2005/079515
PCT Pub. Date: Sep. 1, 2005

(65) Prior Publication Data
US 2008/0069777 A1 Mar. 20, 2008

Related U.S. Application Data

(60) Provisional application No. 60/546,354, filed on Feb. 19, 2004.

(51) Int. Cl.
*A61K 39/395* (2006.01)
*C07K 16/46* (2006.01)
*C07K 16/28* (2006.01)

(52) U.S. Cl. .......... 424/133.1; 424/143.1; 530/387.3; 530/388.22; 530/388.7

(58) Field of Classification Search .......... None
See application file for complete search history.

(56) References Cited

U.S. PATENT DOCUMENTS 5,859,205 A * 1/1999 Adair et al. ............. 530/387.3
2002/0123614 A1 * 9/2002 Springer et al. ............. 530/350

FOREIGN PATENT DOCUMENTS
WO  WO 98/23761  * 10/1997

OTHER PUBLICATIONS

Klimka et al.,Human anti-CD30 recombinant antibodies by guided phage antibody selection using cell panning. British Journal of Cancer (2000) 83:252-260.*
Beiboer et al.,Guided selection of a pan carcinoma specific antibody reveals similar binding characteristics yet structural divergence between the original murine antibody and its human equivalent. J. Mol., Biol. (2000) 296:833-849).*
Brown et al. Tolerance of single, but not multiple, amino acid replacements in antibody VH CDR 2: a means of minimizing B cell wastage from somatic hypermutation? J. Immuno. May 1996, 3285-91.*
Vajdos et al. Comprehensive functional maps of the antigen-binding site of an anti-ErbB2 antibody obtained with shotgun scanning mutagenesis. J. Mol. Biol. 2002, Jul. 5, 320(2):415-28 at 416.*
Eduardo Padlan, Anatomy of the antibody molecule. Mol Immunol. Feb. 1994;31(3):169-217.*
Portolano et al., Lack of promiscuity in autoantigen-specific H and L chain combinations as revealed by human H and L chain "roulette". J Immunol. Feb. 1, 1993;150(3):880-7.*
Paul, Fundamental Immunology, 3rd Edition, 1993, pp. 292-295.*
Rudikoff et al. Single amino acid substitution altering antigen-binding specificity. Proc. Natl. Acad. Sci. USA, 79(6):1979-1983, Mar. 1982.*
MacCallum et al. Antibody-antigen interactions: contact analysis and binding site topography. J. Mol. Biol., 262, 732-745, 1996.*
Casset et al. A peptide mimetic of an anti-CD4 monoclonal antibody by rational design. Biochemical and Biophysical Research Communications, 307:198-205, 2003.*

* cited by examiner

*Primary Examiner* — Maher M Haddad
(74) *Attorney, Agent, or Firm* — Rissman Hendricks & Oliverio LLP

(57) ABSTRACT

The disclosure provides, inter alia, binding proteins (e.g., antibodies) that bind to an integrin in an activated conformation, e.g., activated LFA-1 ("aLFA-1"), e.g., relative to a non-activated conformation of LFA-1. In one embodiment, the binding proteins inhibit at least one function of an aLFA-1, e.g., inhibit a binding interaction between aLFA-1 and a cognate ligand of aLFA-1, e.g., an ICAM protein. The binding proteins can be used to treat or prevent an inflammatory disorder or other disorder.

14 Claims, 1 Drawing Sheet

US 7,927,591 B2

CONFORMATION SPECIFIC ANTIBODIES

CROSS-REFERENCE TO RELATED APPLICATIONS

This application claims priority to U.S. Application Ser. No. 60/546,354, filed on Feb. 19, 2004, the contents of which are hereby incorporated by reference.

BACKGROUND

Integrins are cell surface molecules that mediate important interactions between cells and between cells and the extracellular milieu. Integrins can adopt at least two different conformations on cell surfaces: a non-activated conformation that does not bind to the integrin ligand and an activated conformation that can bind the integrin ligand. Cellular signalling can cause integrins to alter their conformation from a non-activated conformation to an activated conformation. After activation, integrins bind in a specific manner to their cognate ligands on the surface of other cells, in the extracellular matrix, or that are assembled in the clotting or complement cascades.

Each integrin includes an α subunit and a β subunit. Over twenty different integrin heterodimers are known. Many integrins are selectively expressed on particular cells in the body. For example, a subset of integrins are selectively expressed on leukocytes.

Integrins on leukocytes are of central importance in leukocyte emigration and in inflammatory and immune responses. Two exemplary integrins on leukocytes are LFA-1 and Mac-1. LFA-1 (αLβ2) binds to a number of cognate ligands, including inflammation-associated cell surface molecules (ICAM), e.g., ICAM-1, ICAM-2, ICAM-3, ICAM-4, and ICAM-5. Mac-1 (αMβ2) binds ICAM-1, the complement component iC3b, and the clotting component fibrinogen.

SUMMARY

Disclosed are binding proteins that interact with integrins ("integrin binding proteins"), particularly specific conformations of integrins. An exemplary integrin binding protein is an antibody. An integrin binding protein can preferentially interact with an activated conformation of an integrin, e.g., relative to a non-activated conformation, e.g., an inactive or resting conformation. An integrin binding protein can preferentially interact with a mimic of an activated conformation of an integrin (e.g., a modified integrin whose conformation is constrained in a state competent to bind to a cognate ligand), e.g., relative to a non-activated conformation, e.g., an inactive or resting conformation, or mimics thereof. The integrin binding protein can bind with at least 1.5, 2, 3, 4, 5, 10, 15, 20, 50, 70, 80, 100, 500, 1000, or $10^5$ fold greater affinity to the preferred conformation relative to the disfavored conformation.

In one embodiment, the integrin binding protein can be used to modulate integrin activity, e.g., antagonize an activity of an activated integrin. For example, the integrin binding protein can be used to inhibit interaction between a cell that has an activated integrin on its surface and a cognate ligand of the activated integrin.

In one embodiment, the integrin binding protein interacts with a leukocyte integrin, e.g., LFA-1, e.g., activated LFA-1 ("aLFA-1"), e.g., human aLFA-1.

In one embodiment, the integrin binding protein is an antibody. The antibody can include one or more human regions, e.g., one or more human CDRs, one or more human frameworks (e.g., germline or somatically mutated human FR), or one or more human constant regions, or effectively human regions of the same.

In one embodiment, the integrin binding protein inhibits aLFA-1 activity. For example, the integrin binding protein prevents aLFA-1 from interacting with a binding partner, e.g., a cognate ligand of LFA-1. In particular cases, the antibody can prevent aLFA-1 from interacting with an ICAM, e.g., ICAM-1, ICAM-2, ICAM-3, ICAM-4, or ICAM-5.

The integrin binding protein can modulate (e.g., decrease) inflammation, and accordingly can be used to treat an inflammatory disorder, e.g., rheumatoid arthritis or psoriasis. Accordingly, the integrin binding protein can be administered to a subject in an amount effective to treat or prevent such a disorder.

In one aspect, the disclosure features a protein that includes an immunoglobulin heavy chain (HC) variable domain sequence and an immunoglobulin light chain (LC) variable domain sequence. The HC variable domain sequence and the LC variable domain sequence form an antigen binding site that binds to an activated conformation of LFA-1 ("aLFA-1"), e.g., with cation dependence (e.g., that detectably binds at 10 μg/ml protein concentration). For example, maximal binding requires the presence of a cation. The protein can require magnesium or manganese for binding to LFA-1. Exemplary cation concentrations is between 0.01 and 11 mM, e.g., between 0.1 and 5 mM, or 0.1 and 3 mM. In one embodiment, the protein binds to LFA-1 in the presence of magnesium, EGTA and the CBRLFA-½ antibody, but not in the presence of magnesium, calcium, and the CBRLFA-½ antibody.

In one embodiment, the proteins binds to aLFA-1 with a better affinity than MHM24. For example, the protein binds with a $K_D$ that is less than the $K_D$ of MHM24, e.g., at least 0.1, 0.5, or 1 nM less than the $K_D$ of MHM24.

In one embodiment, the protein can bind to a K287C/K294C I-domain of αL. For example, the protein preferentially binds a K287C/K294C I-domain of αL relative to L161C/F299C I-domain of αL or wild-type αL.

In one embodiment, the protein binds aLFA-1 with a $K_D$ of less than $10^{-7}$, $10^{-8}$, $10^{-9}$, $10^{-10}$, $10^{-11}$, or $10^{-12}$ M. In some cases, the protein binds human aLFA-1 with a $k_{off}$ of less than 10, 5, 1, 0.5, 0.2, 0.1, or 0.05 $s^{-1}$. In one embodiment, the protein can reduce interaction between LFA-1 and a cognate ligand of LFA-1 (e.g., an ICAM, e.g., ICAM-1). In one embodiment, the protein can reduce interaction between a leukocyte and an ICAM-expressing cell, e.g., an endothelial cell.

In one embodiment, the H1 and H2 hypervariable loops of the HC variable domain sequence have the same canonical structure as an antibody described herein. For example, the heavy chain variable domain sequence forms a variable domain having the 1-3 Chothia canonical structure for the H1 and H2 hypervariable loops.

In one embodiment, the L1 and L2 hypervariable loops of the LC variable domain sequence have the same canonical structure as an antibody described herein. For example, the light chain variable domain sequence forms a variable domain having the 2-1 Chothia canonical structure for the L1 and L2 hypervariable loops.

In another aspect, the disclosure features a protein that includes an immunoglobulin heavy chain (HC) variable domain sequence and an immunoglobulin light chain (LC) variable domain sequence, wherein the HC variable domain sequence and the LC variable domain sequence form an antigen binding site that binds to an activated conformation of LFA-1, wherein the heavy chain variable domain sequence includes (a) a CDR1 that includes at least 3, 4, or 5 amino acids (of 5) from RYVMW (SEQ ID NO:1), (b) a CDR2 that includes at least 13, 14, 15, 16, or 17 amino acid (of 17) from YIWPSGGNTYYADSVKG (SEQ ID NO:2), and/or (c) a CDR3 that includes at least 5, 6, 7, 8, 9, 10, 11 amino acids (of 11) from SYDFWSNAFDI (SEQ ID NO:3) or another CDR3 described herein (e.g., from an affinity matured variant of D2-57). The protein can include other features described herein.

Exemplary sequences in the region of CDR3 of the heavy chain variable domain sequence can include Xa-S—X2-D-X4-X5-S—X7-A-X8-X9-X10-X11 (SEQ ID NO:4). X can be any amino acid, preferably any non-cysteine amino acid. The sequence can have one or more of the following properties:
  (i) Xa is hydrophilic, e.g., an uncharged hydrophilic residues such as S or N;
  (ii) X2 is aromatic, e.g., Y or F;
  (iii) X4 is hydrophobic (e.g., L or aromatic, e.g., Y or F);
  (iv) X5 is hydrophobic, e.g., a large hydrophobic side chain, e.g., W or R;
  (v) X7 is N or Y, or another amino with a side chain that includes a hydroxyl;
  (vi) X9 is aromatic, e.g., Y or F;
  (vii) X10 is a small residue, e.g., a polar residue such as D or E, or A; and
  (viii) X11 is any amino acid, e.g., K, I, S, M, N, V, or L.

The sequence can include S-(Y/F)-D-(L/Y/F)-(W/R/K)-S-(N/Q/Y)-A-(Y/F)-(D/E/A)-(K/I/S/M/N/V/L) (SEQ ID NO:5) or S-(Y/F)-D-(L/Y/F)-(W/R)-S-(N/Y)-A-(Y/F)-(D/E/A)-(K/I/S/M/N/V/L) (SEQ ID NO:6). Still another sequence can include:

Xa-(S/T)-X2-(D/E)-X4-X5-(S/T)-X7-(G/A/S)-X8-X9-X10-X11.

In one embodiment, the protein includes features of D2-57 or DX-2001, e.g., the CDR regions of the D2-57 antibody. In one embodiment, the heavy and light chain variable domain sequences are at least 70, 80, 85, 90, 92, 93, 94, 95, 97, 98, 99, or 100% identical to corresponding variable domain sequences of the D2-57 or the DX-2001 antibody.

In another aspect, the disclosure features a protein including an immunoglobulin heavy chain (HC) variable domain sequence and an immunoglobulin light chain (LC) variable domain sequence, wherein the HC variable domain sequence and the LC variable domain sequence form an antigen binding site that binds to an activated conformation of LFA-1, wherein the light chain variable domain sequence includes (a) a CDR1 that includes at least 7, 8, 9, 10, or 11 amino acids (of 11) from RASQSIGSYLN (SEQ ID NO:7), (b) a CDR2 that includes at least 4, 5, 6, or 7 amino acids (of 7) from AASSLQS (SEQ ID NO:8), and/or (c) a CDR3 that includes at least 5, 6, 7, or 8 (of 8) amino acids from QQSYSTPS (SEQ ID NO:9). The protein can include other features described herein. In one embodiment, the protein includes features of D2-57 or DX-2001, e.g., the CDR regions of the D2-57 or the DX-2001 antibody. In one embodiment, the heavy and light chain variable domain sequences are at least 70, 80, 85, 90, 92, 93, 94, 95, 97, 98, 99, or 100% identical to corresponding variable domain sequences of the D2-57 or the DX-2001 antibody.

In another aspect, the disclosure features a protein that includes an immunoglobulin heavy chain (HC) variable domain sequence and an immunoglobulin light chain (LC) variable domain sequence, wherein the HC variable domain sequence and the LC variable domain sequence form an antigen binding site that binds to an activated conformation of LFA-1, wherein the heavy chain variable domain sequence includes (a) a CDR1 that includes at least 3, 4, or 5 amino acids (of 5) from HYGMS (SEQ ID NO:10), (b) a CDR2 that includes at least 13, 14, 15, 16, or 17 amino acid (of 17) from VISPSGGRTLYADSVKG (SEQ ID NO:11); and/or (c) a CDR3 that includes at least 5, 6, 7, or 8 amino acids (of 8) from HYSYAMDV (SEQ ID NO: 12). In one embodiment, the protein includes features of C1-54, e.g., the CDR regions of the C1-54 antibody. In one embodiment, the heavy and light chain variable domain sequences are at least 70, 80, 85, 90, 92, 93, 94, 95, 97, 98, 99, or 100% identical to corresponding variable domain sequences of the C1-54 antibody.

In another aspect, the disclosure features a protein that includes an immunoglobulin heavy chain (HC) variable domain sequence and an immunoglobulin light chain (LC) variable domain sequence, wherein the HC variable domain sequence and the LC variable domain sequence form an antigen binding site that binds to an activated conformation of LFA-1, wherein the light chain variable domain sequence includes (a) a CDR1 that includes at least 7, 8, 9, 10, or 11 amino acids (of 11) from TASQSVDSNLA (SEQ ID NO: 13), (b) a CDR2 that includes at least 4, 5, 6, or 7 amino acids (of 7) from GASTRAT (SEQ ID NO: 14); and/or (c) a CDR3 that includes at least 6, 7, 8, 9, or 10 amino acids (of 10) from QQYNKWPPYS (SEQ ID NO:15). In one embodiment, the protein includes features of C1-54, e.g., the CDR regions of the C1-54 antibody. In one embodiment, the heavy and light chain variable domain sequences are at least 70, 80, 85, 90, 92, 93, 94, 95, 97, 98, 99, or 100% identical to corresponding variable domain sequences of the C1-54 antibody.

In another aspect, the disclosure features an antibody that includes an immunoglobulin heavy chain (HC) variable domain sequence and an immunoglobulin light chain (LC) variable domain sequence, wherein the HC variable domain sequence and the LC variable domain sequence form an antigen binding site that binds to an activated conformation of LFA-1. The heavy chain variable domain sequence includes (a) a CDR1 that includes at least 3, 4, or 5 amino acids (of 5) from HYSMQ (SEQ ID NO:16), (b) a CDR2 that includes at least 13, 14, 15, 16, or 17 amino acid (of 17) from YIGSSGGNTYYADSVKG (SEQ ID NO:17), and/or (c) a CDR3 that includes at least 7, 8, 9, or 10 amino acids (of 10) from GTYNTSPFDY (SEQ ID NO:18). In one embodiment, the protein includes features of P1-G10, e.g., the CDR regions of the P1-G10 antibody. In one embodiment, the heavy and light chain variable domain sequences are at least 70, 80, 85, 90, 92, 93, 94, 95, 97, 98, 99, or 100% identical to corresponding variable domain sequences of the P1-G10 antibody.

In another aspect, the disclosure features a protein that includes an immunoglobulin heavy chain (HC) variable domain sequence and an immunoglobulin light chain (LC) variable domain sequence, wherein the HC variable domain sequence and the LC variable domain sequence form an antigen binding site that binds to an activated conformation of LFA-1. The light chain variable domain sequence includes (a) a CDR1 that includes at least 7, 8, 9, 10, or 11 amino acids (of 11) from SGDALGQKYAS (SEQ ID NO: 19), (b) a CDR2 that includes at least 4, 5, 6, or 7 amino acids (of 7) from QDSKRPS (SEQ ID NO:20), and/or (c) a CDR3 that includes at least 5, 6, 7, 8, or 9 amino acids (of 9) from QAWDTTAYV (SEQ ID NO:21). In one embodiment, the protein includes features of P1-G10, e.g., the CDR regions of the P1-G10 antibody. In one embodiment, the heavy and light chain variable domain sequences are at least 70, 80, 85, 90, 92, 93, 94, 95, 97, 98, 99, or 100% identical to corresponding variable domain sequences of the P1-G10 antibody.

A protein described herein can have at least 30, 50, 60, 70, 80, 90 or 100% of the CDR amino acid residues that are not identical to residues in the reference CDR sequences be identical to residues at corresponding positions in a human germline sequence. The protein can have at least 30, 50, 60, 70, 80, 90 or 100% of the FR regions be identical to FR sequence from a human germline sequence or a FR sequence of D2-57, DX-2001, C1-54, or P1-G10. Exemplary human germline sequences include those of VKI-O2, VL2-1, VKIII-L2::JK2, vg3-23, V3-23::JH4, and V3-23::JK6 and others provided herein.

In another aspect, the disclosure features an antibody or a non-naturally occurring protein that preferentially binds to activated LFA-1 relative to inactivated LFA-1 and that competes with antibody D2-57, DX-2001, C1-54, or P1-G10 for binding to activated LFA-1.

In another aspect, the disclosure features an antibody or a non-naturally occurring protein that binds to an epitope that overlaps with an epitope recognized by antibody D2-57, DX-2001, C1-54, or P1-G10 on LFA-1, e.g., on activated LFA-1, or that binds to the same epitope as antibody D2-57, DX-2001, C1-54, or P1-G10.

In another aspect, the disclosure features a pharmaceutical composition that includes a protein described herein and a pharmaceutically acceptable salt. The invention also provides a kit that includes a protein described herein and instructions for therapeutic or diagnostic use.

In another aspect, the disclosure features a method of treating or preventing inflammation or an inflammatory disorder. The method includes: administering a protein described herein to a subject in an amount effective to treat or prevent the inflammation or the inflammatory disorder, e.g., to ameliorate at least one symptom of inflammation or the inflammatory disorder, or to delay the appearance of such symptom.

In one embodiment, the protein is administered at dosages less than 1, 0.7, 0.6, 0.5, 0.4, 0.3, 0.2, 0.1, 0.05, or 0.02 mg/kg per week, e.g., for at least 2, 3, 5, 10, or 52 weeks. For example, the recommended dose for the average patient can be less than 1, 0.7, 0.6, 0.5, 0.4, 0.3, 0.2, 0.1, 0.05, or 0.02 mg/kg per week, e.g., for at least 2, 3, 5, 10, or 52 weeks.

In one embodiment, the protein is administered at dosages effective to produce a detectable serum concentration whose mean trough concentration is less than 9, 8, 7, 6, 5, 4, 3, 2, 1 µg/ml. In one embodiment, the protein is administered in two phase, in which the first phase is characterized by administration of a first dose, and the second phase is characterized by administration of the second dose, different from the first dose. The first dose can be less than the second dose, or can be greater than the second dose, e.g., at least 20, 30, or 40% different.

For example, the first dose is an initial dose and, e.g., is less than 0.7, 0.6, 0.5, 0.4, 0.3, 0.2, 0.1, 0.05, or 0.02 mg/kg. The second dose can be less than 1, 0.7, 0.6, 0.5, 0.4, 0.3, 0.2, 0.1, 0.05, or 0.02 mg/kg.

In one embodiment, the subject has psoriasis or is predisposed to psoriasis. For example, the subject has stable, plaque psoriasis. In one embodiment, the subject has psoriasis whose minimum body surface involvement is at least 2, 5, 10, 15, 20, or 25%.

In one embodiment, the protein is administered to a subject who has not been treated with another systemic therapy or with phototherapy, e.g., in the previous 30, 60, 90, or 180 days.

The protein can be administered at dosages effective to increase white blood cell count by at least 5, 10, 15, 20, 25, 30, 35, 40, or 45%. The protein can be administered at dosages effective to increase eosinophils count by at least 5, 10, 15, 20, 25, 30, 35, 40, or 45%.

In another aspect, the disclosure features a method of treating or preventing inflammation or an inflammatory disorder. The method includes administering a protein described herein to a subject in an amount effective to ameliorate inflammation or the inflammatory disorder, wherein the protein does not substantially interact with non-activated LFA-1 molecules in the subject.

In one embodiment, the protein is administered at dosages less than 1, 0.7, 0.6, 0.5, 0.4, 0.3, 0.2, 0.1, 0.05, or 0.02 mg/kg per week, e.g., for at least 2, 3, 5, 10, or 52 weeks. For example, the recommended dose for the average patient can be less than 1, 0.7, 0.6, 0.5, 0.4, 0.3, 0.2, 0.1, 0.05, or 0.02 mg/kg per week, e.g., for at least 2, 3, 5, 10, or 52 weeks.

In one embodiment, the protein is administered at dosages effective to produce a detectable serum concentration whose mean trough concentration is less than 9, 8, 7, 6, 5, 4, 3, 2, 1 µg/ml. In one embodiment, the protein is administered in two phase, in which the first phase is characterized by administration of a first dose, and the second phase is characterized by administration of the second dose, different from the first dose. The first dose can be less than the second dose, or can be greater than the second dose, e.g., at least 20, 30, or 40% different.

For example, the first dose is an initial dose and, e.g., is less than 0.7, 0.6, 0.5, 0.4, 0.3, 0.2, 0.1, 0.05, or 0.02 mg/kg. The second dose can be less than 1, 0.7, 0.6, 0.5, 0.4, 0.3, 0.2, 0.1, 0.05, or 0.02 mg/kg.

In one embodiment, the subject has psoriasis or is predisposed to psoriasis. For example, the subject has stable, plaque psoriasis. In one embodiment, the subject has psoriasis whose minimum body surface involvement is at least 2, 5, 10, 15, 20, or 25%.

In one embodiment, the protein is administered to a subject who has not been treated with another systemic therapy or with phototherapy, e.g., in the previous 30, 60, 90, or 180 days.

The protein can be administered at dosages effective to increase white blood cell count by at least 5, 10, 15, 20, 25, 30, 35, 40, or 45%. The protein can be administered at dosages effective to increase eosinophils count by at least 5, 10, 15, 20, 25, 30, 35, 40, or 45%.

In another aspect, the disclosure features a method of treating or preventing an inflammation or an inflammatory disorder. The method includes: administering a protein described herein to a subject in an amount that is less than the amount required to treat or prevent inflammation or the inflammatory disorder using an antibody that does not preferentially bind to activated LFA-1 (e.g., binds to both activated and inactivated LFA-1 with substantially the same affinity, e.g., RAPTIVA®), wherein the protein does not substantially interact with non-activated LFA-1 molecules exposed on leukocytes of the subject.

In one embodiment, the protein is administered at dosages less than 1, 0.7, 0.6, 0.5, 0.4, 0.3, 0.2, 0.1, 0.05, or 0.02 mg/kg per week, e.g., for at least 2, 3, 5, 10, or 52 weeks. For example, the recommended dose for the average patient can be less than 1, 0.7, 0.6, 0.5, 0.4, 0.3, 0.2, 0.1, 0.05, or 0.02 mg/kg per week, e.g., for at least 2, 3, 5, 10, or 52 weeks. For example, the protein is administered at a dose less than RAPTIVA® to achieve substantially the same result.

In one embodiment, the protein is administered at dosages effective to produce a detectable serum concentration whose mean trough concentration is less than 9, 8, 7, 6, 5, 4, 3, 2, 1 µg/ml. In one embodiment, the protein is administered in two phase, in which the first phase is characterized by administration of a first dose, and the second phase is characterized by administration of the second dose, different from the first dose. The first dose can be less than the second dose, or can be greater than the second dose, e.g., at least 20, 30, or 40% different.

For example, the first dose is an initial dose and, e.g., is less than 0.7, 0.6, 0.5, 0.4, 0.3, 0.2, 0.1, 0.05, or 0.02 mg/kg. The second dose can be less than 1, 0.7, 0.6, 0.5, 0.4, 0.3, 0.2, 0.1, 0.05, or 0.02 mg/kg.

In one embodiment, the subject has psoriasis or is predisposed to psoriasis. For example, the subject has stable, plaque psoriasis. In one embodiment, the subject has psoriasis whose minimum body surface involvement is at least 2, 5, 10, 15, 20, or 25%.

In one embodiment, the protein is administered to a subject who has not been treated with another systemic therapy or with phototherapy, e.g., in the previous 30, 60, 90, or 180 days.

The protein can be administered at dosages effective to increase white blood cell count by at least 5, 10, 15, 20, 25, 30, 35, 40, or 45%. The protein can be administered at dosages effective to increase eosinophils count by at least 5, 10, 15, 20, 25, 30, 35, 40, or 45%.

In another aspect, the disclosure features a method of treating or preventing an inflammation or an inflammatory disorder. The method includes: administering a protein described herein to a subject in an amount effective to ameliorate or delay appearance of at least one symptom of inflammation or the inflammatory disorder, wherein cells in the subject that do not present an activated LFA-1 protein on their surface are not targeted by the protein.

In one embodiment, the protein is administered at dosages less than 1, 0.7, 0.6, 0.5, 0.4, 0.3, 0.2, 0.1, 0.05, or 0.02 mg/kg per week, e.g., for at least 2, 3, 5, 10, or 52 weeks. For example, the recommended dose for the average patient can be less than 1, 0.7, 0.6, 0.5, 0.4, 0.3, 0.2, 0.1, 0.05, or 0.02 mg/kg per week, e.g., for at least 2, 3, 5, 10, or 52 weeks.

In one embodiment, the protein is administered at dosages effective to produce a detectable serum concentration whose mean trough concentration is less than 9, 8, 7, 6, 5, 4, 3, 2, 1 µg/ml. In one embodiment, the protein is administered in two phase, in which the first phase is characterized by administration of a first dose, and the second phase is characterized by administration of the second dose, different from the first dose. The first dose can be less than the second dose, or can be greater than the second dose, e.g., at least 20, 30, or 40% different.

For example, the first dose is an initial dose and, e.g., is less than 0.7, 0.6, 0.5, 0.4, 0.3, 0.2, 0.1, 0.05, or 0.02 mg/kg. The second dose can be less than 1, 0.7, 0.6, 0.5, 0.4, 0.3, 0.2, 0.1, 0.05, or 0.02 mg/kg.

In one embodiment, the subject has psoriasis or is predisposed to psoriasis. For example, the subject has stable, plaque psoriasis. In one embodiment, the subject has psoriasis whose minimum body surface involvement is at least 2, 5, 10, 15, 20, or 25%.

In one embodiment, the protein is administered to a subject who has not been treated with another systemic therapy or with phototherapy, e.g., in the previous 30, 60, 90, or 180 days.

The protein can be administered at dosages effective to increase white blood cell count by at least 5, 10, 15, 20, 25, 30, 35, 40, or 45%. The protein can be administered at dosages effective to increase eosinophils count by at least 5, 10, 15, 20, 25, 30, 35, 40, or 45%.

For example, the subject has or is predisposed to a disorder that is caused at least in part by a T cell inflammatory response. In a preferred embodiment, the disorder is rheumatoid arthritis or psoriasis.

For example, the subject has or is predisposed to an inflammatory disorder selected from the group consisting of: allergic conditions such as eczema and asthma, Reiter's syndrome, HIV, cytokine-induced toxicity, transient hypogammaglobulinemia, malignancies (e.g., B-cell malignancies such as chronic lymphocytic leukemia or hairy cell leukemia), diseases involving leukocyte diapedesis, acute glomerulonephritis, asthma, immune deficiency disorders, invasion of tumor cells into secondary organs etc., insulinitis, atherosclerosis, conditions involving infiltration of T cells and chronic inflammatory responses, selective IgA deficiency, meningitis, chronic mucocutaneous, dermatoses with acute inflammatory components, sarcoidosis, skin hypersensitivity reactions (including poison ivy and poison oak), urticaria, nephrotic syndrome, acute appendicitis, inflammatory bowel disease (such as Crohn's disease and ulcerative colitis), encephalitis, wound healing, chronic obstructive pulmonary disease, myasthenia gravis, congenital X-linked infantile hypogammaglobulinemia, lupus, adult respiratory distress syndrome, orbital inflammatory disease, inflammatory breast disease, uveitis, psoriasis, HIV and rhinovirus infection, a CNS inflammatory disorder, antigen-antibody complex mediated diseases, necrotizing enterocolitis, amyloidosis, thermal injury, bronchitis, leukocyte adhesion deficiency II syndrome, autoimmune hemolytic anemia, peritonitis, pulmonary fibrosis, septic shock, multiple organ injury syndrome secondary to septicemia or trauma, leukapheresis, pernicious anemia, nephritis, chronic bronchitis, common variable immunodeficiency, scleroderma, glomerulonephritis, polymyositis, pelvic inflammatory disease, rhinitis, granulocyte transfusion associated syndromes, ulcerative colitis and Crohns' disease), viral infection, hemodialysis, autoimmune diseases (e.g., granulomatosis and vasculitis), lung inflammation, reactive arthritis, dermatitis, and leukocyte adhesion deficiency. Example of autoimmune disorders include: rheumatoid arthritis, systemic lupus erythematosus (SLE), diabetes mellitus, multiple sclerosis, Reynaud's syndrome, autoimmune thyroiditis, experimental autoimmune encephalomyelitis, Sjorgen's syndrome, juvenile onset diabetes, and immune responses associated with delayed hypersensitivity mediated by cytokines and T-lymphocytes typically found in tuberculosis, sarcoidosis, and polymyositis.

In one embodiment, the protein is administered at a dosage that does not substantially increase risk for serious infection (e.g., no more than 0.4% of patients), risk for thrombocytopenia (e.g., no more than 0.3% of patients), risk for psoriasis aggravation (e.g., no more than 0.7% of patients), or risk or headache, chill, fever, nausea, myalgia, pain, arthritis, or arthralgia (e.g., no more than 32, 13, 7, 11, 8, 10, 0.4, and 0.3% of patients, respectively). In one embodiment, the protein can the same frequency of side effects as RAPTIVA®, or less.

In another aspect, the disclosure features a method of suppressing an immune response. The method includes a protein described herein to a subject in an amount effective to suppress an immune response of the subject. In one embodiment, the subject has or is about to receive a transplant.

In another aspect, the disclosure features a method of treating or preventing a disorder in a subject. The method includes: identifying a subject in need of an anti-LFA-1 antibody that preferentially binds to the activated form of LFA-1, but which subject does not respond or tolerate an anti-LFA-1 antibody that binds to activated and non-activated LFA-1 protein with substantially the same affinity; and administering the anti-LFA-1 antibody that preferentially binds to the activated form of LFA-1, to the subject.

In another aspect, the disclosure features a method of modulating aLFA-1 activity. The method includes: providing an aLFA-1-binding protein of claim 1; and contacting the protein to aLFA-1, in an amount sufficient to modulate aLFA-1 activity.

For example, the contacting is in vitro or in vivo.

In one embodiment, the protein is contacted to aLFA-1 in the vicinity of a neoplastic cell (e.g., a cell found in laryngeal, epidermal, pulmonary, breast, renal, urothelial, colonic, prostatic, or hepatic cancer and/or metastasis). In one embodiment, the protein is contacted to aLFA-1 in the vicinity of an endothelial cell.

In another aspect, the disclosure features a method for detecting the presence of an aLFA-1 protein, in a sample, e.g., in vitro. The method includes: (i) contacting the sample (and optionally, a reference, e.g., control, sample) with an aLFA-1-binding protein described herein, under conditions that allow interaction of the aLFA-1-binding protein and the aLFA-1 protein to occur; and (ii) detecting interaction between the aLFA-1-binding protein, and the sample (and optionally, the reference, e.g., control, sample).

At least one of the aLFA-1 binding protein or the aLFA-1 is immobilized.

In another aspect, the disclosure features a method for detecting the presence of aLFA-1 (e.g., activated aLFA-1), e.g., in vivo. The method includes: (i) administering to a subject (and optionally a control subject) an aLFA-1-binding protein, under conditions that allow interaction of the aLFA-1-binding protein and the aLFA-1 protein to occur; and (ii) detecting location of the aLFA-1-binding protein in the subject or formation of a complex between the aLFA-1-binding protein and aLFA-1 in the subject. For example, the subject is a human subject. The detecting can include imaging the subject. For example, the aLFA-1-binding protein is labeled with an MRI detectable label.

The invention also includes a protein that includes an immunoglobulin heavy chain (HC) variable domain sequence and an immunoglobulin light chain (LC) variable domain sequence The HC variable domain sequence and the LC variable domain sequence form an antigen binding site that detectably binds to both an integrin I-domain in the activated conformation and an integrin I-domain in the non-activated conformation, but preferentially binds to an integrin in the activated conformation relative to binding to the integrin in the non-activated conformation.

For example, the protein has at least a 1.5, 2, 3, 4, 5, 10, 15, 20, 50, 70, 80, 100, 500, or 1000 fold preference for binding to activated LFA-1 relative to inactivated LFA-1.

The protein can have at least a 1.5, 2, 3, 4, 5, or 10 preference for binding to activated LFA-1 relative to inactivated LFA-1, but no more than a 15, 20, 50, 70, 80, 100, 500, or 1000 fold preference.

The invention also includes a protein that includes an immunoglobulin heavy chain (HC) variable domain sequence and an immunoglobulin light chain (LC) variable domain sequence. The HC variable domain sequence and the LC variable domain sequence form an antigen binding site that detectably binds to both an integrin I-domain in the open conformation and an integrin I-domain in the closed conformation, but preferentially binds to the integrin I-domain in the open conformation relative to the integrin I-domain in the closed conformation.

For example, the protein has at least a 1.5, 2, 3, 4, 5, 10, 15, 20, 50, 70, 80, 100, 500, or 1000 fold preference for binding to activated LFA-1 relative to inactivated LFA-1.

The protein can have at least a 1.5, 2, 3, 4, 5, or 10 preference for binding to activated LFA-1 relative to inactivated LFA-1, but no more than a 15, 20, 50, 70, 80, 100, 500, or 1000 fold preference. In one embodiment, protein can bind to a disulfide-locked K287C/K294C I-domain.

The invention also includes a protein that includes an immunoglobulin heavy chain (HC) variable domain sequence and an immunoglobulin light chain (LC) variable domain sequence, wherein the HC variable domain sequence and the LC variable domain sequence form an antigen binding site that detectably binds to both an integrin I-domain of LFA-1 in the activated conformation and an integrin I-domain in the non-activated conformation, but preferentially binds to activated LFA-1 relative to non-activated LFA-1. For example, the protein has at least a 1.5, 2, 3, 4, 5, 10, 15, 20, 50, 70, 80, 100, 500, or 1000 fold preference for binding to activated LFA-1 relative to inactivated LFA-1. The protein can have at least a 1.5, 2, 3, 4, 5, or 10 preference for binding to activated LFA-1 relative to inactivated LFA-1, but no more than a 15, 20, 50, 70, 80, 100, 500, or 1000 fold preference. In one embodiment, the I-domain in the open conformation is a disulfide-locked K287C/K294C I-domain.

Exemplary antibodies can include the following sequences or segments thereof:

TABLE 1

Exemplary Variable Domains

| Name | Amino Acid Sequence |
|---|---|
| D2-57 LC SEQ ID NO: 22 | DIQMTQSPSSLSASVGDRVTITC RASQSIGSYLN WYQQKTGKAPKALIY AASSLQS GVPSRFSGSGSGTDFTLTISSLQLEDFATYYC QQSY STPSFGQGTKVEIKRT |
| D2-57 HC SEQ ID NO: 23 | EVQLLESGGGLVQPGGSLRLSCAASGFTFS RYVMW WVRQAPGKGLEWVS YIWPSGGNTYYADSVKG RFTISRDNSKNTLYLQMNSLRAEDTAVYYCAS SYDF WSNAFDIWGQGTMVTVSS |
| DX-2001 LC SEQ ID NO: 24 | DIQMTQSPSSLSASVGDRVTITC RASQSIGSYLN WYQQKPGKAPKALIY AASSLQS GVPSRFSGSGSGTDFTLTISSLQPEDFATYYC QQSYSTPSFGQGTKVEIKRT |
| DX-2001 HC SEQ ID NO: 25 | EVQLLESGGGLVQPGGSLRLSCAASGFTFS RYVMW WVRQAPGKGLEWVS YIWPSGGNTYYADSVKG RFTISRDNSKNTLYLQMNSLRAEDTAVYYCAS SYDFWSNAFDIWGQGTMVTVSS |
| C1-54 LC SEQ ID NO: 26 | DIQMTQSPATLSVSPGERVTLSCTASQSVDSNLA WYQQKPGQAPRLLVY GASTRAT GVPARFSGSGSGTAFTLTIDSLQSEDFAVYYC QQYN KWPPYSFGQGTKLEIKRT |
| C1-54 HC SEQ ID NO: 27 | EVQLLESGGGLVQPGGSLRLSCAASGFTFS HYGMS WVRQAPGKGLEWVS VISPSGGRTLYADSVKG RFTISRDNSKNTLYLQMNSLRAEDTAVYYCAK HYSY AMDVWGQGTTVTVSS |
| P1-G10 LC SEQ ID NO: 28 | SVLTQPPSVSVSPGQTASVTC SGDALGQKYAS WYQQKPGQSPVLVIF QDSKRPS GIPERFSGSNSGNTATLTISGTQAVDEADYYC QAWD TTAYVFGTGTKVTVL |
| P1-G10 HC SEQ ID NO: 29 | EVQLLESGGGLVQPGGSLRLSCAASGFTFS HYSMQ WVRQAPGKGLEWVS YIGSSGGNTYYADSVKG RFTISRDNSKNTLYLQMNSLPAEDTAVYYCAR GTYN TSPFDYWGQGTLVTVSS |

Versions of the heavy chain variable domain can omit, e.g., the N-terminal glutamic acid.

An integrin binding antibody is typically monospecific, e.g., a monoclonal antibody, or antigen-binding fragment thereof. The aLFA-1-binding antibodies can be full-length (e.g., an IgG (e.g., an IgG1, IgG2, IgG3, IgG4), IgM, IgA (e.g., IgA1, IgA2), IgD, and IgE) or can include only an antigen-binding fragment (e.g., a Fab, F(ab')$_2$ or scFv fragment). The antibody, or antigen-binding fragment thereof, can include two heavy chain immunoglobulins and two light chain immunoglobulins, or can be a single chain antibody. The antibodies can, optionally, include a constant region chosen from a kappa, lambda, alpha, gamma, delta, epsilon or a mu constant region gene. An aLFA-1-binding antibody can include a heavy and light chain constant region substantially from a human antibody, e.g., a human IgG1 IgG2, IgG3, or IgG4 constant region or a portion thereof. The constant region can have the sequence of an A or non-A allotype.

In one embodiment, the antibody is a recombinant or modified antibody, e.g., a chimeric, a humanized, a deimmunized, or an in vitro generated antibody. The term "recombinant" or "modified" antibody, as used herein, is intended to include all antibodies that are prepared, expressed, created or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes or antibodies prepared, expressed, created or isolated by any other means that involves splicing of human immunoglobulin gene sequences to other DNA sequences. Such recombinant antibodies include human, humanized, CDR grafted, chimeric, deimmunized, in vitro generated antibodies, and may optionally include framework and/or constant regions derived from human germline immunoglobulin-encoding nucleic acid sequences.

In one embodiment, the antibody binds to an epitope distinct from an epitope bound by known antibodies that bind to LFA-1. For example, the antibody binds to an epitope that distinct from one or more of the epitopes bound by MHM23 (Hildreth et al., Eur. J. Immunol. 13:202-208 (1983)); MHM24; RAPTIVA®; M18/2 (IgG.sub.2a; Sanches-Madrid et al., J. Exp. Med. 158:586 (1983)); mAb25 (Dranfield et al, J. Cell Biol. 1992 January; 116(1):219-26.) H52 (American Type Culture Collection (ATCC) Deposit HB 10160); NKI-L16 (Landis et al., J. Cell Biol. 1993 March; 120(6):1519-27); MEM-83 (Landis et al., supra); 7E3; Mas191c and IOT18 (Vermot Desroches et al., Scand. J. Immunol. 33:277-286 (1991)); and NA-8 (WO 94/12214). In other embodiments, the antibody does not compete with such antibodies for bind to LFA-1. In still other embodiments, the antibody does not compete with an antibody described herein.

In one embodiment, the antibody binds to overlapping epitopes of, or competitively inhibits, the binding of an antibody disclosed herein to aLFA-1, e.g., D2-57, DX-2001, C1-54, or P1-G10. In one embodiment, the antibody binds to an epitope that includes an amino acid that is within at least 12, 10, 8, 6, 5, or 3 amino acids of an epitope bound by an antibody described herein (e.g., D2-57, DX-2001, C1-54, or P1-G10). In one embodiment, the antibody includes an antigen binding site structure that recognizes one or more side chains that are positioned within 12, 10, 8, 6 or 4 Angstroms of an antibody described herein (e.g., D2-57, DX-2001, C1-54, or P1-G10). The epitope is generally in the extracellular region of LFA-1. The epitope can include one or more amino acid side chains on the α and/or β subunit. In one embodiment, the epitope includes one or more amino acid side chains on the I-domain of αL.

Further, any combination of aLFA-1-binding antibodies is within the scope of the invention, e.g., two or more antibodies that bind to different regions of aLFA-1, e.g., antibodies that bind to two different epitopes on the extracellular domain of aLFA-1, e.g., a bispecific antibody.

In one embodiment, the aLFA-1-binding antibody includes at least one light or heavy chain immunoglobulin (or two light chain immunoglobulins and two heavy chain immunoglobulins). Preferably, each immunoglobulin includes a light or a heavy chain variable region having at least one, two and, preferably, three complementarity determining regions (CDRs) substantially identical to a CDR from a light or heavy chain variable region, respectively, of an antibody described herein.

An integrin binding protein described herein can be used alone, e.g., can be administered to a subject or used in vitro in non-derivatized or unconjugated forms. In other embodiments, the integrin binding protein can be derivatized, modified or linked to another functional molecule, e.g., another polypeptide, protein, isotope, cell, or insoluble support. For example, the integrin binding protein can be functionally linked (e.g., by chemical coupling, genetic fusion, non-covalent association or otherwise) to one or more other molecular entities, such as an antibody (e.g., if the binding protein is an antibody, to form a bispecific or a multi-specific antibody), a toxin, a label, a serum-residence prolonging moiety (e.g. PEG), a therapeutic (e.g., a cytotoxic or cytostatic) agent or other moiety. An antibody can also be designed so that it can mediate complement-dependent cytotoxicity (CDC) or antibody-dependent cellular cytotoxicity (ADCC), or so that it does not mediate CDC or ADCC. For example, it can have a CDC- or ADCC-competent Fc domain, or a CDC- or ADCC-incompetent Fc domain.

In another aspect, the disclosure features a nucleic acid that includes a coding sequence that encodes a polypeptide including an immunoglobulin heavy chain variable domain sequence that binds to aLFA-1, e.g., an immunoglobulin heavy chain variable domain described herein. For example, the immunoglobulin heavy chain variable domain sequence can include: a CDR motif or CDR described herein. The immunoglobulin heavy chain variable domain sequence can include a framework region described herein. In one example, the variable domain sequence is a heavy chain variable domain is at least 75, 80, 85, 90, 95, 96, 97, 98, or 99% identical to an amino acid sequence described herein or a variable domain sequence thereof.

In another aspect, the disclosure features a nucleic acid that includes a coding sequence that encodes a polypeptide including an immunoglobulin light chain variable domain sequence that binds to aLFA-1, e.g., an immunoglobulin light chain variable domain described herein. For example, the immunoglobulin light chain variable domain sequence can include: a CDR motif or CDR described herein. The immunoglobulin light chain variable domain sequence can include a framework region described herein. In one example, the variable domain sequence is a light chain variable domain is at least 75, 80, 85, 90, 95, 96, 97, 98, or 99% identical to an amino acid sequence described herein or a variable domain sequence thereof.

A nucleic acid described herein can further include a promoter operably linked to the coding sequence. A nucleic acid can include a first and second coding sequence, e.g., wherein the first coding sequence encodes a polypeptide that includes an immunoglobulin heavy chain variable domain and the second coding sequence encodes a polypeptide that includes an immunoglobulin light chain variable domain.

In another aspect, the disclosure features a host cell that contains a first nucleic acid encoding a polypeptide including a heavy chain variable region and a second nucleic acid encoding a polypeptide including a light chain variable region. The heavy chain variable region and the light chain variable region can associate to form an aLFA-1 binding protein. These variable regions can have one or more properties described herein, e.g., at least 75, 80, 85, 90, 95, 96, 97, 98, or 99% identity to a sequence described herein, e.g., the sequence of a variable domain from an isolated antibody described herein or a human germline sequence described herein. The invention also includes a method of providing an aLFA-1-binding antibody. The method can include providing a host cell described herein; and expressing said first and second nucleic acids in the host cell under conditions that allow assembly of said light and heavy chain variable regions to form an antigen binding protein that interacts with aLFA-1.

In another aspect, the disclosure features a binding protein that includes a human or effectively human heavy chain immunoglobulin variable domain and a human or effectively human light chain immunoglobulin variable domain, wherein the binding protein binds to human aLFA-1. The protein can bind to aLFA-1 with a $K_d$ of less than, $10^{-7}$, $10^{-8}$, $10^{-9}$, or $10^{-10}$ M. The protein can include one or more additional features described herein.

In yet another aspect, the disclosure features a method of producing an aLFA-1-binding antibody, or antigen-binding fragment thereof. The method includes: providing a host cell that contains a first nucleic acid sequence encoding a polypeptide including a heavy chain variable region, e.g., a heavy chain variable region as described herein; providing a second nucleic acid sequence encoding a polypeptide including a light chain variable region, e.g., a light chain variable region as described herein; and expressing said first and second nucleic acid sequences in the host cell under conditions that allow assembly of said light and heavy chain variable regions to form an antigen binding protein that interacts with aLFA-1. The first and second nucleic acid sequences can be linked or unlinked, e.g., expressed on the same or different vector, respectively. The first and second nucleic acid sequences can be components of the same molecule or can reside on different molecules (e.g., different chromosomes or plasmids).

The host cell can be a eukaryotic cell, e.g., a mammalian cell, an insect cell, a yeast cell, or a prokaryotic cell, e.g., *E. coli*. For example, the mammalian cell can be a cultured cell or a cell line. Exemplary mammalian cells include lymphocytic cell lines (e.g., NSO), Chinese hamster ovary cells (CHO), COS cells, oocyte cells, and cells from a transgenic animal, e.g., mammary epithelial cell. For example, nucleic acids encoding the antibodies described herein can be expressed in a transgenic animal. In one embodiment, the nucleic acids are placed under the control of a tissue-specific promoter (e.g., a mammary specific promoter) and the antibody is produced in the transgenic animal. For example, the antibody molecule is secreted into the milk of the transgenic animal, such as a transgenic cow, pig, horse, sheep, goat or rodent.

In another aspect, the disclosure features a method of treating or preventing an inflammatory disorder in a subject. The method includes providing an aLFA-1-binding protein, e.g. a protein described herein, and contacting the subject with the protein, in an amount sufficient to modulate or prevent the inflammatory disorder. The method can include identifying a subject as having or being at risk for having an inflammatory disorder.

The subject can be a mammal, e.g., a primate, preferably a higher primate, e.g., a human (e.g., a patient having, or at risk of, a disorder described herein).

The aLFA-1-binding protein can be administered to the subject systemically (e.g., orally, parenterally, subcutaneously, intravenously, intramuscularly, intraperitoneally, intranasally, transdermally, or by inhalation), topically, or by application to mucous membranes, such as the nose, throat and bronchial tubes.

The method can further include monitoring at least one indicator of inflammation, e.g., local temperature, swelling (e.g., as measured), redness, local or systemic white blood cell count, presence or absence of neutrophils, cytokine levels, elastase activity, and so forth. The subject can be monitored in one or more of the following periods: prior to beginning of treatment; during the treatment; or after one or more elements of the treatment have been administered. Monitoring can be used to evaluate the need for further treatment with the same aLFA-1-binding protein or other agents. A desired change in one or more of the parameters described above can be indicative of the improved condition of the subject. Information about the monitoring can be recorded, e.g., in electronic or digital form.

In another aspect, the disclosure features methods for detecting the presence of an aLFA-1 protein, in a sample, in vitro (e.g., a biological sample or a tissue biopsy). The subject method can be used to evaluate, e.g., diagnose or stage a disorder described herein. The method includes: (i) contacting the sample (and optionally, a reference, e.g., control, sample) with an aLFA-1-binding protein, as described herein, under conditions that allow interaction of the aLFA-1-binding protein and the LFA-1 protein to occur; and (ii) detecting aLFA-1, e.g., by detecting formation of a complex between the LFA-1-binding protein and LFA-1, or by detecting an interaction between the aLFA-1-binding protein and LFA-1, in the sample (and optionally, the reference, e.g., control, sample). Formation of the complex can be indicative of the presence of aLFA-1 protein (e.g., activated aLFA-1 protein), and can indicate the suitability or need for a treatment described herein. For example, a statistically significant change in the formation of the complex in the sample relative to the reference sample, e.g., the control sample, is indicative of the presence of activated aLFA-1 in the sample.

In yet another aspect, the invention provides a method for detecting the presence of LFA-1 (e.g., activated aLFA-1) in vivo (e.g., in vivo imaging in a subject). The subject method can be used to evaluate, e.g., diagnose, localize, or stage a disorder described herein, e.g., inflammation, an inflammatory disorder, a disorder characterized by excessive LFA-1 activity, or a LFA-1 mediated disorder. The method includes: (i) administering to a subject (and optionally a control subject) an aLFA-1-binding protein (e.g., an antibody or antigen binding fragment thereof), under conditions that allow interaction of the aLFA-1-binding protein and the aLFA-1 protein to occur; and (ii) detecting formation of a complex between the binding protein and aLFA-1, wherein a statistically significant change in the formation of the complex in the subject relative to the reference, e.g., the control subject or subject's baseline, is indicative of the presence of the aLFA-1. The presence of activated aLFA-1 in particular locations within a subject can be indicative of inflammation or an inflammatory disorder.

In other embodiments, a method of diagnosing or staging, a disorder as described herein (e.g., an inflammatory disorder, a disorder characterized by excessive LFA-1 activity, or a LFA-1 mediated disorder), is provided. The method includes: (i) identifying a subject having, or at risk of having, the disorder; (ii) obtaining a sample of a tissue or cell affected with the disorder; (iii) contacting said sample or a control sample with an aLFA-1-binding protein, under conditions that allow interaction of the binding agent and the aLFA-1 protein to occur, and (iv) detecting formation of a complex. A statistically significant increase in the formation of the complex between the binding protein and LFA-1 with respect to a reference sample, e.g., a control sample, is indicative of the disorder or the stage of the disorder. In one embodiment, the sample is obtained by non-surgical means, e.g., by a blood, saliva, or urine sample. In another embodiment, surgery is used.

Preferably, the aLFA-1-binding protein used in the in vivo and in vitro diagnostic methods is directly or indirectly labeled with a detectable substance to facilitate detection of the bound or unbound binding agent.

Although many embodiments of the disclosure are described in the context of binding proteins that preferentially bind to activated LFA-1 ("aLFA-1"), proteins that preferentially bind to a conformer of another target protein (e.g., another integrin, e.g., another leukocyte integrin subfamily member) or a different LFA-1 conformer can also be made and used.

DEFINITIONS

The term "binding protein" refers to a protein that can interact with a target molecule. An "integrin binding protein" refers to a protein that can interact with an integrin, and includes, in particular proteins that preferentially interact with an activated integrin, e.g., aLFA-1, or mimic thereof.

As used herein, the term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab fragments, F(ab')$_2$, a Fd fragment, a Fv fragments, and dAb fragments) as well as complete antibodies.

The VH and VL regions can be further subdivided into regions of hypervariability, termed "complementarity determining regions" ("CDR"), interspersed with regions that are more conserved, termed "framework regions" (FR). The extent of the framework region and CDRs has been precisely defined (see, Kabat, et al. (1991) *Sequences of Proteins of Immunological Interest, Fifth Edition*, U.S. Department of Health and Human Services, NIH Publication No. 91-3242, and Chothia, C. et al. (1987) J. Mol. Biol. 196:901-917). Kabat definitions are used herein. Each VH and VL is typically composed of three CDRs and four FRs, arranged from amino-terminus to carboxy-terminus in the following order: FR1, CDR1, FR2, CDR2, FR3, CDR3, FR4.

An "immunoglobulin domain" refers to a domain from the variable or constant domain of immunoglobulin molecules. Immunoglobulin domains typically contain two β-sheets formed of about seven β-strands, and a conserved disulphide bond (see, e.g., A. F. Williams and A. N. Barclay 1988 *Ann. Rev Immunol.* 6:381-405). The canonical structures of hypervariable loops of an immunoglobulin variable domain can be inferred from its sequence, e.g., as described in Chothia et al. (1992) *J. Mol. Biol.* 227:799-817; Tomlinson et al. (1992) *J. Mol. Biol.* 227:776-798); and Tomlinson et al. (1995) EMBO J. 14(18):4628-38.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes immunoglobulin variable domain sequence can associate with another immunoglobulin variable domain sequence to form a target binding structure (or "antigen binding site"), e.g., a structure that preferentially interacts with an activated integrin structure or a mimic of an activated integrin structure, e.g., relative to an non-activated structure.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region includes three domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The term "antibody" includes intact immunoglobulins of types IgA, IgG, IgE, IgD, IgM (as well as subtypes thereof). The light chains of the immunoglobulin may be of types kappa or lambda. In one embodiment, the antibody is glycosylated. An antibody can be functional for antibody-dependent cytotoxicity and/or complement-mediated cytotoxicity.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and LC CDR3. Each of the light chain CDRs can be human. HC CDR3 can be human. One or more of the framework regions can be human, e.g., FR1, FR2, FR3, and FR4 of the HC or LC. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. One or more of the constant regions can be human or effectively human. In another embodiment, at least 70, 75, 80, 85, 90, 92, 95, or 98% of, or the entire antibody can be human or effectively human.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the carboxy terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

The term "antigen-binding fragment" of a full length antibody (or simply "antibody portion," or "fragment"), as used herein, refers to one or more fragments of a full-length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')$_2$ fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., Bird et al. (1988) *Science* 242:423-426; and Huston et al. (1988) *Proc. Natl. Acad. Sci. USA* 85:5879-5883.

Antibody fragments can be obtained using any appropriate technique including conventional techniques known to those with skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition. As used herein, "isotype" refers to the antibody class (e.g., IgM or IgG1) that is encoded by heavy chain constant region genes.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

A "humanized" immunoglobulin variable region is an immunoglobulin variable region that is modified to include a sufficient number of human framework amino acid positions such that the immunoglobulin variable region does not elicit an immunogenic response in a normal human. Descriptions of "humanized" immunoglobulins include, for example, U.S. Pat. No. 6,407,213 and U.S. Pat. No. 5,693,762.

As used herein, "binding affinity" refers to the apparent association constant or $K_a$. The $K_a$ is the reciprocal of the dissociation constant ($K_d$). A binding protein may, for example, have a binding affinity of at least $10^{-5}$, $10^{-6}$, $10^{-7}$ or $10^{-8}$ M for a particular target molecule. Higher affinity binding of a binding ligand to a first target relative to a second target can be indicated by a higher $K_a$ (or a smaller numerical value $K_d$) for binding the first target than the $K_a$ (or numerical value $K_d$) for binding the second target. In such cases the binding protein has specificity for the first target (e.g., a protein in a first conformation or mimic thereof) relative to the second target (e.g., the same protein in a second conformation or mimic thereof). Differences in binding affinity (e.g., for specificity or other comparisons) can be at least 1.5, 2, 3, 4, 5, 10, 15, 20, 50, 70, 80, 100, 500, 1000, or $10^5$ fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in PBS (phosphate buffered saline) at pH 7.2 at 30° C. These techniques can be used to measure the concentration of bound and free binding protein as a function of binding protein (or target) concentration. The concentration of bound binding protein ([Bound]) is related to the concentration of free binding protein ([Free]) and the concentration of binding sites for the binding protein on the target where (N) is the number of binding sites per target molecule by the following equation:

$$[\text{Bound}] = N[\text{Free}]/((1/K_a) + [\text{Free}]).$$

It is not always necessary to make an exact determination of Ka, though, since sometimes it is sufficient to obtain a quantitative measurement of affinity, e.g., determined using a method such as ELISA or FACS analysis, is proportional to Ka, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

An "isolated composition" refers to a composition that is removed from at least 90% of at least one component of a natural sample from which the isolated composition can be obtained. Compositions produced artificially or naturally can be "compositions of at least" a certain degree of purity if the species or population of species of interests is at least 5, 10, 25, 50, 75, 80, 90, 92, 95, 98, or 99% pure on a weight-weight basis.

An "epitope" refers to the site on a target compound that is bound by a binding protein (e.g., an antibody such as a Fab or full length antibody). In the case where the target compound is a protein, the site can be entirely composed of amino acid components, entirely composed of chemical modifications of amino acids of the protein (e.g., glycosyl moieties), or composed of combinations thereof. Overlapping epitopes include at least one common amino acid residue.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

In a preferred embodiment, the length of a reference sequence aligned for comparison purposes is at least 30%, preferably at least 40%, more preferably at least 50%, even more preferably at least 60%, and even more preferably at least 70%, 80%, 90%, 92%, 95%, 97%, 98%, or 100% of the length of the reference sequence. For example, the reference sequence may be the length of the immunoglobulin variable domain sequence.

As used herein, the term "substantially identical" (or "substantially homologous") is used herein to refer to a first amino acid or nucleic acid sequence that contains a sufficient number of identical or equivalent (e.g., with a similar side chain, e.g., conserved amino acid substitutions) amino acid residues or nucleotides to a second amino acid or nucleic acid sequence such that the first and second amino acid or nucleic acid sequences have (or encode proteins having) similar activities, e.g., a binding activity, a binding preference, or a biological activity. In the case of antibodies, the second antibody has the same specificity and has at least 50% of the affinity relative to the same antigen.

Sequences similar or homologous (e.g., at least about 85% sequence identity) to the sequences disclosed herein are also part of this application. In some embodiment, the sequence identity can be about 85%, 90%, 91%, 92%, 93%, 94%, 95%, 96%, 97%, 98%, 99% or higher. In addition, substantial identity exists, e.g., when the nucleic acid segments hybridize under selective hybridization conditions (e.g., highly stringent hybridization conditions), to the complement of the strand. The nucleic acids may be present in whole cells, in a cell lysate, or in a partially purified or substantially pure form.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified. The invention includes nucleic acids that hybridize with low, medium, high, or very high stringency to a nucleic acid described herein or to a complement thereof, e.g., nucleic acids encoding a binding protein described herein. The nucleic acids can be the same length or within 30, 20, or 10% of the length of the reference nucleic acid. The nucleic acid can correspond to a region encoding an immunoglobulin variable domain sequence.

An integrin binding protein may have mutations relative to a binding protein described herein (e.g., a conservative or non-essential amino acid substitutions), which do not have a substantial effect on the protein functions. Whether or not a particular substitution will be tolerated, i.e., will not adversely affect biological properties, such as binding activity can be predicted, e.g., using the method of Bowie, et al. (1990) *Science* 247:1306-1310.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). It is possible for many framework and CDR amino acid residues to include one or more conservative substitutions.

Consensus sequences for biopolymers can include positions which can be varied among various amino acids. For example, the symbol "X" in such a context generally refers to any amino acid (e.g., any of the twenty natural amino acids or any of the nineteen non-cysteine amino acids). Other allowed amino acids can also be indicated for example, using parentheses and slashes. For example, "(A/W/F/N/Q)" means that alanine, tryptophan, phenylalanine, asparagine, and glutamine are allowed at that particular position.

A "non-essential" amino acid residue is a residue that can be altered from the wild-type sequence of the binding agent, e.g., the antibody, without abolishing or more preferably, without substantially altering a biological activity, whereas an "essential" amino acid residue results in such a change.

The terms "polypeptide" or "peptide" (which may be used interchangeably) refer to a polymer of three or more amino acids linked by a peptide bond, e.g., between 3 and 30, 12 and 60, or 30 and 300, or over 300 amino acids in length. The polypeptide may include one or more unnatural amino acids. Typically, the polypeptide includes only natural amino acids. A "protein" can include one or more polypeptide chains. Accordingly, the term "protein" encompasses polypeptides. A protein or polypeptide can also include one or more modifications, e.g., a glycosylation, amidation, phosphorylation, and so forth. The term "small peptide" can be used to describe a polypeptide that is between 3 and 30 amino acids in length, e.g., between 8 and 24 amino acids in length.

The term "cognate ligand" refers to a naturally occurring ligand of an integrin, including naturally occurring variants thereof (e.g., splice variants, naturally occurring mutants, and isoforms).

The term "mimic," in the context of a mimic of a conformation of an integrin or portion thereof, refers to a modified integrin which has a bias for at least one particular conformation relative to a naturally occurring integrin, or portion thereof.

Statistical significance can be determined by any art known method. Exemplary statistical tests include: the Students T-test, Mann Whitney U non-parametric test, and Wilcoxon non-parametric statistical test. Some statistically significant relationships have a P value of less than 0.05 or 0.02. Particular binding proteins may show a difference, e.g., in specificity or binding, that are statistically significant (e.g., P value <0.05 or 0.02). The terms "induce", "inhibit", "potentiate", "elevate", "increase", "decrease" or the like, e.g., which denote distinguishable qualitative or quantitative differences between two states, and may refer to a difference, e.g., a statistically significant difference, between the two states.

Other features and advantages of the instant invention will become more apparent from the following detailed description and claims. Embodiments of the invention can include any combination of features described herein. In no case does the term "embodiment" operate to exclude one or more other features disclosed herein, e.g., in another embodiment. The contents of all references, patent applications (published and unpublished) and published patents, cited throughout this application are hereby expressly incorporated by reference. This application also incorporates by reference the 2003 Food and Drug Administration (FDA)-approved product label for RAPTIVA®.

DETAILED DESCRIPTION

Figure 1:
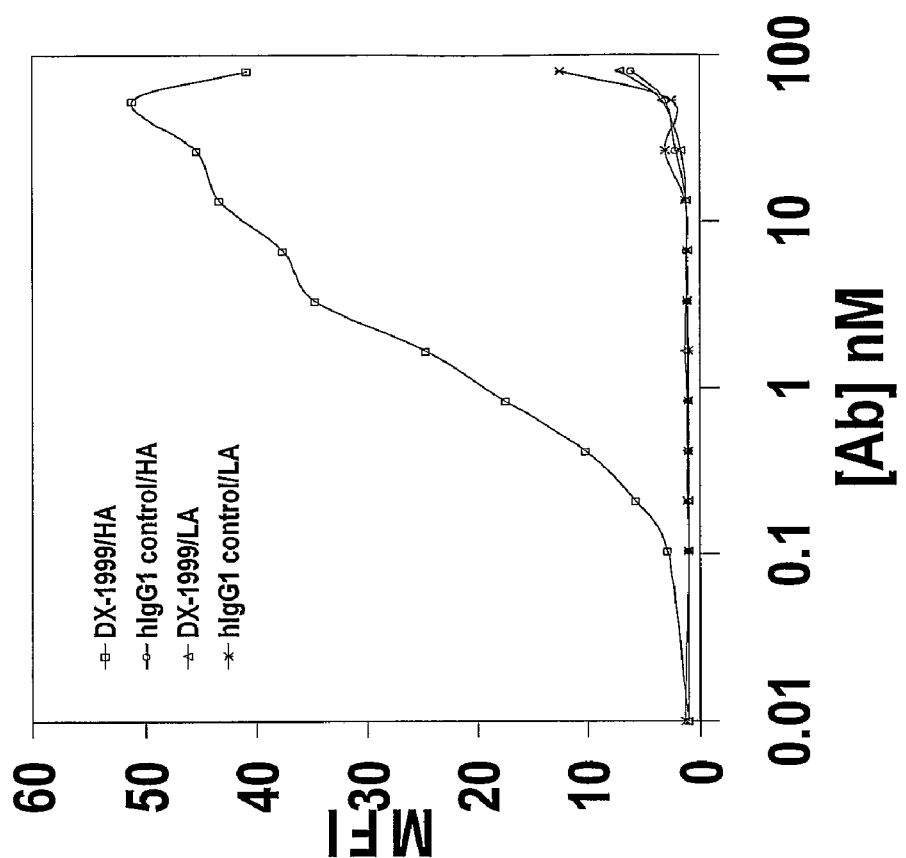
FIG. 1 is a graph from an exemplary experiment that evaluates DX-1999 (also known as D2-57) binding to HA cells (cells expressing an LFA-1 with an I-domain locked in the high affinity conformation) relative to LA cells (cells expressing an LFA-1 with an I-domain locked in the low affinity conformation).

This disclosure provides, inter alia, binding proteins (e.g., antibodies) that bind to an integrin in an activated conformation, e.g., activated LFA-1 ("aLFA-1"), e.g., relative to a non-activated conformation of LFA-1. In one embodiment, the binding proteins inhibit at least one function of an aLFA-1, e.g., inhibit a binding interaction between aLFA-1 and a cognate ligand of aLFA-1, e.g., an ICAM protein. The binding proteins can be used to treat or prevent an inflammatory disorder or other disorder described herein.

LFA1

Lymphocyte function-associated antigen-1 (LFA-1) is a member of the leukocyte integrin subfamily. LFA-1 is a heterodimer of an integrin alpha subunit, αL (CD11a), and a beta subunit β2 (CD18).

Other integrins of the leukocyte integrin subfamily also include the β2 subunit (CD18), but have distinct alpha subunits. For example, MAC-1 is a heterodimer of β2 and αM (CD11b). p150.95 is a heterodimer of β2 and αX (CD11c). Springer, T A (1990) *Nature* 346:425-433; Larson, R S and Springer T A, (1990) *Immunol Rev* 114:181-217; Van der Vieren, M et al. (1995) *Immunity* 3:683-690. The leukocyte integrins mediate a wide range of adhesive interactions that are essential for normal immune and inflammatory responses. LFA-1 binding to its cognate ligand can result in conformational changes to LFA-1 with significant cellular effects. LFA-1 functions that are mediated by clustering alone appear to be secondary to those mediated by ligand binding. See, e.g., Kim et al. (2004) *J. Cell Biol.* 167:1241.

An exemplary amino acid sequence of the α subunit of human LFA-1 (αL or CD11a) is as follows (gi|4504757|ref|NP_002200.1|):

```
                                        (SEQ ID NO: 30)
MKDSCITVMAMALLSGFFFFAPASSYNLDVRGARSFSPPRAGRHFGYRVL

QVGNGVIVGAPGEGNSTGSLYQCQSGTGHCLPVTLRGSNYTSKYLGMTLA

TDPTDGSILACDPGLSRTCDQNTYLSGLCYLFRQNLQGPMLQGRPGFQEC

IKGNVDLVFLFDGSMSLQPDEFQKILDFMKDVMKKLSNTSYQFAAVQFST

SYKTEFDFSDYVKWKDPDALLKHVKHMLLLTNTFGAINYVATEVFREELG

ARPDATKVLIIITDGEATDSGNIDAAKDITRYIIGIGKHFQTKESQETLH

KFASKPASEFVKILDTFEKLKDLFTELQKKIYVIEGTSKQDLTSFNMELS

SSGISADLSRGHAVVGAVGAKDWAGGFLDLKADLQDDTFIGNEPLTPEVR

AGYLGYTVTWLPSRQKTSLLASGAPRYQHMGRVLLFQEPQGGGHWSQVQT

IHGTQIGSYFGGELCGVDVDQDGETELLLIGAPLFYGEQRGGRVFIYQRR

QLGFEEVSELQGDPGYPLGRFGEAITALTDINGDGLVDVAVGAPLEEQGA

VYIFNGRHGGLSPQPSQRIEGTQVLSGIQWFGRSIHGVKDLEGDGLADVA

VGAESQMIVLSSRPVVDMVTLMSFSPAEIPVHEVECSYSTSNKMKEGVNI

TICFQIKSLYPQFQGRLVANLTYTLQLDGHRTRRRGLFPGGRHELRRNIA

VTTSMSCTDFSFHFPVCVQDLISPINVSLNFSLWEEEGTPRDQRAQGKDI

PPILRPSLHSETWEIPFEKNCGEDKKCEANLRVSFSPARSRALRLTAFAS

LSVELSLSNLEEDAYWVQLDLHFPPGLSFRKVEMLKPHSQIPVSCEELPE

ESRLLSRALSCNVSSPIFKAGHSVALQMMFNTLVNSSWGDSVELHANVTC

NNEDSDLLEDNSATTIIPILYPINILIQDQEDSTLYVSFTPKGPKIHQVK

HMYQVRIQPSIHDHNIPTLEAVVGVPQPPSEGPITHQWSVQMEPPVPCHY

EDLERLPDAAEPCLPGALFRCPVVFRQEILVQVIGTLELVGEIEASSMFS

LCSSLSISFNSSKHFHLYGSNASLAQVVMKVDVVYEKQMLYLYVLSGIGG

LLLLLLIFIVLYKVGFFKRNLKEKMEAGRGVPNGIPAEDSEQLASGQEAG

DPGCLKPLHEKDSESGGGKD.
```

An exemplary amino acid sequence of the β subunit of human LFA-1 (β2) is as follows (gi|4557886|ref|NP_000202.1|):

```
                                        (SEQ ID NO: 31)
MLGLRPPLLALVGLLSLGCVLSQECTKFKVSSCRECIESGPGCTWCQKLN

FTGPGDPDSIRCDTRPQLLMRGCAADDIMDPTSLAETQEDHNGGQKQLSP

QKVTLYLRPGQAAAFNVTFRRAKGYPIDLYYLMDLSYSMLDDLRNVKKLG

GDLLRALNEITESGRIGFGSFVDKTVLPFVNTHPDKLRNPCPNKEKECQP

PFAFRHVLKLTNNSNQFQTEVGKQLISGNLDAPEGGLDAMMQVAACPEEI

GWRNVTRLLVFATDDGFHFAGDGKLGAILTPNDGRCHLEDNLYKRSNEFD

YPSVGQLAHKLAENNIQPIFAVTSRMVKTYEKLTEIIPKSAVGELSEDSS

NVVHLIKNAYNKLSSRVFLDHNALPDTLKVTYDSFCSNGVTHRNQPRGDC

DGVQINVPITFQVKVTATECIQEQSFVIRALGFTDIVTVQVLPQCECRCR

DQSRDRSLCHGKGFLECGICRCDTGYIGKNCECQTQGRSSQELEGSCRKD

NNSIICSGLGDCVCGQCLCHTSDVPGKLIYGQYCECDTINCERYNGQVCG

GPGRGLCFCGKCRCHPGFEGSACQCERTTEGCLNPRRVECSGRGRCRCNV

CECHSGYQLPLCQECPGCPSPCGKYISCAECLKFEKGPFGKNCSAACPGL

QLSNNPVKGRTCKERDSEGCWVAYTLEQQDGMDRYLIYVDESRECVAGPN

IAAIVGGTVAGIVLIGILLLVIWKALIHLSDLREYRRFEKEKLKSQWNND

NPLFKSATTTVMNPKFAES.
```

Proteins that preferentially bind to an activated leukocyte integrin can be used to modulate a leukocyte activity and a physiological activity mediated by a leukocyte, e.g., an activated leukocyte. Such binding proteins can be used to modulate (e.g., inhibit) leukocyte migration, leukocyte adherence, or inflammation.

Integrins can adopt a plurality of conformations, including an activated and a non-activated conformation. Additional conformational intermediates are also available. The conformation of an integrin can be biased, for example, by modifying the amino acid sequence of the integrin. A bias in conformation can be introduce within a single domain of an integrin, e.g., within an integrin I-domain, a β-propeller domain, or between domains, or between subunits. In one embodiment, the integrin is modified by the engineering of an intra-molecular or inter-molecular disulfide bond. Modified integrin molecules can be used as mimics of a conformation of a naturally occurring integrin.

The N-terminal region of the integrin α subunits contains seven repeats of about 60 amino acids each, and has been predicted to fold into a 7-bladed β-propeller domain (Springer, T A (1997) *Proc Natl Acad Sci USA* 94:65-72).

The leukocyte integrin α subunits (such as the α1, α2, α10, α11, αL, αM, αD, αX, and αE subunits) contain an inserted domain or I-domain of about 200 amino acids (Larson, R S et al. (1989) *J Cell Biol* 108:703-712; Takada, Y et al. (1989) *EMBO J* 8:1361-1368; Briesewitz, R et al. (1993) *J Biol Chem* 268:2989-2996; Shaw, S K et al. (1994) *J Biol Chem* 269:6016-6025; Camper, L et al. (1998) *J Biol Chem* 273: 20383-20389). The I-domain is predicted to be inserted between β-sheets 2 and 3 of the β-propeller domain. The three dimensional structure of the αM, αL, α1 and α2 I-domains has been solved and shows that it adopts the dinucleotide-binding fold with a unique divalent cation coordination site designated the metal ion-dependent adhesion site (MIDAS) (Lee, J-O, et al. (1995) *Structure* 3:1333-1340; Lee, J-O, et al. (199S) *Cell* 80:631-638; Qu, A and Leahy, D J (1995) *Proc Natl Acad Sci USA* 92:10277-10281; Qu, A and Leahy, D J (1996) *Structure* 4:931-942; Emsley, J et al. (1997) *J Biol Chem* 272:28512-28517; Baldwin, E T et al. (1998) *Structure* 6:923-935; Kallen, J et al. (1999) *J Mol Biol* 292:1-9). The C-terminal region of the αM subunit has been predicted to fold into a β-sandwich structure (Lu, C et al. (1998) *J Biol Chem* 273:15138-15147).

US 2002-0123614 describes, inter alia, exemplary methods for obtaining and using conformationally biased integrin molecules. In one embodiment, an integrin is locked in a particular conformation using a disulfide bond. Computational algorithms for designing and/or modeling protein conformations are described, for example, in WO 98/47089. The SSBOND program (Hazes, B and Dijkstra, B W (1988) *Protein Engineering* 2:119-125) can be used to identify positions where disulfide bonds can be introduced in a protein structure by mutating appropriately positioned pairs of residues to cysteine.

Disulfide bond formation can occur between two cysteine residues that are appropriately positioned within the three-dimensional structure of a protein. Accordingly, a protein can be stabilized in a desired conformation by introducing at least one cysteine substitution into the amino acid sequence such that a disulfide bond is formed. The introduction of a single cysteine substitution is performed in circumstances in which an additional cysteine residue is present in the native amino acid sequence of the protein at an appropriate position such that a disulfide bond is formed. More commonly, two cysteine substitutions are introduced into the amino acid sequence of the protein at positions that allow a disulfide bond to form, thereby stabilizing the protein in a desired conformation. In another embodiment, the distance between the Cβ carbons of the residues that are substituted for cysteine is 3.00-8.09 Å. In yet another embodiment, the distance between the Cβ carbons in the disulfide bond is in the range of 3.41-7.08 Å.

Typically, cysteine substitutions are introduced such that the formation of a disulfide bond is favored only in one protein conformation, such that the protein is stabilized in that particular conformation. Cysteine substitutions can be produced by mutagenesis of DNA encoding the polypeptides of interest (e.g., integrin polypeptides). For example, an isolated nucleic acid molecule encoding a modified integrin I-domain polypeptide can be created by introducing one or more nucleotide substitutions into the nucleotide sequence of an integrin gene such that one or more codons, e.g., cysteine codons, are introduced into the encoded protein. Mutations can be introduced into a nucleic acid sequence by standard techniques, such as site-directed mutagenesis and PCR-mediated mutagenesis.

Additional methods for obtaining and using integrins in a locked conformation are described, e.g., in Shimaoka, M et al. (2003) *Cell* 112,99-111; Shimaoka, M et al. (2002) *Annu. Rev. Biophys. Biomol. Struct.* 31, 485-516; and Shimaoka, M et al. (2001) *Proc Natl Acad Sci USA* 98:6009-6014. Luo et al. (2003) *Proc Natl Acad Sci USA*. 100(5):2403-8 describe a conformationally biased integrin in which a glycan moiety is used to alter conformational preference. Luo et al. *J Biol Chem*. 2003 December 16 (Epub ahead of print), PMID: 14681220, describe additional conformationally biased, e.g., disulfide locked conformations.

For example, a conformationally biased integrin can include a modified integrin I-domain that is biased towards (e.g., locked in) the open conformation or a closed conformation. The open conformation may bind to a cognate ligand of the integrin with high affinity.

A disulfide locked molecule can be produced from a nucleic acid sequence that includes at least one codon substitution that inserts one or more (e.g., two) cysteine codons. The codons can be positions such that in the encoded protein, the distance between the Cβ carbons of the residues that are substituted for cysteines is in the range of 3.00-8.09 Angstroms e.g., as predicted by protein modeling. In a further embodiment, the distance between the Cβ carbons in the disulfide bond is in the range of 3.41-7.08 Angstroms.

Examples of integrin I-domains that are conformationally biased towards a particular conformation, e.g., an active "open" conformation, or a non-activated "closed" conformation include the following. The αL K287C/K294C, E284C/E301C, L161C/F299C, K160C/F299C, L161C/T300C, and L289C/K294C mutants, and the αM Q163C/Q309C and D294C/Q313C mutants are stabilized in "open" conformations that bind the cognate ligand with high or intermediate affinity, whereas the αL L289C/K294C mutant and the αM Q163C/R313C mutants are stabilized in non-activated "closed" conformations that do not bind to the cognate ligand. The affinity of E284C/E301C for the cognate ligand is nearly comparable to that of K287C/K294C, e.g., high-affinity. The affinity of L161C/F299C, K160C/F299C, and L161C/T300C for the cognate ligand are significantly higher than wild-type, but 20-30 times lower than high-affinity αL I-domain, K287C/K294C. L161C/F299C, K160C/F299C, and L161C/T300C are referred to herein as intermediate affinity αL I-domains.

The I-domain of αL is described as follows, with secondary structure information below:

```
                                                    (SEQ ID NO: 32)
  1  GNVTDLVFLF DGSMSLQPDE FQKILDFMKD VMKKLSNTSY QFAAVQFSTS
        EEEEEEE E  BTTS HHH  HHHHHHHHHH HHHHTTTSSE EEEEEEESSS

50  YKTEFDFSDY VKRKDPDALL KHVKHMLLLT NTFGAINYVA TEVFREELGA
        EEESB HHHH HHHTTHHHHT SB      B     HHHHHHHHHH HHTTTGGGT

100  RPDATKVLII ITDGEATDSG NIDAAKDIIR YIIGIGKHFQ TKESQETLHK
        TTSEEEEEE EE S     S        GGGTTSEE EEEE SS      STTTGGGGTT

150  FASKPASEFV KILDTFEKLK DLFTELQKKI
        TS SSHHHHE EETTTTTTTT TTT
```

See, e.g., PDB™ structures: (1) 1MQA "Crystal Structure Of High Affinity Alpha-1 I Domain In The Absence Of Ligand Or Metal" (mmdbId:21776); (2) 1MQ9 "Crystal Structure Of High Affinity Alpha-1 I Domain With Ligand Mimetic Crystal Contact" (mmdbId:21775); (3) 1MQ8 "Crystal Structure Of Alpha-1 I Domain In Complex With Icam-1" (mmdbId:21774); and (4) 1MJN "Crystal Structure Of The Intermediate Affinity A1 I Domain Mutant" (mmdbId: 21755).

Conformationally biased integrin molecules may include just a modified integrin I-domain from an integrin α subunit, or the entire mature α subunit extracellular domain, or the entire mature α subunit, and/or may be further associated with an integrin β subunit extracellular domain and/or entire subunit. In one embodiment, a modified integrin I-domain polypeptide is a soluble protein, e.g., a heterodimeric soluble protein, or a monomeric soluble protein.

A model of the I-like domain of the integrin β-subunit that is supported by experimental data (Huang, C et al. (2000) J Biol Chem 275:21514-24) has also been made. The data confirm the location of the key C-terminal α-helix that undergoes the dramatic 10 Angstrom conformational movement in I-domains. The I and I-like domains align well in this region.

Identification of aLFA-1 Binding Proteins

A number of methods can be used to identify proteins that bind to aLFA-1 and other active integrins. Many of these methods use conformationally-biased integrin proteins as targets.

One exemplary method for identifying antibodies that bind to aLFA-1 includes immunizing a non-human animal with a conformationally biased LFA-1 protein or a conformationally biased domain thereof. Spleen cells can be isolated from the immunized animal and used to produce hybridoma cells using standard methods. In one embodiment, the non-human animal includes one or more human immunoglobulin genes.

Another exemplary method for identifying proteins that bind to aLFA-1 includes: providing a library of proteins and selecting from the library one or more proteins that bind to a conformationally biased molecule, e.g., a conformationally biased integrin, e.g., aLFA-1. The selection can be performed in a number of ways. For example, the library can be provided in the format of a display library or a protein array. Prior to selecting, the library can be pre-screened (e.g., depleted) to remove members that interact with a non-target molecule, e.g., an LFA-1 molecule in the non-activated conformation.

The conformationally biased target molecule can be tagged and recombinantly expressed. In one embodiment, the conformationally biased target molecule is purified and attached to a support, e.g., to affinity beads, or paramagnetic beads or other magnetically responsive particles.

A conformationally biased target molecule can also be expressed on the surface of a cell. Members of the display library that specifically bind to the cell can be selected. It is also possible to use an endogenous or other wild-type form of an integrin. For example, members of the display library that specifically bind to a cell, only if the integrin is activated, can be selected.

Expression Libraries

In one embodiment, a display library or other expression library is used to identify proteins that bind to an integrin in an activated conformation, e.g., aLFA-1. A display library is a collection of entities; each entity includes an accessible protein component (e.g., a Fab or scFv) and a recoverable component (e.g., a nucleic acid) that encodes or identifies the protein component. The protein component can be of any length, e.g. from three amino acids to over 300 amino acids. In a selection, the protein component of each member of the library is probed with a conformationally biased integrin protein and if the protein component binds to the protein, the display library member is identified, e.g., by retention on a support. The protein component can include one or more immunoglobulin variable domains or variants of another domain. Methods for making libraries of immunoglobulin domains are well known. See, e.g., U.S. Application Ser. No. 60/546,354, filed on Feb. 19, 2004, US 2004-0005709, and US 2002-0102613.

Retained display library members are recovered from the support and analyzed. The analysis can include amplification and a subsequent selection under similar or dissimilar conditions. For example, positive and negative selections can be alternated. The analysis can also include determining the amino acid sequence of the protein component and purification of the protein component for detailed characterization.

A variety of formats can be used for display libraries. Examples include the following.

Phage Display. One format utilizes viruses, particularly bacteriophages. This format is termed "phage display." The protein component is typically covalently linked to a bacteriophage coat protein. The linkage results from translation of a nucleic acid encoding the protein component fused to the coat protein. The linkage can include a flexible peptide linker, a protease site, or an amino acid incorporated as a result of suppression of a stop codon. Phage display is described, for example, in U.S. Pat. No. 5,223,409; Smith (1985) Science 228:1315-1317; WO 92/18619; WO 91/17271; WO 92/20791; WO 92/15679; WO 93/01288; WO 92/01047; WO 92/09690; WO 90/02809; de Haard et al. (1999) J. Biol. Chem. 274:18218-30; Hoogenboom et al. (1998) Immunotechnology 4:1-20; and Hoogenboom et al. (2000) Immunol Today 2:371-8.

Phage display systems have been developed for filamentous phage (phage f1, fd, and M13) as well as other bacteriophage. The filamentous phage display systems typically use fusions to a minor coat protein, such as gene III, to present the protein component on the surface of the bacteriophage. It is also possible to physically associate the protein being displayed to the coat using a non-peptide linkage.

Bacteriophage displaying the protein component can be grown and harvested using standard phage preparatory methods, e.g. PEG precipitation from growth media. After selection of individual display phages, the nucleic acid encoding the selected protein components can be isolated from cells infected with the selected phages or from the phage themselves, after amplification. Individual colonies or plaques can be picked, the nucleic acid isolated and sequenced.

Other Display Formats. Other display formats include cell based display (see, e.g., WO 03/029456), protein-nucleic acid fusions (see, e.g., U.S. Pat. No. 6,207,446), and ribosome display (See, e.g., Matthealkis et al. (1994) Proc. Natl. Acad. Sci. USA 91:9022 and Hanes et al. (2000) Nat. Biotechnol. 18:1287-92; Hanes et al. (2000) Methods Enzymol. 328:404-30; and Schaffitzel et al. (1999) J Immunol Methods. 231(1-2):119-35).

Epitope Specific Binding proteins. Display technology can also be used to obtain binding proteins, e.g., antibodies, that bind to particular epitopes of a target. Epitopes can be classified as "conformational" or "sequential". Conformational epitopes involve amino-acid residues that have a defined relative orientation in a properly folded target even though the amino acids may be substantially separated in the sequence (e.g., separated by at least one, two, four, six, eight or ten amino acids). Sequential epitopes involve short portions of the polypeptide chain that bind an antibody whatever the folding state of the protein (e.g., native or unfolded). Binding proteins for conformational epitopes can be identified, for example, by using competing non-target molecules that lack the particular epitope or are mutated within the epitope, e.g., with alanine. Such non-target molecules can be used in a negative selection procedure as described below, as competing molecules when binding a display library to the target, or as a pre-elution agent, e.g., to capture in a wash solution dissociating display library members that are not specific to the target. In another implementation, epitope specific binding proteins are identified by eluting display library members with a competing binding protein that binds to the epitope of interest on the target molecule. Binding proteins that bind sequential epitopes can be selected, for example, using short peptides that have amino-acid sequences found in a target protein. Often binding proteins that bind to conformational epitopes also bind weakly to one or another peptide that contains some of the amino acids involved in the conformational epitope. Thus, one can select for binding to a peptide at very low stringency and then select for binding to the folded target protein.

Affinity Maturation. In one embodiment, a binding protein that binds to a target is modified, e.g., by mutagenesis, to provide a pool of modified binding proteins. The modified binding proteins are then evaluated to identify one or more altered binding proteins which have altered functional properties (e.g., improved binding, improved stability, lengthened stability in vivo). In one implementation, display library technology is used to select or screen the pool of modified binding proteins. Higher affinity binding proteins are then identified from the second library, e.g., by using higher stringency or more competitive binding and washing conditions. Other screening techniques can also be used.

In some implementations, the mutagenesis is targeted to regions known or likely to be at the binding interface. If, for example, the identified binding proteins are antibodies, then mutagenesis can be directed to the CDR regions of the heavy or light chains as described herein. Further, mutagenesis can be directed to framework regions near or adjacent to the CDRs, e.g., framework regions, particular within ten, five, or three amino acids of a CDR junction. In the case of antibodies, mutagenesis can also be limited to one or a few of the CDRs, e.g., to make step-wise improvements.

In one embodiment, mutagenesis is used to make an antibody more similar to one or more germline sequences. One exemplary germlining method can include: identifying one or more germline sequences that are similar (e.g., most similar in a particular database) to the sequence of the isolated antibody. Then mutations (at the amino acid level) can be made in the isolated antibody, either incrementally, in combination, or both. For example, a nucleic acid library that includes sequences encoding some or all possible germline mutations is made. The mutated antibodies are then evaluated, e.g., to identify an antibody that has one or more additional germline residues relative to the isolated antibody and that is still useful (e.g., has a functional activity). In one embodiment, as many germline residues are introduced into an isolated antibody as possible.

In one embodiment, mutagenesis is used to substitute or insert one or more germline residues into a CDR region. For example, the germline CDR residue can be from a germline sequence that is similar (e.g., most similar) to the variable region being modified. After mutagenesis, activity (e.g., binding or other functional activity) of the antibody can be evaluated to determine if the germline residue or residues are tolerated. Similar mutagenesis can be performed in the framework regions.

Selecting a germline sequence can be performed in different ways. For example, a germline sequence can be selected if it meets a predetermined criteria for selectivity or similarity, e.g., at least a certain percentage identity, e.g., at least 75, 80, 85, 90, 91, 92, 93, 94, 95, 96, 97, 98, 99, or 99.5% identity. The selection can be performed using at least 2, 3, 5, or 10 germline sequences. In the case of CDR1 and CDR2, identifying a similar germline sequence can include selecting one such sequence. In the case of CDR3, identifying a similar germline sequence can include selecting one such sequence, but may including using two germline sequences that separately contribute to the amino-terminal portion and the carboxy-terminal portion. In other implementations more than one or two germline sequences are used, e.g., to form a consensus sequence.

In one embodiment, with respect to a particular reference variable domain sequence, e.g., a sequence described herein, a related variable domain sequence has at least 30, 40, 50, 60, 70, 80, 90, 95 or 100% of the CDR amino acid positions that are not identical to residues in the reference CDR sequences, residues that are identical to residues at corresponding positions in a human germline sequence (i.e., an amino acid sequence encoded by a human germline nucleic acid).

In one embodiment, with respect to a particular reference variable domain sequence, e.g., a sequence described herein, a related variable domain sequence has at least 30, 50, 60, 70, 80, 90 or 100% of the FR regions are identical to FR sequence from a human germline sequence, e.g., a germline sequence related to the reference variable domain sequence.

Accordingly, it is possible to isolate an antibody which has similar activity to a given antibody of interest, but is more similar to one or more germline sequences, particularly one or more human germline sequences. For example, an antibody can be at least 90, 91, 92, 93, 94, 95, 96, 97, 98, 99, 99.5% identical to a germline sequence in a region outside the CDRs (e.g., framework regions). Further an antibody can include at least 1, 2, 3, 4, or 5 germline residues in a CDR region, the germline residue being from a germline sequence of similar (e.g., most similar) to the variable region being modified. Germline sequences of primary interest are human germline sequences. The activity of the antibody (e.g., the binding activity) can be within a factor or 100, 10, 5, 2, 0.5, 0.1, and 0.001 of the original antibody. An exemplary germline sequences include VKI-O2, VL2-1, VKIII-L2::JK2, vg3-23, V3-23::JH4, and V3-23::JK6.

Some exemplary mutagenesis techniques include: error-prone PCR (Leung et al. (1989) *Technique* 1:11-15), recombination (see, e.g., U.S. Ser. No. 10/279,633), DNA shuffling using random cleavage (Stemmer (1994) *Nature* 389-391; termed "nucleic acid shuffling"), RACHITT™ (Coco et al. (2001) *Nature Biotech.* 19:354), site-directed mutagenesis (Zoller et al. (1987) *Nucl Acids Res* 10:6487-6504), cassette mutagenesis (Reidhaar-Olson (1991) *Methods Enzymol.* 208: 564-586) and incorporation of degenerate oligonucleotides (Griffiths et al. (1994) *EMBO J.* 13:3245).

In one example of affinity maturation the methods described herein are used to first identify a binding protein from a display library that binds an aLFA-1 with at least a minimal binding specificity for a target or a minimal activity, e.g., an equilibrium dissociation constant for binding of less than 1 nM, 10 nM, or 100 nM. The nucleic acid sequence encoding the initial identified binding protein are used as a template nucleic acid for the introduction of variations, e.g., to identify a second binding protein that has enhanced properties (e.g., binding affinity, kinetics, or stability) relative to the initial binding protein. Alternatively, the amino-acid sequence of one or more CDRs can be used as a guide for design of a nucleic acid library that includes nucleic acids encoding the isolated sequence and many neighboring sequences. Such diversified nucleic acids can be introduced into a display vector containing the initial isolate and improved variants are selected from the library.

Off-Rate Selection. Since a slow dissociation rate can be predictive of high affinity, particularly with respect to interactions between polypeptides and their targets, the methods described herein can be used to isolate binding proteins with a desired kinetic dissociation rate (i.e. reduced) for a binding interaction to a target.

To select for slow dissociating binding proteins from a display library, the library is contacted to an immobilized target. The immobilized target is then washed with a first solution that removes non-specifically or weakly bound biomolecules. Then the immobilized target is eluted with a second solution that includes a saturation amount of free target, i.e., replicates of the target that are not attached to the particle. The free target binds to biomolecules that dissociate from the target. Rebinding is effectively prevented by the saturating amount of free target relative to the much lower concentration of immobilized target.

The second solution can have solution conditions that are substantially physiological or that are stringent. Typically, the solution conditions of the second solution are identical to the solution conditions of the first solution. Fractions of the second solution are collected in temporal order to distinguish early from late fractions. Later fractions include biomolecules that dissociate at a slower rate from the target than biomolecules in the early fractions.

Further, it is also possible to recover display library members that remain bound to the target even after extended incubation. These can either be dissociated using chaotropic conditions or can be amplified while attached to the target. For example, phage bound to the target can be contacted to bacterial cells.

Selecting and Screening for Specificity. "Selection", in the context of a display library, refers to a process in which many members of a display library are allowed to contact the target and those that bind are recovered and propagated. The selection can be from a library having numerous members, e.g., more than $10^{10}$ members. "Screening", in the context of a display library, refers to a process in which isolated members of the library are tested singly for binding to the target. Through automation, thousands of candidates may be screened in a highly parallel process. The display library selection methods described herein can include a selection process that discards display library members that bind to a non-target molecule.

Examples of non-target molecules, e.g., for an LFA-1 binding antibody, include, e.g., integrins other than LFA-1. In another example, for an aLFA-1 binding antibody, e.g., an antibody that preferentially binds to activated LFA-1, the non-target molecule can be an LFA-1 molecule in a conformation other than activated, e.g., a non-activated conformation.

In one implementation, a so-called "negative selection" step is used to discriminate between the target and related non-target molecule and a related, but distinct non-target molecule. The display library or a pool thereof is contacted to the non-target molecule. Members of the sample that do not bind the non-target are collected and used in subsequent selections for binding to the target molecule or even for subsequent negative selections. The negative selection step can be prior to or after selecting library members that bind to the target molecule.

In another implementation, a screening step is used. After display library members are isolated for binding to the target molecule, each isolated library member is tested for its ability to bind to a non-target molecule (e.g., a non-target listed above). For example, a high-throughput ELISA screen can be used to obtain this data. The ELISA screen can also be used to obtain quantitative data for binding of each library member to the target. The non-target and target binding data are compared (e.g., using a computer and software) to identify library members that specifically bind to aLFA-1.

The display library selection and screening methods described herein can include a selection or screening process that selects for display library members that bind to specific sites on the target molecule. For example, elution with high concentration of an antibody described herein selects for phage that bind to the epitope bound by such an antibody. One can screen for a phage that binds to a particular epitope of aLFA-1 by performing ELISAs with and without a competing antibody that recognizes the epitope in the buffer.

Secondary Screening Methods

Display libraries can be used to select candidate display library members that bind to the target. Each such candidate library member or any candidate aLFA-1 binding protein can be further analyzed, e.g., to further characterize its binding properties for the target. Each candidate display library member can be subjected to one or more secondary screening assays. The assay can be for a binding property, a physiological property (e.g., cytotoxicity, renal clearance, immunogenicity), a structural property (e.g., stability, conformation, oligomerization state) or another functional property (e.g. ability to modulate an activity of an integrin-expressing cell, e.g., a leukocyte, or ability to modulate inflammation or an inflammation associated-response). The same assay can be used repeatedly, but with varying conditions, e.g., to determine pH, ionic, or thermal sensitivities.

As appropriate, the assays can use the display library member directly, a recombinant polypeptide produced from the nucleic acid encoding a displayed polypeptide, a synthetic peptide synthesized based on the sequence of a displayed polypeptide. In the case of a candidate aLFA-1 binding protein from any source, the protein can be obtained, e.g., from such a source or by recombinant production. Exemplary assays for binding properties include the following.

Exemplary Biological Assays

Candidate aLFA-1 binding proteins can be evaluated for their activity in vitro (e.g., in a cell-free or cell-based system) or in vivo (e.g., in an animal model describe below). For example, the proteins can be evaluated for their ability to inhibit an activity of LFA-1 expressing cells, e.g., a binding activity of an LFA-1 expressing cell. In another example, the proteins can be evaluated for their ability to target cells that present activated LFA-1.

The binding of LFA-1 expressing cells to a cognate ligand can be evaluated, e.g., using cellular assays. ICAM-1 is expressed, e.g., on leukocytes, endothelium, and dermal fibroblasts (Dustin et al., J. Immunol. 137: 245-254 (1986)), ICAM-2 expressed on resting endothelium and lymphocytes (de Fougerolles et al., J. Exp. Med. 174: 253-267 (1991)), and ICAM-3 expressed on monocytes and resting lymphocytes (de Fougerolles et al., J. Exp. Med. 179: 619-629 (1994)). Accordingly, cell adhesion assays (e.g., using fluorescently labeled cells) can be performed between LFA-1 expressing cells and other leukocytes, endothelial cells, monocytes, and dermal fibroblasts.

Another exemplary assay for ICAM binding is as follows: ICAM-1 is purified from human tonsil, and coated on 96-well plates as described previously (Lu and Springer, (1997) *J Immunol* 159:268-278). LFA-1 expressing cells are labeled with a florescence dye 2',7'-bis-(carboxyethyl)-5(and-6)-carboxyfluorescein, acetoxymethyl ester (BCECF-AM), and resuspended at about $1 \cdot 10^6$/ml in L15/FBS. 50 µl of cell suspension is mixed in ICAM-1 coated wells with an equal volume of L15/FBS in the absence or presence of a test compound (e.g., a candidate aLFA-1 binding protein). The assays can be performed in the presence and absence of an activating monoclonal antibody (CBRLFA-½, 10 µg/ml).

For testing the effect of divalent cations, BCECF-AM-labeled cells are washed twice with TS buffer, pH7.5 (20 mM Tris, pH 7.5, 150 mM NaCl) containing 5 mM EDTA, followed by two washes with TS buffer, pH7.5. Cells were then resuspended to $5 \cdot 10^5$/ml in the TS buffer, pH7.5 supplemented with 1 mM $MgCl_2$ and other divalent cations and 2 mM EDTA. 100 µl of the cell suspension is added to ICAM-1 coated wells. After incubation at 37° C. for 30 minutes, unbound cells are washed off on a Microplate AUTO-WASHER™ (Bio-Tek Instruments, Winooski, Vt.). The fluorescence content of total input cells and the bound cells in each well is quantitated on a Fluorescent Concentration Analyzer (IDEXX, Westbrook, Me.). The number of bound cells can be expressed as a percentage of total input cells per sample well.

The following exemplary assay evaluates the effect of a test compound (e.g., an aLFA-1 binding protein) on the ability of test compound to modulate cell-cell interactions that depend on LFA-1. The assay uses lymphoma cell line EL-4 which expresses both murine LFA-1 and ICAM-1, and which exhibits LFA-1-dependent homotypic aggregation upon activation by PMA. Cells are incubated in a 96 well plate in the presence of 50 ng/ml PMA and varying amounts of the test compound. After incubation for 2 hours at 37° C., 5% $CO_2$, the degree of aggregation was scored under the microscope as follows: 0 indicated that essentially no cells are clustered; 1 indicated that <10% of cells are aggregated; 2 indicated clustering of <50%; 3 indicated that up to 100% of cells were in small, loose aggregates; 4 indicated that nearly 100% of cells are in larger clusters; and 5 indicated that nearly 100% of cells are in very large, tight clusters.

Still another exemplary assay evaluates the ability of a test compound to inhibit LFA-1 function in vivo. The assay includes visualizing microcirculation in the peripheral lymph node (LN) with intravital microscopy. Briefly, a small bolus (20-50 µl) of LN cell suspensions from TGFβ mice are retrogradely injected through a femoral artery catheter and visualized in the subiliac LN by fluorescent epi-illumination from a video-triggered xenon arc stroboscope. After recording control TGFβ cell behavior in the absence of test compound, the mouse was pretreated by intra-arterial injection of the test compound (e.g., at a desired concentration) 5 minutes before $TGF^{GFP}$ cell injection. Scenes can be recorded on videotape and off-line analysis was done. The rolling fraction can be calculated as percentage of the number rolling cells relative to the total number of TGFβ cells that entered a venule. The sticking (firm adhesion) fraction can be determined as the percentage of $T^{GFP}$ cells becoming firmly adherent for >20 seconds in the number of $T^{GFP}$ cells that rolled in a venule. Results can be semi-quantitatively scored as follows: –: 0%, .+–.: 0-5%, +; 5-20%, ++: 20-40%, +++: 40-60%, ++++: 60-80%, +++++:80-100%.

The vascular endothelium is a substrate with which monocytes/granulocytes can interact during adherence, diapedesis, and differentiation. An in vitro assay for monocyte/granulocyte interaction with the vessel wall consists of binding radiolabeled or fluorescein monocyte/granulocyte preparations to cultured vascular endothelium, as described in Arnaout et al., J. Cell Physiol. 137:305 (1988). Mentzer et al., J. Cell Physiol. 125:285 (1986) describes a lymphocyte adhesion assay. A granulocyte aggregation assay can be performed as described by Arnaout et al., New Engl. J. Med. 306:693 (1982). Aggregation can be induced by zymosan-activated autologous serum or with chemotactic peptides, e.g. FMLP. Aggregation can then be recorded as incremental change in light transmission using a platelet aggregometer. The results can be confirmed by phase microscopy. Chemotaxis can be evaluated, e.g., as described in Dana et al., J. Immunol. 137: 3259 (1986).

A protein (e.g., an antibody described herein) can also be evaluated in culture for ability to modulate inflammation or an inflammatory disorder. For example, cell culture is used to monitor adhesion of leukocytes. A compound can be immobilized on a solid surface and adhesion of cells expressing an adhesion molecule can be evaluated for interaction with the surface. Cells suitable for this assay include any leukocytes, such as T cells, B cells, monocytes, eosinophils, and basophils. Exemplary leukocyte cell lines include Jurkat and U937 cells.

In one embodiment, a protein (e.g., an antibody described herein) has a statistically significant effect in an assay described herein. An assay for a protein can be compared to corresponding control assay, as appropriate, e.g., an assay lacking one or more components, e.g., lacking the test compound, a particular cell, a particular antibody, cation, etc.

Animal Models

An aLFA-1 binding protein can be evaluated in an animal model, e.g., an animal model for an inflammatory disorder, a disorder characterized by excessive LFA-1 activity, or a LFA-1 mediated disorder.

A number of animal models for psoriasis are available. The efficacy of an integrin binding protein (e.g., an aLFA-1 binding antibody described herein) can be tested in an animal model of psoriasis, e.g., in a BNX transplanted psoriasis skin model, for example, the model described in Wrone-Smith et al. (1996) J Clin Invest. 98(8):1878-87. Additional examples include the following. Schon et al. (1997) *Nat. Med.* 3:183-8 describe a mouse having a murine psoriasis-like disorder. The mouse was created by reconstituting scid/scid mice with naive $CD4^+$ T cells. Other mouse models for psoriasis have also utilized immunodeficient animals. Sugai et al. (1998) *J Dermatol Sci* 17:85-92 transplanted human psoriatic lesions onto scid mice. Yamamoto et al. (1998) *J Dermatol Sci* 17:8-14 describe injecting staphylococcal enterotoxin B-stimulated lymphocytes subcutaneously under full-thickness psoriatic skin grafted onto severe combined immunodeficient (scid) mice. Sundberg et al. (1997) Pathobiology 65(5):271-86 describe the development and progression of psoriasiform dermatitis and systemic lesions in the flaky skin (fsn) mouse mutant. Flaky skin (fsn) mutant mice have been described as a mouse model for psoriasis accompanied by hematological abnormalities. Hong et al. (1999) J. Immunol. 162:7480-7491 describe additional animal models of psoriasis. U.S. Pat. No. 6,410,824 describes producing an animal model by transferring naive, immuno-competent T lymphocytes into an immunodeficient animal host, along with at least one pro-inflammatory cytokine and a polyclonal activating agent. The engrafted T cells are tolerant to the major histocompatibility antigens of the host animal, but are mismatched at one or more minor histocompatibility loci. The engrafted animals develop a chronic skin disorder that includes histological features observed in human psoriasis, e.g. rete pegs, severe acanthosis and infiltration of Th1 cells into the dermis.

U.S. Pat. No. 6,462,020 describes an exemplary mouse model for arthritis, the induced Type II Collagen Arthritis Mouse Model. The mouse model can be used to evaluate the effect of aLFA-1 binding proteins on the histological, radiographic and clinical appearance of induced type II collagen arthritis. The histopathology of arthritic lesions occurring in murine CIA share many similarities to that of rheumatoid arthritis (RA) in human patients. Murine CIA is a useful model to study potential therapeutic treatments of RA.

The following is an exemplary version of the murine CIA model. Materials and Methods: Mice: DBA/1(2) male mice weighing 25 g (Jackson Laboratories, Bar Harbor, Me. or B&K Universal, Kent Wash.) are used for this work. This strain of mouse is susceptible to CIA by the injection of heterologous type II collagen. Bovine Collagen (BC), Complete Freund's Adjuvant (CFA) and Incomplete Freund's Adjuvant (ICFA) can be obtained from Sigma Chemical. Antigen for immunization is processed in 0.1 M acetic acid and formulated with CFA or ICFA.

Induction of Arthritis. Immunization protocol: Mice are injected with 100 µg of type II collagen in CFA at predetermined intervals during the study period.

The mice are examined at predetermined intervals for the development of arthritis. Presumptive evidence of arthritis includes swelling and erythema of at least one toe joint on the front and/or rear feet on two consecutive observations.

Confirmatory Diagnosis of Arthritis. Histological Examination of joints: The toe joints of animals sacrificed at appropriate intervals are removed, fixed, decalcified, embedded, in paraffin, sectioned, and stained for observation of general cellular and structural features and to detect cartilaginous matrix of the pannus of each joint, as appropriate. The degree of cellularity and areas of inflammation are quantified by using digitization of histological photomicrographs and applying standard area and point counting techniques as described above.

Radiographic evaluation of toe joints is performed to detect the incidence of joint changes after immunization with type II collagen. A mammography imaging system has been modified for this work. The average area of soft tissue (pannus) of the joint is determined by analysis of computer digitized radiographs, along with changes in density of the adjacent hard tissues by comparison with internal standards included with each radiograph. To serve as a baseline control for the changing density of the hard tissues and areas of panni, additional mice are used over the same period and the density and area data compared. The significance of the differences in density and area for control and experimental mice is assessed using paired T-tests at each time point.

Arthritis Evaluation. Animals are observed daily for the onset of arthritis. An arthritis index is derived by grading the severity of involvement of each paw on a scale from 0 to 4. Scoring is based upon the degree of peri-articular erythema and edema, as well as deformity of the joints. Swelling of hind paws is also quantitated by measuring the thickness of the ankle from the medial to the lateral malledus with a constant tension caliper.

US 2003-0161810 provides a non-human animal model for an inflammatory disorder (including rheumatoid arthritis). The animal described therein includes human synovial fluid. US 2003-0176389 describes a dextran sodium sulfate-induced mouse model of colitis.

An aLFA-1 binding protein can be assayed for an effect on neutrophil migration. One model for neutrophil migration is murine thioglycollate induced peritonitis. Thioglycollate is injected i.p. to mice and immediately thereafter the protein to be tested is given, e.g., by i.p. or s.c. The mice are killed after 4 hours, the peritoneal cavity lavaged and the total number of neutrophils in the lavage fluid is determined.

An aLFA-1 binding protein can be assayed for an effect on ischemia/reperfusion injury. The protein can be tested, e.g., in a model of heart ischemia/reperfusion injury (Abdeslam Oubenaissa et al., Circulation, 94, Suppl. II, 254-258, 1996). The protein can also be tested as follows:

Mice are treated with an aLFA-1 binding protein or a control. Mice weighing 20-25 g are anaesthetized with isoflurane and the right renal vessels are clamped using microvascular clamps for 60 min. After 60 min of ischemia, the microvascular clamps are removed. The left renal vessels (renal artery, vein and urethra) are ligated using a 4-0 surgical suture. The left (non-ischemic) kidney is removed, and the abdominal cavity closed with 3-0 surgical suture. Control groups undergo the same procedures as the ischemia group, but without clamping of the right renal vessels.

Animals are sacrificed by $CO_2$ inhalation at 24 h, 1 week and 2 weeks following reperfusion. Blood samples are collected by cardiac puncture into a 3.0 ml VACUTAINER™ tube (Becton-Dickenson) containing 0.04 ml of a 7.5% solution of $K_3$ EDTA immediately after sacrifice. Plasma is separated and stored at −20° C. until further analysis. Plasma creatine and blood urea nitrogen (BUN) are analyzed. Following sacrifice, the kidney is flushed with physiological saline, immediately snap-frozen in liquid nitrogen and stored at −70° C. until analysis. Myeloperoxidase activity (MPO) in the kidney can be measured according to the method of Bradley et al (*J. Invest. Dermatol.*, 78, 206-209, 1982).

An aLFA-1 binding protein can be assayed for an effect on vascularized heterotopic heart transplantation. Recipient mice are treated with an aLFA-1 binding protein or a control. Mice donor hearts are implanted onto the recipients abdominal vessels: brachiocephalic trunk to aorta and right pulmonary artery to inferior vena cava with end-to-side anastomoses using 11/0 Ethilon (Ethicon, Norderstedt, Germany) continuous sutures. Animals are closed in two layers with 6/0 Vicryl (Ethicon) and kept warm until fully recovered. Total ischemia times are in the range of 40-50 min of which 25-35 min are at 4° C. During anastomosis (10-15 min) the graft is kept cold.

After transplantation, graft function is monitored by daily assessment of graft beat (palpation). Rejection is considered to be complete when heart beat stops. In all experiments rejection is confirmed by histological examination of the grafts.

An exemplary assay for reperfusion injury associated with myocardial infarction in dogs is described, e.g. in Simpson et al., *J. Clin. Invest.* 81:624 (1988). Takeshima et al., Stroke, 23(2):247-252 (1992) describe a transient focal cerebral ischemia model in cats. Takeshima et al. used a microvascular clip to occlude the MCA and occluded CCAs by tightening previously placed ligatures. Lindsberg et al. J. Neurosurg. 82:269-277 (1995) describe a rabbit model of severe spinal cord ischemia (by inflating the balloon of a catheter tip which had been introduced in the abdominal aorta). Still additional models include the reversible spinal cord model (involving a snare ligature occluding device) and an irreversible microsphere model. Clark et al., Stroke 22(7): 877-883 (1991).

Bowes et al., *Neurology* 45:815-819 (1995) evaluated the ability of particular antibodies to enhance the efficacy of thrombolysis in a rabbit cerebral embolism stroke model. In this model, numerous small blood clots (formed by fragmenting a clot with a tissue homogenizer) are injected into the rabbit's carotid circulation in order to achieve embolization.

Neurologic function in each animal can be evaluated 18 hours following embolization on a three point scale: (1) normal activity; (2) abnormal activity; or (3) death. The amount of clot necessary to produce permanent neurologic damage in 50% of the rabbits (ED.sub.50) is determined for each treatment group. Antibodies described herein can be evaluated using this or a similar model to evaluate efficacy of thrombolysis to prevent, treat, or otherwise ameliorate a stroke.

Bednar et al., Stroke 23(1):152 (1992) describe a rabbit model of thromboembolic stroke wherein the arterial occlusion (an autologous blood clot delivered to the anterior cerebral circulation) is not removed during the experiment. Rabbits received the binding protein (e.g., aLFA-1 binding antibody) or vehicle, 30 minutes following the thromboembolic event. Following embolization, the animals are evaluated for a total of 4 hours, including an initial 45 minutes of systemic hypotension.

An aLFA-1 binding protein can be assayed for an effect on asthma or another airway hyperresponsive disorder, e.g., using an animal model described in U.S. Pat. No. 5,730,983.

In one embodiment, a protein (e.g., an antibody described herein) has a statistically significant effect in an animal model. For example, the protein has a statistically significant effect on a symptom of an inflammatory disorder, a disorder characterized by excessive LFA-1 activity, or a LFA-1 mediated disorder.

Additional Assays

ELISA. Proteins encoded by a display library can also be screened for a binding property using an ELISA assay. For example, each protein is contacted to a microtitre plate whose bottom surface has been coated with the target, e.g., a limiting amount of the target. The plate is washed with buffer to remove non-specifically bound polypeptides. Then the amount of the protein bound to the plate is determined by probing the plate with an antibody that can recognize the polypeptide, e.g., a tag or constant portion of the polypeptide. The antibody is linked to an enzyme such as alkaline phosphatase, which produces a colorimetric product when appropriate substrates are provided. The protein can be purified from cells or assayed in a display library format, e.g., as a fusion to a filamentous bacteriophage coat. Alternatively, cells (e.g., live or fixed) that express the target molecule, e.g., a conformationally biased LFA-1, can be plated in a microtitre plate and used to test the affinity of the peptides/antibodies present in the display library or obtained by selection from the display library.

In another version of the ELISA assay, each polypeptide of a diversity strand library is used to coat a different well of a microtitre plate. The ELISA then proceeds using a constant target molecule to query each well.

Homogeneous Binding Assays. The binding interaction of candidate protein with a target can be analyzed using a homogenous assay, i.e., after all components of the assay are added, additional fluid manipulations are not required. For example, fluorescence resonance energy transfer (FRET) can be used as a homogenous assay (see, for example, Lakowicz et al., U.S. Pat. No. 5,631,169; Stavrianopoulos, et al., U.S. Pat. No. 4,868,103). Another example of a homogenous assay is Alpha Screen (Packard Bioscience, Meriden Conn.).

Surface Plasmon Resonance (SPR). The binding interaction of a molecule isolated from a display library and a target can be analyzed using SPR. SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in U.S. Pat. No. 5,641,640; Raether (1988) *Surface Plasmons* Springer Verlag; Sjolander and Urbaniczky (1991) *Anal. Chem.* 63:2338-2345; Szabo et al. (1995) *Curr. Opin. Struct. Biol.* 5:699-705 and on-line resources provide by BIAcore International AB (Uppsala, Sweden).

Information from SPR can be used to provide an accurate and quantitative measure of the equilibrium dissociation constant ($K_d$), and kinetic parameters, including $K_{on}$ and $K_{off}$, for the binding of a biomolecule to a target. Such data can be used to compare different biomolecules. For example, proteins encoded by nucleic acid selected from a library of diversity strands can be compared to identify individuals that have high affinity for the target or that have a slow $K_{off}$. This information can also be used to develop structure-activity relationships (SAR). For example, the kinetic and equilibrium binding parameters of matured versions of a parent protein can be compared to the parameters of the parent protein. Variant amino acids at given positions can be identified that correlate with particular binding parameters, e.g., high affinity and slow $K_{off}$. This information can be combined with structural modeling (e.g., using homology modeling, energy minimization, or structure determination by crystallography or NMR). As a result, an understanding of the physical interaction between the protein and its target can be formulated and used to guide other design processes.

Protein Arrays. Polypeptides identified from the display library can be immobilized on a solid support, for example, on a bead or an array. For a protein array, each of the polypeptides is immobilized at a unique address on a support. Typically, the address is a two-dimensional address. Protein arrays are described below (see, e.g., Diagnostics).

Cellular Assays. Candidate proteins can be selected from a library by transforming the library into a host cell; the library could have been previously identified from a display library. For example, the library can include vector nucleic acid sequences that include segments that encode the polypeptides and that direct expression, e.g., such that the polypeptides are produced within the cell, secreted from the cell, or attached to the cell surface. The cells can be screened or selected for polypeptides that bind to the aLFA-1, e.g., as detected by a change in a cellular phenotype or a cell-mediated activity. For example, in the case of an antibody that binds to aLFA-1, the activity may be an in vitro assay for cell adhesion, cell invasion, or a lymphocyte activity.

Protein Production

Standard recombinant nucleic acid methods can be used to express an integrin binding protein. See, for example, the techniques described in Sambrook & Russell, *Molecular Cloning: A Laboratory Manual,* $3^{rd}$ Edition, Cold Spring Harbor Laboratory, N.Y. (2001) and Ausubel et al., Current Protocols in Molecular Biology (Greene Publishing Associates and Wiley Interscience, N.Y. (1989). Generally, a nucleic acid sequence encoding the binding protein is cloned into a nucleic acid expression vector. If the protein includes multiple polypeptide chains, each chain can be cloned into an expression vector, e.g., the same or different vectors, that are expressed in the same or different cells.

Antibody Production. Some antibodies, e.g., Fabs, can be produced in bacterial cells, e.g., *E. coli* cells. For example, if the Fab is encoded by sequences in a phage display vector that includes a suppressible stop codon between the display entity and a bacteriophage protein (or fragment thereof), the vector nucleic acid can be transferred into a bacterial cell that cannot suppress a stop codon. In this case, the Fab is not fused to the gene III protein and is secreted into the periplasm and/or media.

Antibodies can also be produced in eukaryotic cells. In one embodiment, the antibodies (e.g., scFv's) are expressed in a yeast cell such as *Pichia* (see, e.g., Powers et al., 2001, *J. Immunol. Methods.* 251:123-35), *Hanseula*, or *Saccharomyces*.

In one preferred embodiment, antibodies are produced in mammalian cells. Preferred mammalian host cells for expressing the clone antibodies or antigen-binding fragments thereof include Chinese Hamster Ovary (CHO cells) (including dhfr-CHO cells, described in Urlaub and Chasin, 1980, *Proc. Natl. Acad. Sci. USA* 77:4216-4220, used with a DHFR selectable marker, e.g., as described in Kaufman and Sharp, 1982, *Mol. Biol.* 159:601 621), lymphocytic cell lines, e.g., NS0 myeloma cells and SP2 cells, COS cells, and a cell from a transgenic animal, e.g., a transgenic mammal. For example, the cell is a mammary epithelial cell.

In addition to the nucleic acid sequence encoding the diversified immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

In an exemplary system for recombinant expression of an antibody, or antigen-binding portion thereof, a recombinant expression vector encoding both the antibody heavy chain and the antibody light chain is introduced into dhfr CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G coupled matrix.

For antibodies that include an Fc domain, the antibody production system may produce antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fc receptors and complement C1q (Burton and Woof, 1992, *Adv. Immunol.* 51:1-84; Jefferis et al., 1998, *Immunol. Rev.* 163:59-76). In one embodiment, the Fc domain is produced in a mammalian expression system that appropriately glycosylates the residue corresponding to asparagine 297. The Fc domain can also include other eukaryotic post-translational modifications.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

One method for producing a transgenic mouse is as follows. Briefly, a targeting construct that encodes the antibody is microinjected into the male pronucleus of fertilized oocytes. The oocytes are injected into the uterus of a pseudopregnant foster mother for the development into viable pups. Some offspring incorporate the transgene.

It is also possible to produce antibodies that bind to aLFA-1 by immunization, e.g., using an animal, e.g., with natural, human, or partially human immunoglobulin loci. Non-human antibodies can also be modified to include substitutions that insert human immunoglobulin sequences, e.g., consensus human amino acid residues at particular positions, e.g., at one or more of the following positions (preferably at least five, ten, twelve, or all): (in the FR of the variable domain of the light chain) 4L, 35L, 36L, 38L, 43L, 44L, 58L, 46L, 62L, 63L, 64L, 65L, 66L, 67L, 68L, 69L, 70L, 71L, 73L, 85L, 87L, 98L, and/or (in the FR of the variable domain of the heavy chain) 2H, 4H, 24H, 36H, 37H, 39H, 43H, 45H, 49H, 58H, 60H, 67H, 68H, 69H, 70H, 73H, 74H, 75H, 78H, 91H, 92H, 93H, and/or 103H (according to the Kabat numbering). See, e.g., U.S. Pat. No. 6,407,213.

Target Protein Production. Method for producing an conformationally biased LFA-1 protein are described, e.g., in US 2002-0123614, Shimaoka, M et al. (2003) *Cell* 112,99-111; Shimaoka, M et al. (2002) *Annu. Rev. Biophys. Biomol. Struct.* 31, 485-516; and Shimaoka, M et al. (2001) *Proc Natl Acad Sci USA* 98:6009-6014 and Luo et al. (2003) *Proc Natl Acad Sci USA.* 100(5):2403-8.

Biotinylation Methods. A variety of methods are available to biotinylate proteins, e.g., an immunoglobulin protein or a target protein. For example, the protein can be incubated with a 5-fold molar excess of sulfo-N-HS-SS-biotin in 50 mM HEPES, pH 8.0, 100 mM NaCl overnight at 4° C. Free biotin is removed by buffer exchange into PBS, 0.01% Tween 20, e.g., using a BIOMAX™ device with a 10 kDa molecular weight cut-off membrane or by dialysis. The number of biotin molecules incorporated per mole of protein can be determined using the HABA assay as described by the manufacturer (Pierce).

Pharmaceutical Compositions

In another aspect, the invention provides compositions, e.g., pharmaceutically acceptable compositions, which include an integrin binding protein, e.g., an antibody or other protein. The integrin binding protein can be, e.g., a protein that preferentially binds to activated LFA-1, formulated together with a pharmaceutically acceptable carrier. As used herein, "pharmaceutical compositions" encompass diagnostic compositions, e.g., labeled binding proteins (e.g., for in vivo imaging) as well as therapeutic compositions.

As used herein, "pharmaceutically acceptable carrier" includes any and all solvents, dispersion media, coatings, antibacterial and antifungal agents, isotonic and absorption delaying agents, and the like that are physiologically compatible. The carrier can be suitable for intravenous, intramuscular, subcutaneous, parenteral, spinal or epidermal administration (e.g., by injection or infusion). Depending on the route of administration, the composition may be coated in a material to protect the binding protein from the action of acids and other natural conditions that may inactivate the binding protein.

A "pharmaceutically acceptable salt" refers to a salt that retains the desired biological activity of the parent compound and does not impart any undesired toxicological effects (see e.g., Berge, et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form can depend on the intended mode of administration and therapeutic application. Typical compositions are in the form of injectable or infusible solutions. One common mode of administration is parenteral (e.g., intravenous, subcutaneous, intraperitoneal, intramuscular). For example, the integrin binding protein is administered by intravenous infusion or injection. In another preferred embodiment, the integrin binding protein is administered by intramuscular or subcutaneous injection.

The phrases "parenteral administration" and "administered parenterally" as used herein mean modes of administration other than enteral and topical administration. Parenteral administration is usually by injection. Parenteral administration includes, e.g., intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Pharmaceutical compositions typically are sterile and stable under the conditions of manufacture and storage. A pharmaceutical composition can also be tested to insure it meets regulatory and industry standards for administration. For example, endotoxin levels in the preparation can be tested using the *Limulus amebocyte* lysate assay (e.g., using the kit from Bio Whittaker lot # 7L3790, sensitivity 0.125 EU/mL) according to the USP 24/NF 19 methods. Sterility of pharmaceutical compositions can be determined using thioglycollate medium according to the USP 24/NF 19 methods. For example, the preparation is used to inoculate the thioglycollate medium and incubated at 35° C. for 14 or more days. The medium is inspected periodically to detect growth of a microorganism.

The composition can be formulated as a solution, microemulsion, dispersion, liposome, or other ordered structure suitable for delivering a high concentration of the binding protein. Sterile injectable solutions can be prepared by incorporating the binding protein in the required amount in an appropriate solvent with one or a combination of any other ingredients, followed by filtered sterilization. Generally, dispersions are prepared by incorporating the binding protein into a sterile vehicle that contains a basic dispersion medium and any other ingredients. Sterile powders for the preparation of sterile injectable solutions can be prepared by vacuum drying and freeze-drying. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

An integrin binding protein can be administered by any appropriate method. For many applications, the route of administration is intravenous injection or infusion. For example, for therapeutic applications, the integrin binding protein can be administered by intravenous infusion. In certain embodiments, the binding protein may be prepared with a carrier that protects the protein against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are available. See, e.g., *Sustained and Controlled Release Drug Delivery Systems*, J. R. Robinson, ed., Marcel Dekker, Inc., New York, 1978.

To administer a compound described herein by other than parenteral administration, it may be necessary to coat the compound with, or co-administer the compound with, a material to prevent its inactivation. The protein may be incorporated with excipients and used in the form of ingestible tablets, buccal tablets, troches, capsules, elixirs, suspensions, syrups, wafers, and the like. In certain embodiments, the binding protein is administered orally, for example, with an inert diluent or an assimilable edible carrier. The protein may also be enclosed in a hard or soft shell gelatin capsule, compressed into tablets, or incorporated directly into the subject's food or drink.

Pharmaceutical compositions can be administered by a medical device. For example, a pharmaceutical composition described herein can be administered with a needleless hypodermic injection device, such as the devices disclosed in U.S. Pat. Nos. 5,399,163, 5,383,851, 5,312,335, 5,064,413, 4,941,880, 4,790,824, and 4,596,556. Examples of implants and modules include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of binding protein calculated to produce the desired therapeutic effect in association with the required pharmaceutical carrier. The specification for the dosage unit forms can be dictated by and directly dependent on (a) the particular characteristics of the binding protein and the particular therapeutic effect to be achieved, and (b) the sensitivity of a particular individual.

An exemplary, non-limiting range for a therapeutically or prophylactically effective amount of an antibody described herein is 0.01-20 mg/kg, e.g., 1-10, 0.01-10, 0.03-5, 0.02-2, or 0.01-1 mg/kg. The integrin binding protein, particularly an aLFA-1 binding antibody, can be administered by intravenous infusion. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

A pharmaceutical composition may include a "therapeutically effective amount" or a "prophylactically effective amount" of an integrin binding protein, e.g., aLFA-1-binding protein. A "therapeutically effective amount" refers to an amount effective, at dosages and for periods of time necessary, to achieve the desired therapeutic result. A therapeutically effective amount of the composition may vary according to factors such as the disease state, age, sex, and weight of the individual, and the ability of the protein to elicit a desired response in the individual. A therapeutically effective amount is also one in which any toxic or detrimental effects of the composition are outweighed by the therapeutically beneficial effects. A "therapeutically effective dosage" preferably inhibits a measurable parameter, e.g., parameter of inflammation by at least about 5, 10, 20%, more preferably by at least about 40%, even more preferably by at least about 60%, and still more preferably by at least about 80% relative to untreated subjects. The ability of a compound to inhibit a measurable parameter, e.g., a parameter of inflammation, can be evaluated in an animal model system of inflammation. Alternatively, this property of a composition can be evaluated by examining the ability of the compound to inhibit, such inhibition in vitro by assays known to the skilled practitioner.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Stabilization and Retention

In one embodiment, an integrin binding protein (e.g., an aLFA-1-binding antibody described herein or other integrin-binding protein) is physically associated with a moiety that improves its stabilization and/or retention in circulation, e.g., in blood, serum, lymph, or other tissues, e.g., by at least 1.5, 2, 5, 10, or 50 fold. For example, an aLFA-1 binding ligand can be associated with a polymer, e.g., a substantially non-antigenic polymers, such as polyalkylene oxides or polyethylene oxides. Suitable polymers will vary substantially by weight. Polymers having molecular number average weights ranging from about 200 to about 35,000 (or about 1,000 to about 15,000, and 2,000 to about 12,500) can be used. For example, an aLFA-1 binding ligand can be conjugated to a water soluble polymer, e.g., hydrophilic polyvinyl polymers, e.g. polyvinylalcohol and polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. See, e.g., U.S. Application Ser. No. 60/546,354, filed on Feb. 19, 2004, for further examples.

Treatments

Proteins that bind to an activated integrin, e.g., aLFA-1, have therapeutic and prophylactic utilities. For example, these binding proteins can be administered to a subject to treat or prevent a disorder, particularly inflammation, an inflammatory disorder, a disorder characterized by excessive LFA-1 activity, or a LFA-1 mediated disorder.

A binding protein that preferentially binds to aLFA-1 can be used to prevent leukocytes with aLFA-1 from interacting with a cognate ligand of LFA-1. The aLFA-1 binding protein can reduce the ability of the leukocyte from interacting with other cells or the extracellular matrix. For example, the binding protein can reduce the ability of the leukocyte to interact with an endothelial cell.

Because the binding protein preferentially binds to aLFA-1, a lower concentration of the binding protein may be effective to inhibiting such interactions, relative to the concentration required to achieve an equivalent effect using a binding protein that does not have a preference for aLFA-1 relative to non-activated conformations of LFA-1.

The integrin binding protein can be administered in an amount effective to ameliorate at least one symptom of inflammation, e.g., cause a statistically significant change in a parameter of inflammation. Exemplary parameters include: local temperature, core temperature, swelling (e.g., as measured), redness, local or systemic white blood cell count, presence or absence of neutrophils, cytokine levels, and elastase activity. For quantitative parameters, the degree of change can be, e.g., at least 10, 20, 30, 50, or 80%.

The integrin binding protein can be administered in an amount effective to reduce inflammation. Medical professionals can examine the subject to evaluate extent of inflammation.

The integrin binding protein can be administered in an amount effective to reduce leukocyte activity. Exemplary leukocyte activities include migration and homing to sites on inflammation, adherence to the endothelium. In one embodiment, the binding protein is administered locally, e.g., to reduce local concentration of the leukocyte.

The integrin binding protein can be administered as part of a regimen, e.g., of multiple bolus doses. In one embodiment, the doses can also include the same (or within 20, or 10% of the same) amount of the protein. In another embodiment, the initial dose is greater or less than one or more subsequent doses, e.g., at least 10, 20, 50, 60, 70, or 80% greater or less than.

The dose can be selected or titrated, e.g., to achieve a detectable serum concentration whose mean trough concentration is less than 9, 7, 6, 5, 4, 3, 2, 1, 0.3, 0.1, 0.03, or 0.01 µg/ml of the integrin binding protein.

As used herein, the term "treat" or "treatment" is the administration of an integrin binding protein to a subject. The protein can be administered alone or in combination with a second agent to a subject, an isolated tissue, or a cell. The protein can be administered to prevent or ameliorate the disorder, one or more symptoms of the disorder or a predisposition toward the disorder. Treating a cell includes modulation of an activity (e.g., function or viability) of the cell. Exemplary functions of leukocytes that can be modulated include binding, migration, adhesion, and a T cell function. The modulation can reduce the ability of a cell to mediate a disorder, e.g., inflammation, an inflammatory disorder, a disorder characterized by excessive LFA-1 activity, or a LFA-1 mediated disorder. Another example is an activity that, directly or indirectly, reduces inflammation or an indicator of inflammation. For example, the reduction can reduce a lymphocyte activity.

An integrin binding protein can also be used to prevent a disorder, e.g., inflammation, inflammatory disorder, a disorder characterized by excessive LFA-1 activity, or a LFA-1 mediated disorder. A prophylactic treatment can be effective, upon single- or multiple-dose administration to the subject, in preventing or delaying the occurrence of the onset or recurrence of a disorder, e.g., inflammation, an inflammatory disorder, a disorder characterized by excessive LFA-1 activity, or a LFA-1 mediated disorder.

As used herein, the term "subject" includes human and non-human animals. Human subjects include a human patient having or suspected of having a disorder inflammation, inflammatory disorder, a disorder characterized by excessive LFA-1 activity, or a LFA-1 mediated disorder.

The term "non-human animals" includes all vertebrates, e.g., non-mammals (such as chickens, amphibians, reptiles) and mammals, such as non-human primates, sheep, dog, cow, pig, etc. For example, the subject can be a non-human mammal that has cells that can express LFA-1 or an LFA-1-like antigen with which an antibody described herein cross-reacts. Moreover, an aLFA-1-binding protein can be administered to a non-human mammal expressing LFA-1 or an LFA-1-like antigen with which the binding protein interacts (e.g., a primate, pig or mouse) for veterinary purposes or as an animal model of human disease. Regarding the latter, such animal models may be useful for evaluating the therapeutic efficacy of the binding protein (e.g., testing of dosages and time courses of administration).

The aLFA-1-binding proteins can selectively inhibit, inactivate, or kill cells that have activated LFA-1, e.g., to reduce inflammation, a leukocyte population, or leukocyte activity. For example, the aLFA-1 binding protein can be conjugated to an agent, e.g., a cytotoxic agent such as a toxin, radioisotope, or short-range, high-energy α-emitters.

The aLFA-1 binding proteins can be used directly in vivo to inhibit, inactivate, or kill cells that present activated LFA-1 via natural complement-dependent cytotoxicity (CDC) or antibody-dependent cellular cytotoxicity (ADCC). In one embodiment, the protein includes a complement binding effector domain, such as an Fc portion (e.g., functional portion) from IgG1, -2, or -3 or corresponding portions of IgM which bind complement. Also encompassed by the invention is a method of killing or ablating which involves using the aLFA-1 binding proteins for prophylaxis. For example, these materials can be used to prevent or delay development or progression of inflammatory disease.

An aLFA-1 binding protein can be administered in combination with one or more of the existing modalities for treating a disorder described herein. "Combination" refers to the overlapping administration. For example, a subject may be receiving an aLFA-1 binding protein and another therapy, e.g., another therapeutic agent, but the subject may not be administered both therapies at the same instant. For example, the subject may receive a first injection with the aLFA-1 binding protein, and then receive a separate injection with another therapeutic agent. In another example, the aLFA-1 binding protein and the other agent are administered together in a single injection.

Regarding exemplary combinations, the aLFA-1 binding protein can used in combination with cyclosporins, rapamycins or ascomycins, or their immunosuppressive analogs, e.g. cyclosporin A, cyclosporin G, FK-506, rapamycin, 40-O-(2-hydroxy)ethyl-rapamycin etc.; corticosteroids; cyclophosphamide; azathioprene; methotrexate; brequinar; FTY 720; leflunomide; mnizoribine; mycophenolic acid; mycophenolate mofetil; 15-deoxyspergualine; immunosuppressive monoclonal antibodies, e.g., monoclonal antibodies to leukocyte receptors, e.g., MHC, CD2, CD3, CD4, CD7, CD25, CD28, B7, CD45, or CD58 or their ligands; or other immunomodulatory compounds, e.g. CTLA4Ig, or other adhesion molecule inhibitors, e.g. mAbs or low molecular weight inhibitors including selectin antagonists and VLA-4 antagonists. These combination therapies can be part of an immunomodulating regimens or a regimen for the treatment or prevention of allo- or xenograft acute or chronic rejection, an inflammatory disorder, or an autoimmune disorders.

In one embodiment, the aLFA-1 binding protein is administered to a subject to improve allo- or xenograft toleration. The protein can be administered, before, during, and/or after the graft. The graft can include, e.g., skin, heart, liver, lung, or kidney tissue or organs. For example, the graft can include pancreatic cells. The aLFA-1 binding protein can be administered in combination with other agents, e.g., agents that target CD154 or CD45RB, e.g., antibodies or soluble receptors that target these proteins, and/or rapamycin. See, e.g., Rayat et al. (2005) Diabetes 54:443-451.

Inflammatory Disorders

Exemplary inflammatory disorders include: acute and chronic immune and autoimmune pathologies (such as, but not limited to, rheumatoid arthritis (RA), juvenile chronic arthritis (JCA)), dermatological diseases (such as psoriasis and contact dermatitis), graft versus host disease (GVHD), scleroderma, diabetes mellitus, allergy; asthma, acute or chronic immune disease associated with an allogenic transplantation, such as, but not limited to, renal transplantation, cardiac transplantation, bone marrow transplantation, liver transplantation, pancreatic transplantation, small intestine transplantation, lung transplantation and skin transplantation; chronic inflammatory pathologies such as, but not limited to, sarcoidosis, chronic inflammatory bowel disease, ulcerative colitis, and Crohn's pathology or disease; multiple sclerosis; vascular inflammatory pathologies, such as, but not limited to, disseminated intravascular coagulation, atherosclerosis, Kawasaki's pathology and vasculitis syndromes, such as, but not limited to, polyarteritis nodosa, Wegener's granulomatosis, Henoch-Schonlein purpura, giant cell arthritis and microscopic vasculitis of the kidneys; chronic active hepatitis; Sjogren's syndrome; psoriatic arthritis; ophthalmic inflammatory diseases; enteropathic arthritis; reactive arthritis and arthritis associated with inflammatory bowel disease; infection diseases (such as septic shock, traumatic shock); and uveitis.

An aLFA-1-binding protein can be used to treat or prevent one of the foregoing diseases or disorders. For example, the protein can be administered (locally or systemically) in an amount effective to ameliorate at least one symptom of the respective disease or disorder. The protein may also ameliorate inflammation, e.g., a parameter of inflammation, e.g., such as local temperature, swelling (e.g., as measured), redness, local or systemic white blood cell count, presence or absence of neutrophils, cytokine levels, elastase activity, and so forth. It is possible to evaluate a subject, e.g., prior, during, or after administration of the protein, for one or more of parameters of inflammation, e.g., an aforementioned parameter.

IBD. Inflammatory bowel diseases (IBD) include generally chronic, relapsing intestinal inflammation. IBD refers to two distinct disorders, Crohn's disease and ulcerative colitis (UC). The clinical symptoms of IBD include intermittent rectal bleeding, cramping abdominal pain, weight loss and diarrhea. A clinical index can also be used to monitor IBD such as the Clinical Activity Index for Ulcerative Colitis. See also, e.g., Walmsley et al. *Gut.* 1998 July; 43(1):29-32 and Jowett et al. (2003) Scand J Gastroenterol. 38(2):164-71. An integrin binding protein (e.g., an aLFA-1 binding antibody described herein) can be used to ameliorate at least one symptom of IBD or to ameliorate a clinical index of IBD.

Psoriasis. Psoriasis is a chronic skin disease, characterized by scaling and inflammation. Psoriasis affects 1.5 to 2 percent of the United States population, or almost 5 million people. When psoriasis develops, typically patches of skin thicken, redden, and become covered with silvery scales, referred to as plaques. Psoriasis most often occurs on the elbows, knees, scalp, lower back, face, palms, and soles of the feet. The disease also may affect the fingernails, toenails, and the soft tissues inside the mouth and genitalia. About 10 percent of people with psoriasis have joint inflammation that produces symptoms of arthritis. The chronic skin inflammation of psoriasis is associated with hyperplastic epidermal keratinocytes and infiltrating mononuclear cells, including CD4+ memory T cells, neutrophils and macrophages.

Patients can be evaluated using a static Physician Global Assessment (sPGA), and receive a category score ranging from six categories between clear and very severe. The score is based on plaque, scaling, and erythema.

An integrin binding protein (e.g., an aLFA-1 binding antibody described herein) can be used to ameliorate at least one symptom of psoriasis or to ameliorate a clinical index of psoriasis (e.g., sPGA index). The protein can be administered locally or systemically.

Rheumatoid Arthritis (RA). This disorder is characterized by inflammation in the lining of the joints and/or other internal organs. It is typically chronic, but can include flare-ups. Exemplary symptoms include inflammation of joints, swelling, difficulty moving, pain, loss of appetite, fever, loss of energy, anemia, lumps (rheumatoid nodules) under the skin, especially in areas subject to pressure (e.g., back of elbows). In the clinical realm, rheumatoid arthritis (RA) is the most common form of the severe arthrodysplastic disease. RA is a progressive disease. An aLFA-1 binding protein can be used to ameliorate or prevent at least one symptom of rheumatoid arthritis and other arthrodysplastic disorders.

An aLFA-1 binding protein can be administered in conjunction with another agent for treating rheumatoid arthritis, such as NSAIDs and aspirin, analgesics, and corticosteroids, help reduce joint pain, stiffness and swelling. Exemplary agents include disease-modifying anti-rheumatic drugs (DMARDs) such as methotrexate, leflunomide, D-Penicillamine, sulfasalazine, gold therapy, minocycline, azathioprine, hydroxychloroquine (and other anti-malarials), cyclosporine, Prosorba therapy, and biologic agents.

Asthma

Asthma is a heterogeneous family of diseases. It is characterized by a hyper-responsiveness of the tracheobronchi to stimuli (McFadden, E. R. et al., In: Harrison's Principles of Internal Medicine, 10th Ed., Petersdorf, R. G. et al., Eds., McGraw-Hill, NY (1983), pages 1512-1519); Kay, A. B., Allergy and Inflammation, Academic Press, NY (1987); which references are incorporated herein by reference). Clinically, asthma is manifested by the extensive narrowing of the tracheobronchi, by thick tenacious secretions, by paroxysms of dyspnea, cough, and wheezing. Although the relative contribution of each of these conditions is unknown, the net result is an increase in airway resistance, hyperinflation of the lungs and thorax, abnormal distribution of ventilation and pulmonary blood flow. The disease is manifested in episodic periods of acute symptoms interspersed between symptom-free periods. The acute episodes result in hypoxia, and can be fatal. Approximately 3% of the general world population suffers from the disease.

As used herein, "asthma" refers to either allergic or idiosyncratic asthma. Allergic asthma is usually associated with a heritable allergic disease, such as rhinitis, urticaria, eczema, etc. The condition is characterized by positive wheal-and-flare reactions to intradermal injections of airborne antigens (such as pollen, environmental or occupational pollutants, etc.), and increased serum levels of IgE. The development of allergic asthma appears to be causally related to the presence of IgE antibodies in many patients. Asthma patients who do not exhibit the above-described characteristics are considered to have idiosyncratic asthma.

An integrin binding protein (e.g., an aLFA-1 binding antibody described herein) can be used to ameliorate at least one symptom of asthma or to ameliorate a clinical index of asthma (e.g., airway responsiveness). The protein can be administered locally (e.g., by inhalation) or systemically (e.g., by injection).

Ischemia/Stroke and Other Cardiovascular Disorders

The binding proteins described herein can also be used to treat or prevent cardiovascular disorders in which LFA-1 is a factor. Such disorders include, e.g., ischemia/reperfusion injury, e.g., leukocyte-mediated reperfusion damage (e.g., post thrombolytic therapy), myocardial infarction, stroke, gut ischemia, and renal failure or hemorrhage shock.

An integrin binding protein (e.g., an aLFA-1 binding antibody described herein) can be administered to a subject who is at risk for one of the above disorders, e.g., at risk for a stroke, or to a subject who had a stroke or other cardiovascular dysfunction. For example, the binding protein can be administered before, during, or immediately after, or any other time after such a stroke or other cardiovascular dysfunction, e.g., within 2, 4, 6, 12, 24, or 48 hours. In one embodiment, the binding protein is administered to reach a desired circulating concentration for at least 1, 2, 4, 5, 7, or 10 days.

An integrin binding protein (e.g., aLFA-1 binding protein, e.g., an aLFA-1 binding antibody described herein) can be used to treat a focal ischemic stroke, e.g., a thromoboembolic stroke, or a cerebral ischemic stroke. "Focal ischemic stroke" is defined as damage to the brain caused by interruption of the blood supply to a region, generally caused by obstruction of any one or more of the "main cerebral arteries" (e.g. middle cerebral artery, anterior cerebral artery, posterior cerebral artery, internal carotid artery, vertebral artery or basilar artery). The "arterial obstruction" is generally a single embolus or thrombus. A cerebral embolism stroke can result from the obstruction of secondary arteries or arterioles, e.g., as in the model of Bowes et al., Neurology 45:815-819 (1995) in which a plurality of clot particles occlude secondary arteries or arterioles.

The aLFA-1 binding protein can be administered to increase cerebral blood flow can be increased and/or reduce infarct size in a subject having suffered the stroke. The administering can be provided, e.g., prior to removal of the arterial obstruction. For example, the obstruction is not removed until a therapeutic benefit, e.g., such as increased cerebral blood flow is detected. The method can be performed without administering a thrombolytic agent.

The aLFA-1 binding protein can be administered to a patient as soon as possible once the condition of acute ischemic stroke has been diagnosed, e.g., as suggested by focal deficit on neurologic examination. Neurologic examination and, optionally, neuro-imaging techniques such as computed tomography (CT) and magnetic resonance imaging (MRI) (including diffusion weighted imaging (DWI) and per-fusion imaging (PI)); vascular imaging (e.g., duplex scanning and transcranial Doppler ultrasound and laser Doppler); angiography (e.g., computerized digital subtraction angiography (DSA) and MR angiography) as well as other invasive or non-invasive techniques can be used to diagnose acute ischemic stroke.

The aLFA-1 binding protein can be administered at least once or continuously at any time from immediately following to about 24 hours after the onset of stroke. In certain embodiments, the aLFA-1 binding protein is first administered to the patient at a time between about 15 minutes (or 30 minutes or 45 minutes) to about 5 hours (or 12 hours or 24 hours) from the onset of stroke. For example, the aLFA-1 binding protein may be first administered by bolus dosage as soon as stroke is diagnosed, followed by a subsequent bolus dosage of the antagonist (e.g. 5-24 hours after the initial bolus dosage). In another example the protein is administered continuously.

Cancer

An integrin binding protein (e.g., an aLFA-1 binding antibody described herein) can be used to treat a proliferative disorder of T-cells, e.g., a T cell leukemia or lymphoma. In one embodiment, the disorder is acute promyelocytic leukemia. Other exemplary disorders that can be treated include myeloid disorders, such as acute promyeloid leukemia (APML), acute myelogenous leukemia (AML) and chronic myelogenous leukemia (CML) (reviewed in Vaickus, L. (1991) *Crit. Rev. in Oncol./Hemotol.* 11:267-97). Lymphoid malignancies that may be treated include, e.g., acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, e.g., non-Hodgkin's lymphoma and variants thereof, peripheral T-cell lymphomas, adult T-cell leukemia/lymphoma (ATL), cutaneous T-cell lymphoma (CTCL), large granular lymphocytic leukemia (LGF) and Hodgkin's disease.

Diagnostic Uses

Binding proteins that bind to an activated integrin (e.g., aLFA-1), can also be used for diagnostics in vitro and in vivo. In one aspect, the invention provides a diagnostic method for detecting the presence of an aLFA-1 in vitro or in vivo (e.g., in vivo imaging in a subject).

In one embodiment, the integrin binding protein is used to evaluate a sample in vitro (e.g., a biological sample). The method includes: (i) contacting a sample with aLFA-1-binding protein; and (ii) detecting formation of a complex between the aLFA-1-binding protein and the sample. The method can also include contacting a reference sample (e.g., a control sample) with the binding protein, and determining the extent of formation of the complex between the binding protein and the sample, relative to the same for the reference sample. A change, e.g., a statistically significant change, in the formation of the complex in the sample or subject relative to the control sample or subject can be indicative of the presence of aLFA-1 in the sample. Samples can be obtained by surgical or non-surgical methods.

Another method includes: (i) administering the aLFA-1-binding protein to a subject; and (ii) detecting formation of a complex between the aLFA-1-binding protein, and the subject. The detecting can include determining location or time of formation of the complex. In one embodiment, the subject has, is suspected of having, or is at risk for a disorder described herein, e.g., an inflammatory disorder, a disorder characterized by excessive LFA-1 activity, or a LFA-1 mediated disorder.

The aLFA-1-binding protein can be directly or indirectly labeled with a detectable substance to facilitate detection of the bound or unbound antibody. Suitable detectable substances include various enzymes, prosthetic groups, fluorescent materials, luminescent materials and radioactive materials.

Complex formation between the aLFA-1-binding protein and aLFA-1 can be detected by measuring or visualizing either the binding protein bound to the aLFA-1 or unbound binding protein. Conventional detection assays can be used, e.g., an enzyme-linked immunosorbent assays (ELISA), a radioimmunoassay (RIA) or tissue immunohistochemistry. Further to labeling the aLFA-1-binding protein, the presence of aLFA-1 can be assayed in a sample by a competition immunoassay utilizing standards labeled with a detectable substance and an unlabeled aLFA-1-binding protein. In one example of this assay, the biological sample, the labeled standards and the aLFA-1 binding agent are combined and the amount of labeled standard bound to the unlabeled binding protein is determined. The amount of aLFA-1 in the sample is inversely proportional to the amount of labeled standard bound to the aLFA-1 binding agent.

Fluorophore and chromophore labeled binding proteins can be prepared. Since antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer (1968) *Science,* 162:526 and Brand, L. et al. (1972) *Annual Review of Biochemistry,* 41:843-868. The binding proteins can be labeled with fluorescent chromophore groups by conventional procedures such as those disclosed in U.S. Pat. Nos. 3,940,475, 4,289,747, and 4,376,110. One group of fluorescers having a number of the desirable properties described above is the xanthene dyes, which include the fluoresceins and rhodamines. Another group of fluorescent compounds are the naphthylamines. Once labeled with a fluorophore or chromophore, the binding protein can be used to detect the presence or localization of the aLFA-1 in a sample, e.g., using fluorescent microscopy (such as confocal or deconvolution microscopy).

Histological Analysis. Immunohistochemistry can be performed using the binding proteins described herein. For example, in the case of an antibody, the antibody can be synthesized with a label (such as a purification or epitope tag), or can be detectably labeled, e.g., by conjugating a label or label-binding group. For example, a chelator can be attached to the antibody. The antibody is then contacted to a histological preparation, e.g., a fixed section of tissue that is on a microscope slide. After an incubation for binding, the preparation is washed to remove unbound antibody. The preparation is then analyzed, e.g., using microscopy, to identify if the antibody bound to the preparation.

The antibody (or other polypeptide or peptide) can be unlabeled at the time of binding. After binding and washing, the antibody is labeled in order to render it detectable.

Protein Arrays. The aLFA-1-binding protein can also be immobilized on a protein array. The protein array can be used as a diagnostic tool, e.g., to screen medical samples (such as isolated cells, blood, sera, biopsies, and the like). Of course, the protein array can also include other binding proteins, e.g., that bind to aLFA-1 or to other target molecules, such as hyaluronic acid.

Methods of producing protein arrays are described, e.g., in De Wildt et al (2000) *Nat. Biotechnol.* 18:989-994; Lueking et al. (1999) *Anal. Biochem.* 270:103-111; Ge (2000) *Nucleic Acids Res.* 28, e3, I-VII; MacBeath and Schreiber (2000)

Science 289:1760-1763; WO 01/40803 and WO 99/51773A1. Proteins for the array can be spotted at high speed, e.g., using commercially available robotic apparati, e.g., from Genetic MicroSystems or BioRobotics. The array substrate can be, for example, nitrocellulose, plastic, glass, e.g., surface-modified glass. The array can also include a porous matrix, e.g., acrylamide, agarose, or another polymer.

For example, the array can be an array of antibodies, e.g., as described in De Wildt, supra. Cells that produce the binding proteins can be grown on a filter in an arrayed format. Protein production is induced, and the expressed proteins are immobilized to the filter at the location of the cell.

A protein array can be contacted with a labeled target to determine the extent of binding of the target to each immobilized polypeptide from the diversity strand library. If the target is unlabeled, a sandwich method can be used, e.g., using a labeled probed, to detect binding of the unlabeled target.

Information about the extent of binding at each address of the array can be stored as a profile, e.g., in a computer database. The protein array can be produced in replicates and used to compare binding profiles, e.g., of a target and a non-target. Thus, protein arrays can be used to identify individual members of the diversity strand library that have desired binding properties with respect to one or more molecules.

An aLFA-1-binding protein described herein can also be used to detecting binding of an aLFA-1 to an insoluble support. For example, a sample can be immobilized on array, and aLFA-1 can be detected on the array using the aLFA-1-binding protein.

FACS. (Fluorescent Activated Cell Sorting). The aLFA-1-binding protein can be used to label cells, e.g., cells in a sample (e.g., a patient sample). For example, the protein can be used to detect activated integrins on cells (e.g., activated LFA-1). The binding protein is typically physically associated with (or attachable to) a fluorescent compound. The cells can then be sorted using fluorescent activated cell sorted (e.g., using a sorter available from Becton Dickinson Immunocytometry Systems, San Jose Calif.; see also U.S. Pat. Nos. 5,627,037; 5,030,002; and 5,137,809). As cells pass through the sorter, a laser beam excites the fluorescent compound while a detector counts cells that pass through and determines whether a fluorescent compound is attached to the cell by detecting fluorescence. The amount of label bound to each cell can be quantified and analyzed to characterize the sample.

The sorter can also deflect the cell and separate cells bound by the binding protein from those cells not bound by the binding protein. The separated cells can be cultured and/or characterized.

In vivo Imaging. Integrin binding proteins can be used to detect the presence of cells that include an activated integrin, e.g., cells presenting aLFA-1, in vivo. The method includes (i) administering to a subject (e.g., a patient having an inflammatory disorder, a disorder characterized by excessive LFA-1 activity, or a LFA-1 mediated disorder) an aLFA-1-binding antibody, conjugated to a detectable marker; (ii) exposing the subject to a means for detecting the detectable marker. For example, the subject is imaged, e.g., by NMR or other tomographic means.

Examples of labels useful for diagnostic imaging include radiolabels such as $^{131}$I, $^{111}$In, $^{123}$I, $^{99m}$Tc, $^{32}$P, $^{125}$I, $^{3}$H, $^{14}$C, and $^{188}$Rh, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes can also be employed. The binding protein can be labeled with such reagents using known techniques. For example, see Wensel and Meares (1983) *Radioimmunoimaging and Radioimmunotherapy*, Elsevier, New York for techniques relating to the radiolabeling of antibodies and D. Colcher et al. (1986) *Meth. Enzymol.* 121: 802-816.

A radiolabeled binding protein can also be used for in vitro diagnostic tests. The specific activity of a isotopically-labeled binding protein depends upon the half-life, the isotopic purity of the radioactive label, and how the label is incorporated into the antibody.

Procedures for labeling polypeptides with the radioactive isotopes (such as $^{14}$C, $^{3}$H, $^{35}$S, $^{125}$I, $^{32}$P, $^{131}$I) are generally known. For example, tritium labeling procedures are described in U.S. Pat. No. 4,302,438. Iodinating, tritium labeling, and $^{35}$S labeling procedures, e.g., as adapted for murine monoclonal antibodies, are described, e.g., by Goding, J. W. (*Monoclonal antibodies: principles and practice: production and application of monoclonal antibodies in cell biology, biochemistry, and immunology* 2nd ed. London; Orlando: Academic Press, 1986. pp 124-126) and the references cited therein. Other procedures for iodinating polypeptides, such as antibodies, are described by Hunter and Greenwood (1962) *Nature* 144:945, David et al. (1974) *Biochemistry* 13:1014-1021, and U.S. Pat. Nos. 3,867,517 and 4,376,110. Exemplary radio-isotopes that are useful for imaging include $^{123}$I, $^{131}$I, $^{111}$In, and $^{99m}$Tc. Procedures for iodinating antibodies are described by Greenwood, F. et al. (1963) *Biochem. J.* 89:114-123; Marchalonis, J. (1969) *Biochem. J.* 113:299-305; and Morrison, M. et al. (1971) *Immunochemistry* 289-297. Procedures for $^{99m}$Tc-labeling are described by Rhodes, B. et al. in Burchiel, S. et al. (eds.), *Tumor Imaging: The Radioimmunochemical Detection of Cancer*, New York: Masson 111-123 (1982) and the references cited therein. Procedures suitable for $^{111}$In-labeling antibodies are described by Hnatowich, D. J. et al. (1983) *J. Immul. Methods,* 65:147-157, Hnatowich, D. et al. (1984) *J. Applied Radiation,* 35:554-557, and Buckley, R. G. et al. (1984) *F.E.B.S.* 166:202-204.

In the case of a radiolabeled binding protein, the binding protein is administered to the patient, is localized to cells with which the binding protein reacts, and is detected or "imaged" in vivo using known techniques such as radionuclear scanning using e.g., a gamma camera or emission tomography. See e.g., A. R. Bradwell et al., "Developments in Antibody Imaging", *Monoclonal Antibodies for Cancer Detection and Therapy*, R. W. Baldwin et al., (eds.), pp 65-85 (Academic Press 1985). Alternatively, a positron emission transaxial tomography scanner, such as designated Pet VI located at Brookhaven National Laboratory, can be used where the radiolabel emits positrons (e.g., $^{11}$C, $^{18}$F, $^{15}$O, and $^{13}$N).

MRI Contrast Agents. Magnetic Resonance Imaging (MRI) uses NMR to visualize internal features of living subject, and is useful for prognosis, diagnosis, treatment, and surgery. MRI can be used without radioactive tracer compounds for obvious benefit. Some MRI techniques are summarized in EP-A-0 502 814. Generally, the differences related to relaxation time constants T1 and T2 of water protons in different environments are used to generate an image. However, these differences can be insufficient to provide sharp high resolution images.

The differences in these relaxation time constants can be enhanced by contrast agents. Examples of such contrast agents include a number of magnetic agents paramagnetic agents (which primarily alter T1) and ferromagnetic or superparamagnetic (which primarily alter T2 response). Chelates (e.g., EDTA, DTPA and NTA chelates) can be used to attach (and reduce toxicity) of some paramagnetic substances (e.g., $Fe^{+3}$, $Mn^{+2}$, $Gd^{+3}$). Other agents can be in the form of particles, e.g., less than 10 µm to about 10 nM in diameter). Particles can have ferromagnetic, anti-ferromagnetic or superparamagnetic properties. Particles can include, e.g., magnetite ($Fe_3O_4$), □-$Fe_2O_3$, ferrites, and other magnetic mineral compounds of transition elements. Magnetic particles may include: one or more magnetic crystals with and without nonmagnetic material. The nonmagnetic material can include synthetic or natural polymers (such as sepharose, dextran, dextrin, starch and the like The aLFA-1-binding proteins can also be labeled with an indicating group containing of the NMR-active $^{19}F$ atom, or a plurality of such atoms inasmuch as (i) substantially all of naturally abundant fluorine atoms are the $^{19}F$ isotope and, thus, substantially all fluorine-containing compounds are NMR-active; (ii) many chemically active polyfluorinated compounds such as trifluoracetic anhydride are commercially available at relatively low cost, and (iii) many fluorinated compounds have been found medically acceptable for use in humans such as the perfluorinated polyethers utilized to carry oxygen as hemoglobin replacements. After permitting sufficient time for incubation, a whole body MRI is carried out using an apparatus such as one of those described by Pykett (1982) *Scientific American,* 246:78-88 to locate and image activated leukocytes.

Information obtained from evaluating an aLFA-1-binding protein, e.g., a binding protein described herein, can be recorded on machine-compatible media, e.g., computer readable or computer accessible media. The information can be stored as a computer representation, e.g., in a database (e.g., in the case of imaging using a binding protein, a database of images for one or a plurality of subjects). The term "computer representation" refers to information which is in a form that can be manipulated by a computer. The act of storing a computer representation refers to the act of placing the information in a form suitable for manipulation by a computer.

Kits

Also within the scope of the invention are kits that include a composition described herein, e.g., a composition that contains an aLFA-1-binding protein. In one embodiment, the kit includes (a) a composition that includes the aLFA-1-binding protein, and, optionally, (b) informational material. The informational material can be descriptive, instructional, marketing or other material that relates to the methods described herein and/or the use of the compound for the methods described herein, e.g., a treatment, prophylactic, or diagnostic use. For example, the informational material describes methods for administering the composition to treat a disorder, e.g., an inflammatory disorder, a disorder characterized by excessive LFA-1 activity, or other LFA-1 mediated disorder.

In one embodiment, the informational material can include instructions to administer the compound in a suitable manner, e.g., in a suitable dose, dosage form, or mode of administration (e.g., a dose, dosage form, or mode of administration described herein). In another embodiment, the informational material can include instructions for identifying a suitable subject, e.g., a human, e.g., a human having, or at risk for an inflammatory disorder, a disorder characterized by excessive LFA-1 activity, or a LFA-1 mediated disorder. The informational material can include information about production of the compound, molecular weight of the compound, concentration, date of expiration, batch or production site information, and so forth. The informational material of the kits is not limited in its form. Information about the compound can include structural information, e.g., amino acid sequence, tradename, FDA approved name, antibody isotype, and so forth. In many cases, the informational material, e.g., instructions, is provided in printed matter, e.g., a printed text, drawing, and/or photograph, e.g., a label or printed sheet. However, the informational material can also be provided in other formats, such as computer readable material, video recording, or audio recording. In another embodiment, the informational material of the kit is a link or contact information, e.g., a physical address, email address, hyperlink, website, or telephone number, where a user of the kit can obtain substantive information about the compound and/or its use in the methods described herein. The informational material can also be provided in any combination of formats.

In addition to the composition that includes the aLFA-1-binding protein, the composition itself can include other ingredients, such as a solvent or buffer, a stabilizer or a preservative, and/or a second agent for treating a condition or disorder described herein, e.g., an inflammatory disorder, a disorder characterized by excessive LFA-1 activity, or a LFA-1 mediated disorder. Alternatively, such other ingredients can be included in the kit, but in different compositions or containers than the composition that includes the aLFA-1-binding protein. In such embodiments, the kit can include instructions for admixing the compound and the other ingredients, or for using the compound together with the other ingredients.

The composition that includes the aLFA-1-binding protein can be provided in any form, e.g., liquid, dried or lyophilized form. The composition can be substantially pure and/or sterile. When the composition that includes the aLFA-1-binding protein is provided in a liquid solution, the liquid solution preferably is an aqueous solution, with a sterile aqueous solution being preferred. When the composition that includes the aLFA-1-binding protein is provided as a dried form, reconstitution generally is by the addition of a suitable solvent. The solvent, e.g., sterile water or buffer, can optionally be provided in the kit.

The kit can include one or more containers for the composition that includes the aLFA-1-binding protein. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the aLFA-1-binding protein. For example, the kit includes a plurality of syringes, ampules, foil packets, or blister packs, each containing a single unit dose of the compound. The containers of the kits can be air tight, waterproof (e.g., impermeable to changes in moisture or evaporation), and/or light-tight.

Kits can be provided that include an aLFA-1-binding antibody and instructions for diagnostic, e.g., the use of the aLFA-1-binding protein (e.g., antibody or antigen-binding fragment thereof, or other polypeptide or peptide) to detect aLFA-1, in vitro, e.g., in a sample, e.g., a biopsy or cells from a patient having a disorder described herein, or in vivo, e.g., by imaging a subject. The kit can further contain a least one additional reagent, such as a label or additional diagnostic agent. For in vivo use the ligand can be formulated as a pharmaceutical composition.

The following invention is further illustrated by the following examples, which should not be construed as limiting.

EXAMPLES

The D2-57 Fab was isolated by depleting a Fab phage display library on the low affinity wild type purified I-domain protein followed by positive selection on high affinity locked open form I-domain LFA-1 protein. D2-57 Fab binds to the high affinity locked open state of purified I-domain protein in the presence, but not absence of magnesium. It does not bind significantly to the low affinity locked closed state of purified I-domain protein in either the presence or absence of magnesium.

In the presence of magnesium, D2-57 Fab binds to cells expressing whole LFA-1 in which the α subunit contains an I-domain in the high affinity locked open state ("HA cells"), but not when magnesium is absent. D2-57 also binds in the presence of magnesium to activated wild-type LFA-1 protein expressed on cells. D2-57 does not bind to cells expressing whole LFA-1 when the α subunit contains an I-domain in the low affinity locked closed state ("LA cells"). In contrast, MHM24 binds to both HA and LA cells.

The reformatted full IgG1, when tested with cells, has the same binding specificities as the Fab form.

Phage that display the P1-G10 in a Fab format bind to the high affinity locked open form I-domain LFA-1 protein in the presence or absence of magnesium, but do not bind to the low affinity locked closed state.

The C1-54 Fab binds to both the high affinity locked open form I-domain LFA-1 protein and the low affinity locked closed state, but preferentially binds to the open form in the presence of magnesium.

The following is a comparison of the variable region of exemplary antibodies:

```
                        VARIABLE REGION - LIGHT CHAINS

FR1-L                        CDR1-L         FR2-L        CDR2-L
D2-57   QDIQMTQSPSSLSASVGDRVTITC    RASQSIGSYLN    WYQQKTGKAPKALIY    AASSLQS

C1-54   QDIQMTQSPATLSVSPGERVTLSC    TASQSVDSNLA    WYQQKPGQAPRLLVY    GASTRAT

P1-G10  QSV.LTQ.PPSVSVSPGQTASVTC    SGDALGQKYAS    WYQQKPGQSPVLVIF    QDSKRPS

FR3-L                      CDR3-L         FR4-L
D2-57   GVPSRFSGSGSGTDFTLTISSLQLEDFATYYC   QQSYSTP..S    FGQGTKVEIKRT

C1-54   GVPARFSGSGSGTAFTLTIDSLQSEDFAVYYC   QQYNKWPPYS    FGQGTKLEIKRT

P1-G10  GIPERFSGSNSGNTATLTISGTQAVDEADYYC   QAWDTT.AYV    FGTGTKVTVL

SEQ ID NO: 33, 34, and 35 respectively.

VARIABLE REGION - HEAVY CHAINS

FR1-H                        CDR1-H    FR2-H
D2-57   EVQLLESGGGLVQPGGSLRLSCAASGFTFS    RYVMW    WVRQAPGKGLEWVS

C1-54   EVQLLESGGGLVQPGGSLRLSCAASGFTFS    HYGMS    WVRQAPGKGLEWVS

P1-G10  EVQLLESGGGLVQPGGSLRLSCAASGFTFS    HYSMQ    WVRQAPGKGLEWVS

CDR2-H
D2-57   YIWPSGGNTYYADSVKG

C1-54   VISPSGGRTLYADSVKG

P1-G10  YIGSSGGNTYYADSVKG

FR3-H                           CDR3-H         FR4-H
D2-57   RFTISRDNSKNTLYLQMNSLRAEDTAVYYCAS   SYDFWSNAFDI    WGQGTMVTVSS

C1-54   RFTISRDNSKNTLYLQMNSLRAEDTAVYYCAK   HYSY...AMDV    WGQGTTVTVSS

P1-G10  RFTISRDNSKNTLYLQMNSLRAEDTAVYYCAR   G.TYNTSPFDY    WGQGTLVTVSS

SEQ ID NO: 36, 37, and 38 respectively.

VARIABLE REGION -LIGHT CHAINS (Nucleic Acid)

FR1-L
D2-57   CAAGACATCCAGATGACCCAGTCTCCATCCTCCCTGTCTGCATCTGTAGGAGACAGAGTCAC

C1-54   CAAGACATCCAGATGACCCAGTCTCCAGCCACCCTGTCTGTGTCTCCAGGGGAAAGAGTCAC

P1-G10  CAGAGCGTCTTGA......CTCAGCCACCCTCAGTGTCCGTCTCCCCAGGACAGACAGCCAG

CDR1-L
D2-57   CATCACTTGC  CGGGCAAGTCAGAGCATTGGCAGCTACTTAAAC  TGGTATCAGCAGAAAAC

C1-54   CCTCTCCTGC  ACGGCCAGTCAGAGTGTTGACAGCAACTTAGCC  TGGTATCAGCAAAAACC
```

-continued

```
P1-G10 CGTCACTTGC TCTGGAGATGCATTGGGACAAAAATATGCTTCC TGGTATCAACAGAAGCC

FR2-L                        CDR2-L
D2-57  AGGGAAAGCCCCTAAGGCCCTGATCTAT GCTGCATCCAGTTTGCAAAGT GGGGTCCCATC

C1-54  TGGCCAGGCTCCCAGACTCCTCGTCTAT GGTGCATCCACTAGGGCCACT GGTGTCCCAGC

P1-G10 AGGCCAGTCCCCTGTACTGGTCATCTTT CAAGATTCCAAGCGGCCCTCA GGGATCCCTGA

FR3-L
D2-57  AAGGTTCAGTGGCAGTGGGTCTGGGACAGATTTCACTCTCACCATCAGTAGTCTGCAACTTG

C1-54  CAGGTTCAGTGGCAGTGGGTCTGGGACAGCGTTCACTCTCACCATCGACAGCCTGCAGTCTG

P1-G10 GCGGTTCTCTGGCTCCAATTCTGGGAACACAGCCACTCTGACCATCAGCGGGACCCAGGCTG

CDR3-L
D2-57  AAGATTTTGCAACTTACTACTGT CAACAGAGTTACA......GTACCCCCTCG TTCGGCC

C1-54  AAGATTTTGCAGTTTATTACTGT CAGCAGTATAATAAGTGGCCTCCGTACTCC TTTGGCC

P1-G10 TGGATGAGGCCGACTATTATTGT CAGGCGTGGGACA...CTACAGCTTATGTC TTCGGAA

FR4-L
D2-57  AAGGGACCAAGGTGGAAATCAAA

C1-54  AGGGGACCAAGCTGGAGATCAAG

P1-G10 CTGGGACCAAGGTCACCGTCCTA

SEQ ID NO: 39, 40, and 41 respectively.
```

```
         VARIABLE REGION - HEAVY CHAINS (Nucleic Acid)
              FR1-H
D2-57  GAAGTTCAATTGTTAGAGTCTGGTGGCGGTCTTGTTCAGCCTGGTGGTTCTTTACGTCTT

C1-54  GAAGTTCAATTGTTAGAGTCTGGTGGCGGTCTTGTTCAGCCTGGTGGTTCTTTACGTCTT

P1-G10 GAAGTTCAATTGTTAGAGTCTGGTGGCGGTCTTGTTCAGCCTGGTGGTTCTTTACGTCTT

CDR1-H
D2-57  TCTTGCGCTGCTTCCGGATTCACTTTCTCT CGTTACGTTATGTGG TGGGTTCGCCAAGCT

C1-54  TCTTGCGCTGCTTCCGGATTCACTTTCTCT CATTACGGTATGTCT TGGGTTCGCCAAGCT

P1-G10 TCTTGCGCTGCTTCCGGATTCACTTTCTCT CATTACTCTATGCAG TGGGTTCGCCAAGCT

FR2-H                        CDR2-H
D2-57  CCTGGTAAAGGTTTGGAGTGGGTTTCT TATATCTGGCCTTCTGGTGGCAATACTTATTAT

C1-54  CCTGGTAAAGGTTTGGAGTGGGTTTCT GTTATCTCTCCTTCTGGTGGCCGTACTCTTTAT

P1-G10 CCTGGTAAAGGTTTGGAGTGGGTTTCT TATATCGGTTCTTCTGGTGGCAATACTTATTAT

FR3-H
D2-57  GCTGACTCCGTTAAAGGT CGCTTCACTATCTCTAGAGACAACTCTAAGAATACTCTCTAC

C1-54  GCTGACTCCGTTAAAGGT CGCTTCACTATCTCTAGAGACAACTCTAAGAATACTCTCTAC

P1-G10 GCTGACTCCGTTAAAGGT CGCTTCACTATCTCTAGAGACAACTCTAAGAATACTCTCTAC

FR3-H (contd)
D2-57  TTGCAGATGAACAGCTTAAGGGCTGAGGACACTGCAGTCTACTATTGTGCGAG TAGCTAC

C1-54  TTGCAGATGAACAGCTTAAGGGCTGAGGACACTGCAGTCTACTATTGTGCGAA .......

P1-G10 TTGCAGATGAACAGCTTAAGGGCTGAGGACACTGCAGTCTACTATTGTGCGAG AGGGACC

CDR3-H                          FR4-H
D2-57  GATTTTTGGAGTAATGCTTTTGATATC TGGGGCCAAGGGACAATGGTCACCGTCTCAAGC

C1-54  ..ACATTACTCCTACGCTATGGACGTC TGGGGCCAAGGGACCACGGTCACCGTCTCAAGC

P1-G10 ...TATAACACCTCCCCCTTTGACTAC TGGGGCCAGGGAACCCTGGTCACCGTCTCAAGC

SEQ ID NO: 42, 43, and 44 respectively.
```

Exemplary ELISA data obtained with some of the described antibodies is as follows:

TABLE 2

Exemplary ELISA data

| Isolate number | HA with $Mg^{2+}$ | HA w/o $Mg^{2+}$ | LA with $Mg^{2+}$ | LA w/o $Mg^{2+}$ |
|---|---|---|---|---|
| Control # | 0.15 | 0.10 | 0.13 | 0.07 |
| C1-54 | 1.02 | 0.55 | 1.17 | 0.49 |
| D2-57 | 0.68 | 0.09 | 0.13 | 0.07 |
| P1-G10 | 0.87 | 1.06 | 0.16 | 0.08 |
| Control #2 | 0.17 | 0.10 | 0.14 | 0.07 |
| no phage | 0.10 | 0.08 | 0.08 | 0.06 |
| P1-G10, no cells | 0.05 | 0.06 | 0.05 | 0.05 |
| blank | 0.05 | 0.05 | 0.05 | 0.05 |

HA indicates the high affinity open form. LA indicates the low affinity closed form of LFA-1. Control #1 refers to a phage that binds to a different target. Control #2 is another protein that binds to a different target. Numbers are in arbitrary units.

Germlining D2-57

The D2-57 light chain was compared to a human germline sequence. D2-57 variants that include one or more alterations that increase the number of similarities to a germline sequence (e.g., VKI-O2::JK1) can be used. For example, an antibody can include a D2-57 light chain with one or more of the following substitutions, e.g., one, two, three, four, five, or six of the following substitutions (or insertion), e.g., at positions: G30S, L40P, A46L, L80P, W96ins, and S97T. In many cases it is preferable that A46 is maintained as an alanine. For example, the antibody can include an insertion that provides W96.

The C1-54 light chain was compared with a human germline sequence, e.g., VKIII-L2. An antibody can include a C1-54 light chain with one or more of the following substitutions, e.g., between one and eleven, two and five, or six and eleven of the following substitutions (or deletion), e.g., at positions: D1E, Q3V, V19A, T24R, D30S, V48I, V58I, A70E, D76S, K93N, and P95a☐.

The P1-G10 light chain was compared with a human germline sequence, e.g., VL2-1 aka VL3 11-7. An antibody can include a P1-G10 light chain with one or more of the following substitutions, e.g., between one and twelve, two and five, or six and twelve of the following substitutions (or insertion), e.g., at positions: Q1S, S2Y, V3E, V21I, A28K, Q31aD, S34C, F49Y, V81M, T93S, T94S, and A95a(ins).

A vg3-23 related heavy chain can include one or more of the following exemplary sequences in the JH region:

```
JH1
---AEYFQHWGQGTLVTVSS            (SEQ ID NO: 45)
JH2
---YWYFDLWGRGTLVTVSS            (SEQ ID NO: 46)
JH3
-----AFDIWGQGTMVTVSS            (SEQ ID NO: 47)
JH4
-----YFDYWGQGTLVTVSS  FDYWGQGTLVTVSS  (SEQ ID NO: 48)
JH5
----NWFDPWGQGTLVTVSS            (SEQ ID NO: 49)
JH6
YYYYYGMDVWGQGTTVTVSS            (SEQ ID NO: 50)
```

An antibody can include a D2-57 heavy chain with one or more of the following substitutions, e.g., between one and nine, two and five, or six and nine of the following substitutions, e.g., at positions: R31S, V33A, W35S, Y50A, W52S, P52aG, N56S, S94R, A99Y, I102Y, and M108L. Accordingly, the heavy chain variable domain can have fewer than ten, seven, six, or five differences relative to the germline sequence V3-23.

An antibody can include a C1-54 heavy chain with one or more of the following substitutions, e.g., between one and seven, e.g., one, two, three, four, five, six, or seven of the following substitutions, e.g., at positions: H31S, G33A, V50A, P52aG, R56S, L58Y, and K94R. Accordingly, the heavy chain variable domain can have fewer than seven, six, or five differences relative to the germline sequence V3-23.

An antibody can include a P1-G10 heavy chain with one or more of the following substitutions, e.g., between one and seven, e.g., one, two, three, four, five, six, or seven of the following substitutions, e.g., at positions: H31S, S33A, Q35S, Y50A, G52S, S52aG, and N56S. Accordingly, the heavy chain variable domain can have fewer than ten, seven, six, or five differences relative to the germline sequence V3-23.

Affinity Maturation of HC CDR3 of D2-57

Variants of the antibody were made that include variations in the CDR3 region of the heavy chain variable domain. From such variants, clones were selected that bound to the high affinity (HA) I-domain, e.g., using the following conditions: 7.5 min binding time, 20 nM HA I-domain, and 16 h incubation with 1 µM D2-57 IgG1 antibody. Some exemplary variants that bound to the LFA-1 I-domain in the activated conformation have the following sequences in the CDR3 region of the heavy chain, from residues 96 to 120 of the DX-2001 sequence:

```
          <---CDR3--->
            12345678901
E05
96  CASSYDLWSNAFDKWGQGTMVTVSS  120 from SEQ ID NO: 53

A04
96  CASSYDLWSYAFEIWGQGTMVTVSS  120 from SEQ ID NO: 55

C09
96  CASSYDYWSNAFDSWGQGTMVTVSS  120 from SEQ ID NO: 51

F07
96  CASSFDFWSNAFDMWGQGTMVTVSS  120 from SEQ ID NO: 52

B04
96  CASSYDFWSNAYANWGQGTMVTVSS  120 from SEQ ID NO: 56

F05
96  CANSYDFRSNAFAVWGQGTMVTVSS  120 from SEQ ID NO: 54

C02
96  CANSFDFWSNAFELWGQGTMVTVSS  120 from SEQ ID NO: 57
    **.*:*  *  *:  **********
```

More complete sequences of these heavy chain variable domains are as follows:

The C09 variant includes:

```
                                  (SEQ ID NO: 51)
EVQLLESGGGLVQPGGSLRLSCAASGFTFSRYVMWWVRQAPGKGLEW

VSYIWPSGGNTYYADSVKGRFTISRDNSKNTLYLQMNSLRAEDTAVYYCA

SSYDYWSNAFDSWGQGTMVTVSS.
```

The F07 variant includes:

(SEQ ID NO: 52)
EVQLLESGGGLVQPGGSLRLSCAASGFTFSRYVMWWVRQAPGKGLEW
VSYIWPSGGNTYYADSVKGRFTISRDNSKNTLYLQMNSLRAEDTAVYYCA
SSFDFWSNAFDMWGQGTMVTVSS.

The E05 variant includes:

(SEQ ID NO: 53)
EVQLLESGGGLVQPGGSLRLSCAASGFTFSRYVMWWVRQAPGKGLEW
VSYIWPSGGNTYYADSVKGRFTISRDNSKNTLYLQMNSLRAEDTAVYYCA
SSYDLWSNAFDKWGQGTMVTVSS.

The F05 variant includes:

(SEQ ID NO: 54)
EVQLLESGGGLVQPGGSLRLSCAASGFTFSRYVMWWVRQAPGKGLEW
VSYIWPSGGNTYYADSVKGRFTISRDNSKNTLYLQMNSLRAEDTAVYYCA
NSYDFRSNAFAVWGQGTMVTVSS.

The A04 variant includes:

(SEQ ID NO: 55)
EVQLLESGGGLVQPGGSLRLSCAASGFTFSRYVMWWVRQAPGKGLEW
VSYIWPSGGNTYYADSVKGRFTISRDNSKNTLYLQMNSLRAEDTAVYYCA
SSYDLWSYAFEIWGQGTMVTVSS.

The B04 variant includes:

(SEQ ID NO: 56)
EVQLLESGGGLVQPGGSLRLSCAASGFTFSRYVMWWVRQAPGKGLEWVSY
IWPSGGNTYYADSVKGRFTISRDNSKNTLYLQMNSLRAEDTAVYYCASSY
DFWSNAYANWGQGTMVTVSS.

The C02 variant includes:

(SEQ ID NO: 57)
EVQLLESGGGLVQPGGSLRLSCAASGFTFSRYVMWWVRQAPGKGLEWVSY
IWPSGGNTYYADSVKGRFTISRDNSKNTLYLQMNSLRAEDTAVYYCANSF
DFWSNAFELWGQGTMVTVSS.

Without being bound by theory, the aspartic acid at position 3 in CDR3 may interact with an $Mg^{2+}$ ion bound to I-domain. This aspartic acid was conserved 75 of 80 different affinity matured Fabs.

ICAM-1 blocking assay using HA cells with D2-57 (DX-1998.2) and 84 different sFab isolates were performed. HA and LA cells were cultured in RPMI supplemented with 10% FCS, 100 U/ml penicillin-streptomycin, 2 mM L-glutamine and 0.1 mM MEM non-essential amino acid at 37° C., 5% $CO_2$. Cells were harvested, washed once with HBS containing 10 mM EDTA followed by two washings with HBS. Cells were resuspended in activating (HBS, 10 mM $MgCl_2$, 2 mM EGTA) or inactivating buffer (HBS, 2 mM $MgCl_2$, 2 mM $CaCl_2$) as indicated in the protocol. Myeloma IgG was added to block the Fc receptors. ICAM-1/SV-PE complex at a 4:1 ratio was added after the antibody addition. Cells were washed and resuspended in the staining solution after 30 mins. FACS analysis was done using the GUAVA EXPRESS™ protocol.

In one assay using soluble Fabs, the $IC_{50}$s for three of the affinity matured antibodies were 8.6±3.1 nM, 7.6±2.8 nM, and 6.5±2.6 nM, relative to 11.5±4.8 nM for D2-57 in soluble Fab form as determined in parallel.

DX-2001

The following is an exemplary nucleic acid sequence that encodes the light chains of DX-2001-light chain (variable and constant):

(SEQ ID NO: 58)
GACATCCAGATGACCCAGTCTCCATCCTCCCTGTCTGCATCTGTAGG
AGACAGAGTCACCATCACTTGCCGGGCAAGTCAGAGCATTGGCAGCTACT
TAAACTGGTATCAGCAGAAACCAGGGAAAGCCCCTAAGGCCCTGATCTAT
GCTGCATCCAGTTTGCAAAGTGGGGTCCCATCAAGGTTCAGTGGCAGTGG
GTCTGGGACAGATTTCACTCTCACCATCAGTAGTCTGCAACCTGAAGATT
TTGCAACTTACTACTGTCAACAGAGTTACAGTACCCCCTCGTTCGGCCAA
GGGACCAAGGTGGAAATCAAAAGAACTGTGGCTGCACCATCTGTCTTCAT
CTTCCCGCCATCTGATGAGCAGTTGAAATCTGGAACTGCCTCTGTTGTGT
GCCTGCTGAATAACTTCTATCCCAGAGAGGCCAAAGTACAGTGGAAGGTG
GATAACGCCCTCCAATCGGGTAACTCCCAGGAGAGTGTCACAGAGCAGGA
CAGCAAGGACAGCACCTACAGCCTCAGCAGCACCCTGACGCTGAGCAAAG
CAGACTACGAGAAACACAAAGTCTACGCCTGCGAAGTCACCCATCAGGGC
CTGAGCTCGCCCGTCACAAAGAGCTTCAACAGGGGAGAGTGT.

The following is an exemplary nucleic acid sequence that encodes the light chains of DX-2001-heavy chain (variable and constant):

(SEQ ID NO: 59)
GAAGTTCAATTGTTAGAGTCTGGTGGCGGTCTTGTTCAGCCTGGTGG
TTCTTTACGTCTTTCTTGCGCTGCTTCCGGATTCACTTTCTCTCGTTACG
TTATGTGGTGGGTTCGCCAAGCTCCTGGTAAAGGTTTGGAGTGGGTTTCT
TATATCTGGCCTTCTGGTGGCAATACTTATTATGCTGACTCCGTTAAAGG
TCGCTTCACTATCTCTAGAGACAACTCTAAGAATACTCTCTACTTGCAGA
TGAACAGCTTAAGGGCTGAGGACACTGCAGTCTACTATTGTGCGAGTAGC
TACGATTTTTGGAGTAATGCTTTTGATATCTGGGGCCAAGGGACAATGGT
CACCGTCTCAAGCGCCTCCACCAAGGGCCCATCGGTCTTCCCGCTAGCGC
CCTGCTCCAGGAGCACCTCCGAGAGCACAGCCGCCTGGGCTGCCTGGTC
AAGGACTACTTCCCCGAACCGGTGACGGTGTCGTGGAACTCAGGCGCCCT
GACCAGCGGCGTCCACACCTTCCCGGCTGTCCTACAGTCCTCCGGACTCT
ACTCCCTCAGCAGCGTAGTGACCGTGCCCTCCAGCAGCTTGGGCACGAAG
ACCTACACCTGCAACGTAGATCACAAGCCCAGCAACACCAAGGTGGACAA
GAGAGTTGAGTCCAAATATGGTCCCCCATGCCCATCATGCCCAGCACCTG
AGTTCCTGGGGGGACCATCAGTCTTCCTGTTCCCCCCAAAACCCAAGGAC
ACTCTCATGATCTCCCGGACCCCTGAGGTCACGTGCGTGGTGGTGGACGT

-continued
GAGCCAGGAAGACCCCGAGGTCCAGTTCAACTGGTACGTGGATGGCGTGG

AGGTGCATAATGCCAAGACAAAGCCGCGGGAGGAGCAGTTCAACAGCACG

TACCGTGTGGTCAGCGTCCTCACCGTCCTGCACCAGGACTGGCTGAACGG

CAAGGAGTACAAGTGCAAGGTCTCCAACAAAGGCCTCCCGTCCTCCATCG

AGAAAACCATCTCCAAAGCCAAAGGGCAGCCCCGAGAGCCACAGGTGTAC

ACCCTGCCCCCATCCCAGGAGGAGATGACCAAGAACCAGGTCAGCCTGAC

CTGCCTGGTCAAAGGCTTCTACCCCAGCGACATCGCCGTGGAGTGGGAGA

GCAATGGGCAGCCGGAGAACAACTACAAGACCACGCCTCCCGTGCTGGAC

TCCGACGGCTCCTTCTTCCTCTACAGCAGGCTAACCGTGGACAAGAGCAG

GTGGCAGGAGGGGAATGTCTTCTCATGCTCCGTGATGCATGAGGCTCTGC

ACAACCACTACACAGAAGAGCCTCTCCCTGTCTCTGGGTAAATGA.

The following is an exemplary amino acid sequence of a DX-2001-light chain (variable and constant):

(SEQ ID NO: 60)
DIQMTQSPSSLSASVGDRVTITCRASQSIGSYLNWYQQKPGKAPKALIY

AASSLQSGVPSRFSGSGSGTDFTLTISSLQPEDFATYYCQQSYSTPSFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

The following is an exemplary amino acid sequence of a DX-2001-heavy chain (variable and constant) IgG4:

(SEQ ID NO: 61)
EVQLLESGGGLVQPGGSLRLSCAASGFTFSRYVMWWVRQAPGKGLEW

VSYIWPSGGNTYYADSVKGRFTISRDNSKNTLYLQMNSLRAEDTAVYYCA

SSYDFWSNAFDIWGQGTMVTVSSASTKGPSVFPLAPCSRSTSESTAALGC

LVKDYFPEPVTVSWNSGALTSGVHTFPAVLQSSGLYSLSSVVTVPSSSLG

TKTYTCNVDHKPSNTKVDKRVESKYGPPCPSCPAPEFLGGPSVFLFPPKP

KDTLMISRTPEVTCVVVDVSQEDPEVQFNWYVDGVEVHNAKTKPREEQFN

STYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSL

GK.

The changes in the light chain include altering position 40 from Thr to Pro in framework 2 and/or altering position 80 from Leu to Pro in framework 3. Preferably, position 46 in framework 2 is Ala (rather than the germline Leu).

DX2001 (a germlined variant of D2-57, IgG4) binds to a small percentage of PBMCs (peripheral blood mononuclear cells) that are in $MgCl_2$/EGTA conditions. The binding is drastically enhanced by 20-min treatment with PMA (10 ng/ml) or DTT (500 M). Treatment with PMA or DTT induces high affinity state LFA-1. ICAM-1 has similar binding properties to PBMCs.

The PKC inhibitors, GF109203X and staurosporine, blocked PMA-induced binding of DX-2001 to PBMCs.

Species Specificity

Whole blood from healthy animals (rat, sheep, rabbit, dog, rhesus monkey, cynomologus monkey and chimpanzee) were obtained from Valley Biomedical Products and Services, Inc. PBMCs were isolated from whole blood and cultured in low adherent 6-well plates overnight in RPMI 1640 with 10% FBS, 1× Pen/Strep. PBMCs were harvested, washed once with Hanks' Balanced Salt Solution (HBSS) 1×, 20 mM HEPES buffer containing 10 mM EDTA, and then twice with HBS. Cells were resuspended in HBSS at $2 \times 10^6$ cells/ml, 100 µl aliquots per well were added into 96-well plates (Costar round bottom). After spinning down, cell pellets were resuspended in 50 µl activating buffer (HBSS, 10 mM $MgCl_2$, 2 mM EGTA) or inactivating buffer (HBSS, 2 mM $CaCl_2$, 2 mM $MgCl_2$). For certain wells, PMA or DTT was added to a final concentration of 10 ng/ml or 500 µM, respectively. Cells were then incubated at 37° C. for 20 minutes. Cells were incubated with DX-2001 (10 µg/ml) or a negative control antibody Fc-A2 (anti-CD44-Fc $IgG_4$ 10 µg/ml).

Antibodies that recognized CD-11a from the particular species (human, sheep, dog, rat, rabbit) (1:100 dilution) were used as positive controls. After incubation at room temperature for 30 minutes with gentle rocking, cells were washed twice with 220 µl/well HBSS containing 0.05% $NaN_3$, and stained with PE-labeled secondary antibody at 100 µl/well (anti-Human-IgG-PE, code: 709-116-149, Jackson Immunoresearch, and anti-mouse-IgG-PE, code: 115-115-164. Jackson Immunoresearch), 1:200 diluted in HBSS. Cells were incubated at 4° C. for 30 minutes, then washed twice with 220 µl/well HBSS containing 0.05% $NaN_3$, resuspended in 200 µl/well HBSS and analyzed using the GUAVA EXPRESS™ protocol (Guava Technologies, Inc., Hayward Calif.).

DX-2001 demonstrated good binding to chimpanzee PBMCs, at same extent as in human PBMCs. Binding to cells of these species is drastically increased after PMA treatment. DX-2001 demonstrated minimal binding to cynomologus monkey, rat and sheep PBMCs. The binding in activating conditions was increased slightly after PMA treatment. However, the binding level is much less than in human and chimpanzee PBMCs. DX-2001 does not show significant binding to rhesus monkey, dog and rabbit PBMCs. (summarized in Table 3).

TABLE 3

| Species | Cells | No Treatment | PMA | DTT |
| --- | --- | --- | --- | --- |
| Human | PBMCs | ++ | ++++ | +++++++ |
| Chimpanzee | PBMCs | ++ | ++++ | ++ |
| Cyn. monkey | PBMCs | + | ++~++++ | ++~+++ |
| Rhesus monkey | PBMCs | − | − | ND |
| Dog | PBMCs | − | − | ND |
| Rabbit | PBMCs | − | − | ND |
| Rat | PBMCs | + | ++ | ND |
| Sheep | PBMCs | + | ++ | ND |
| Mouse | EL4 Cell line | − | ND | ND |

The binding intensity of DX-2001 in hPBMCs without PMA was defined as "++"; after PMA treatment defined as "++++"; DTT treatment defined as "++++++"."−": no binding. N.D.: not determined. The bindings of all PBMCs from seven species were compared with hPBMCs binding.

The ability of D2-57 IgG to inhibit I-CAM binding to HA cells (i.e., cells expressing LFA-1 locked in the high affinity form) was evaluated and compared to MHM24 IgG in parallel. $IC_{50}$ values were determined using GUAVA™ analysis. In one experiment, the $IC_{50}$ values for D2-57 and MGM24 IgG were 0.18±0.02 and 0.24±0.04 nM, respectively. In another experiment, the $IC_{50}$ values for D2-57 and MGM24 IgG were 0.59±0.1 nM (first lot of D2-57 IgG) and 0.62±0.16 nM (second lot of D2-57 IgG) and 1.8±0.8 nM (MHM24) respectively. In still another experiment, the $IC_{50}$ values for D2-57 and MGM24 IgG were 0.24±0.02 and 0.59±0.13 nM, respectively. In still another experiment, the $IC_{50}$ values for D2-57 and MGM24 IgG were 0.68±0.2 and 2.4±0.8 nM, respectively. The pattern that emerges from these experiments is that, within the margin of experimental error, D2-57 has an $IC_{50}$ that is as good or better than MHM24 in this particular assay set-up.

The ability D2-57 IgG to inhibit I-CAM binding to human PBMCs was also evaluated. The average of four experiments indicated that the $IC_{50}$ values for D2-57 and MGM24 IgG were 0.54±0.44 and 0.33±0.17 nM, respectively.

D2-57 not only blocked ICAM-1 binding, but also could block PHA-stimulated lymphocyte proliferation. For details on the PHA-stimulated lymphocyte proliferation assay, see, e.g., Vermot Desroches et al., Scand. J. Immunol. 1991, 33: 277-286. The assay evaluates the effect of D2-57 (DX-1999) on PHA (phytohaemagglutinin)-stimulated lymphocyte proliferation assay. In brief, PBMCs were stimulated with PHA at 1 µg/ml in the presence of serially diluted IgG. After stimulation for three days, cells were analyzed for proliferation by BrdU chemiluminescence assay.

D2-57, in IgG form, also blocked HA cell binding to keratinocytes when applied at a concentration of 6.7 nM. $IC_{50}$ value for inhibition by D2-57 was about 1 nM. For details on the keratinocyte adhesion assay, see, e.g., Werther W. A. et al., J. Immunol. 1996, 157: 4986-4995. The assay evaluates the effect of anti-LFA-1 IgG D2-57 on adhesion of HA cells (HA-expressing K562 cells) to keratinocytes. In brief, HA cells were labeled with calcein AM, incubated with serially diluted testing IgG, and added to keratinocyte monolayer. After incubation, the monolayer was washed extensively and fluorescence was measured using a fluorescent plate reader.

Additional antibody selections were done to identify affinity matured variants of D2-57. Varied antibodies were bound to the I-domain locked in the high affinity conformation, and then eluted with 1 µM D2-57 IgG1 antibody. Three antibodies that had improved affinity showed $IC_{50}$ values of 083±55, 0.74±0.17, and 0.54±0.33, based on an average of three experiments.

Other embodiments of the invention are within the following claims.

What is claimed:

1. An isolated antibody comprising an immunoglobulin heavy chain (HC) variable domain and an immunoglobulin light chain (LC) variable domain, wherein the HC variable domain and the LC variable domain form an antigen binding site that binds to an activated conformation of LFA-1, wherein the antibody comprises:

(i) a heavy chain variable domain that comprises (a) a CDR1 that comprises RYVMW (SEQ ID NO:1); (b) a CDR2 that comprises YIWPSGGNTYYADSVKG (SEQ ID NO:2); and (c) a CDR3 that comprises a sequence selected from the group consisting of SEQ ID NO:3, SEQ ID NO:51, SEQ ID NO:52, SEQ ID NO:53, SEQ ID NO:54, SEQ ID NO:55, SEQ ID NO:56 and SEQ ID NO:57; and a light chain variable domain that comprises (d) a CDR1 that comprises RASQSIGSYLN (SEQ ID NO:7); (e) a CDR2 that comprises AASSLQS (SEQ ID NO:8); and (f) a CDR3 that comprises QQSYSTPS (SEQ ID NO:9); or (ii) a heavy chain variable domain that comprises SEQ ID NO:23, SEQ ID NO:25, SEQ ID NO:27, or SEQ ID NO:29; and a light chain variable domain that comprises SEQ ID NO:22, SEQ ID NO:24, SEQ ID NO:26, or SEQ ID NO:28; or (iii) a heavy chain variable domain that comprises a sequence encoded by a nucleic acid that hybridizes under high stringent conditions to the complement of the full length of SEQ ID NO:42, SEQ ID NO:43, or SEQ ID NO:44; and a light chain variable domain that comprises a sequence encoded by a nucleic acid that hybridizes under high stringent conditions to the complement of the full length of SEQ ID NO:39, SEQ ID NO:40, or SEQ ID NO:41; or (iv) an antibody selected from the group consisting of
  a) an immunoglobulin heavy chain variable domain sequence comprising SEQ ID NO:23, and an immunoglobulin light chain variable domain sequence comprising SEQ ID NO:22;
  b) an immunoglobulin heavy chain variable domain sequence comprising SEQ ID NO:25, and an immunoglobulin light chain variable domain sequence comprising SEQ ID NO:24;
  c) an immunoglobulin heavy chain variable domain sequence comprising SEQ ID NO:27, and an immunoglobulin light chain variable domain sequence comprising SEQ ID NO:26; and
  d) an immunoglobulin heavy chain variable domain sequence comprising
  SEQ ID NO:29, and an immunoglobulin light chain variable domain sequence comprising SEQ ID NO:28;
for binding to activated LFA-1.

2. The antibody of claim 1 that comprises the CDR regions of (i) and (ii).

3. The antibody of claim 1 wherein the heavy and light chain variable domain sequences comprise, respectively, SEQ ID NO:23 and SEQ ID NO:22.

4. The antibody of claim 1 wherein at least the protein framework regions are identical to the framework regions of SEQ ID NO:33 (light chain) and SEQ ID NO:36 (heavy chain); SEQ ID NO:34 (light chain) and SEQ ID NO:37 (heavy chain); or SEQ ID NO:35 (light chain) and SEQ ID NO:38 (heavy chain).

5. The antibody of claim 1 wherein the CDR3 of the heavy chain variable domain comprises SYDFWSNAFDI (SEQ ID NO:3).

6. The antibody of claim 1 that is not immunogenic in humans.

7. The antibody of claim 1 that is a full length IgG antibody.

8. The antibody of claim 1 that is an antigen binding fragment of an antibody, and does not include an Fc domain.

9. The antibody claim 1 that has at least a 20-fold preference for binding to activated LFA-1 relative to inactivated LFA-1.

10. A pharmaceutical composition that comprises the antibody according to any of claims 1-9 and a pharmaceutically acceptable salt.

11. The antibody of claim 1 wherein the heavy and light chain variable domain sequences comprise, respectively, SEQ ID NO:60 and SEQ ID NO:61.

12. The antibody of claim 1 comprising SEQ ID NO:33 (light chain) and SEQ ID NO:36 (heavy chain); SEQ ID NO:34 (light chain) and SEQ ID NO:37 (heavy chain); or SEQ ID NO:35 (light chain) and SEQ ID NO:38 (heavy chain).

13. An isolated antibody comprising an immunoglobulin heavy chain (HC) variable domain and an immunoglobulin light chain (LC) variable domain, wherein the HC variable domain and the LC variable domain form an antigen binding site that binds to an activated conformation of LFA-1, wherein the antibody comprises a heavy chain variable domain comprising (a) a CDR1 that comprises HYGMS (SEQ ID NO:10); (b) a CDR2 that comprises VISPSGGRTLYADSVKG (SEQ ID NO:11); and (c) a CDR3 that comprises HYSYAMDV (SEQ ID NO:12); and (ii) the light chain variable domain comprising (d) a CDR1 that comprises TASQSVDSNLA (SEQ ID NO:13); (e) a CDR2 that comprises GASTRAT (SEQ ID NO:14); and (f) a CDR3 that comprises QQYNKWPPYS (SEQ ID NO:15); for binding to activated LFA-1.

14. An isolated antibody comprising an immunoglobulin heavy chain (HC) variable domain and an immunoglobulin light chain (LC) variable domain, wherein the HC variable domain and the LC variable domain form an antigen binding site that binds to an activated conformation of LFA-1, wherein the antibody comprises a heavy chain variable domain comprising (a) a CDR1 that comprises HYSMQ (SEQ ID NO:16); (b) a CDR2 that comprises VIGSSGGNTYYADSVKG (SEQ ID NO:17); and (c) a CDR3 that comprises GTYNTSPFDY (SEQ ID NO:18); and a light chain variable domain comprising (d) a CDR1 that comprises SGDALGQKYAS (SEQ ID NO:19); (e) a CDR2 that comprises QDSKRPS (SEQ ID NO:20); and (f) a CDR3 that comprises QAWDTTAYV (SEQ ID NO:21); for binding to activated LFA-1.

* * * * *

SEQUENCE LISTING

```
<160> NUMBER OF SEQ ID NOS: 61

<210> SEQ ID NO 1
<211> LENGTH: 5
<212> TYPE: PRT
<213> ORGANISM: Homo sapiens

<400> SEQUENCE: 1

Arg Tyr Val Met Trp
1               5

<210> SEQ ID NO 2
<211> LENGTH: 17
<212> TYPE: PRT
<213> ORGANISM: Homo sapiens

<400> SEQUENCE: 2

Tyr Ile Trp Pro Ser Gly Gly Asn Thr Tyr Tyr Ala Asp Ser Val Lys
1               5                   10                  15

Gly

<210> SEQ ID NO 3
<211> LENGTH: 11
<212> TYPE: PRT
<213> ORGANISM: Homo sapiens

<400> SEQUENCE: 3

Ser Tyr Asp Phe Trp Ser Asn Ala Phe Asp Ile
1               5                   10

<210> SEQ ID NO 4
<211> LENGTH: 31
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
```

```
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid

<400> SEQUENCE: 4

Xaa Ala Ala Ser Xaa Ala Ala Asp Xaa Ala Ala Xaa Ala Ala Ser Xaa
1               5                   10                  15

Ala Ala Ala Xaa Ala Ala Xaa Ala Ala Xaa Ala Ala Xaa Ala Ala
            20                  25                  30

<210> SEQ ID NO 5
<211> LENGTH: 27
<212> TYPE: PRT
<213> ORGANISM: Homo sapiens

<400> SEQUENCE: 5

Ser Tyr Phe Asp Leu Tyr Phe Trp Arg Lys Ser Asn Gln Tyr Ala Tyr
1               5                   10                  15

Phe Asp Glu Ala Lys Ile Ser Met Asn Val Leu
            20                  25

<210> SEQ ID NO 6
<211> LENGTH: 25
<212> TYPE: PRT
<213> ORGANISM: Homo sapiens

<400> SEQUENCE: 6

Ser Tyr Phe Asp Leu Tyr Phe Trp Arg Ser Asn Tyr Ala Tyr Phe Asp
1               5                   10                  15

Glu Ala Lys Ile Ser Met Asn Val Leu
            20                  25

<210> SEQ ID NO 7
<211> LENGTH: 11
<212> TYPE: PRT
<213> ORGANISM: Homo sapiens

<400> SEQUENCE: 7

Arg Ala Ser Gln Ser Ile Gly Ser Tyr Leu Asn
1               5                   10

<210> SEQ ID NO 8
<211> LENGTH: 7
<212> TYPE: PRT
<213> ORGANISM: Homo sapiens
```

```
<400> SEQUENCE: 8

Ala Ala Ser Ser Leu Gln Ser
1               5

<210> SEQ ID NO 9
<211> LENGTH: 8
<212> TYPE: PRT
<213> ORGANISM: Homo sapiens

<400> SEQUENCE: 9

Gln Gln Ser Tyr Ser Thr Pro Ser
1               5

<210> SEQ ID NO 10
<211> LENGTH: 5
<212> TYPE: PRT
<213> ORGANISM: Homo sapiens

<400> SEQUENCE: 10

His Tyr Gly Met Ser
1               5

<210> SEQ ID NO 11
<211> LENGTH: 17
<212> TYPE: PRT
<213> ORGANISM: Homo sapiens

<400> SEQUENCE: 11

Val Ile Ser Pro Ser Gly Gly Arg Thr Leu Tyr Ala Asp Ser Val Lys
1               5                   10                  15

Gly

<210> SEQ ID NO 12
<211> LENGTH: 8
<212> TYPE: PRT
<213> ORGANISM: Homo sapiens

<400> SEQUENCE: 12

His Tyr Ser Tyr Ala Met Asp Val
1               5

<210> SEQ ID NO 13
<211> LENGTH: 11
<212> TYPE: PRT
<213> ORGANISM: Homo sapiens

<400> SEQUENCE: 13

Thr Ala Ser Gln Ser Val Asp Ser Asn Leu Ala
1               5                   10

<210> SEQ ID NO 14
<211> LENGTH: 7
<212> TYPE: PRT
<213> ORGANISM: Homo sapiens

<400> SEQUENCE: 14

Gly Ala Ser Thr Arg Ala Thr
1               5

<210> SEQ ID NO 15
<211> LENGTH: 10
<212> TYPE: PRT
<213> ORGANISM: Homo sapiens
```

```
<400> SEQUENCE: 15

Gln Gln Tyr Asn Lys Trp Pro Pro Tyr Ser
1               5                   10

<210> SEQ ID NO 16
<211> LENGTH: 5
<212> TYPE: PRT
<213> ORGANISM: Homo sapiens

<400> SEQUENCE: 16

His Tyr Ser Met Gln
1               5

<210> SEQ ID NO 17
<211> LENGTH: 17
<212> TYPE: PRT
<213> ORGANISM: Homo sapiens

<400> SEQUENCE: 17

Tyr Ile Gly Ser Ser Gly Gly Asn Thr Tyr Tyr Ala Asp Ser Val Lys
1               5                   10                  15

Gly

<210> SEQ ID NO 18
<211> LENGTH: 10
<212> TYPE: PRT
<213> ORGANISM: Homo sapiens

<400> SEQUENCE: 18

Gly Thr Tyr Asn Thr Ser Pro Phe Asp Tyr
1               5                   10

<210> SEQ ID NO 19
<211> LENGTH: 11
<212> TYPE: PRT
<213> ORGANISM: Homo sapiens

<400> SEQUENCE: 19

Ser Gly Asp Ala Leu Gly Gln Lys Tyr Ala Ser
1               5                   10

<210> SEQ ID NO 20
<211> LENGTH: 7
<212> TYPE: PRT
<213> ORGANISM: Homo sapiens

<400> SEQUENCE: 20

Gln Asp Ser Lys Arg Pro Ser
1               5

<210> SEQ ID NO 21
<211> LENGTH: 9
<212> TYPE: PRT
<213> ORGANISM: Homo sapiens

<400> SEQUENCE: 21

Gln Ala Trp Asp Thr Thr Ala Tyr Val
1               5

<210> SEQ ID NO 22
<211> LENGTH: 108
<212> TYPE: PRT
<213> ORGANISM: Homo sapiens

<400> SEQUENCE: 22
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Tyr
            20                  25                  30

Leu Asn Trp Tyr Gln Gln Lys Thr Gly Lys Ala Pro Lys Ala Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Leu
65                  70                  75                  80

Glu Asp Phe Ala Thr Tyr Tyr Cys Gln Gln Ser Tyr Ser Thr Pro Ser
                85                  90                  95

Phe Gly Gln Gly Thr Lys Val Glu Ile Lys Arg Thr
            100                 105
```

<210> SEQ ID NO 23
<211> LENGTH: 120
<212> TYPE: PRT
<213> ORGANISM: Homo sapiens

<400> SEQUENCE: 23

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Met Trp Trp Val Arg Gln Ala Pro Gly Lys Gly Leu Glu Trp Val
        35                  40                  45

Ser Tyr Ile Trp Pro Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Ser Tyr Asp Phe Trp Ser Asn Ala Phe Asp Ile Trp Gly Gln
            100                 105                 110

Gly Thr Met Val Thr Val Ser Ser
        115                 120
```

<210> SEQ ID NO 24
<211> LENGTH: 174
<212> TYPE: PRT
<213> ORGANISM: Homo sapiens

<400> SEQUENCE: 24

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Tyr
            20                  25                  30

Leu Asn Trp Tyr Gln Gln Lys Pro Gly Lys Ala Pro Lys Ala Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ser
                85                  90                  95
```

```
Phe Gly Gln Gly Thr Lys Val Glu Ile Lys Arg Thr Glu Val Gln Leu
                100                 105                 110
Leu Glu Ser Gly Gly Gly Leu Val Gln Pro Gly Gly Ser Leu Arg Leu
            115                 120                 125
Ser Cys Ala Ala Ser Gly Phe Thr Phe Ser Arg Tyr Val Met Trp Trp
130                 135                 140
Val Arg Gln Ala Pro Gly Lys Gly Leu Glu Trp Val Ser Tyr Ile Trp
145                 150                 155                 160
Pro Ser Gly Gly Asn Thr Tyr Tyr Ala Asp Ser Val Lys Gly
                165                 170
```

<210> SEQ ID NO 25
<211> LENGTH: 110
<212> TYPE: PRT
<213> ORGANISM: Homo sapiens

<400> SEQUENCE: 25

```
Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ala Ser
            20                  25                  30
Ser Tyr Asp Phe Trp Ser Asn Ala Phe Asp Ile Trp Gly Gln Gly Thr
        35                  40                  45
Met Val Thr Val Ser Ser Asp Ile Gln Met Thr Gln Ser Pro Ala Thr
    50                  55                  60
Leu Ser Val Ser Pro Gly Glu Arg Val Thr Leu Ser Cys Thr Ala Ser
65                  70                  75                  80
Gln Ser Val Asp Ser Asn Leu Ala Trp Tyr Gln Gln Lys Pro Gly Gln
                85                  90                  95
Ala Pro Arg Leu Leu Val Tyr Gly Ala Ser Thr Arg Ala Thr
            100                 105                 110
```

<210> SEQ ID NO 26
<211> LENGTH: 120
<212> TYPE: PRT
<213> ORGANISM: Homo sapiens

<400> SEQUENCE: 26

```
Gly Val Pro Ala Arg Phe Ser Gly Ser Gly Ser Gly Thr Ala Phe Thr
1               5                   10                  15
Leu Thr Ile Asp Ser Leu Gln Ser Glu Asp Phe Ala Val Tyr Tyr Cys
            20                  25                  30
Gln Gln Tyr Asn Lys Trp Pro Pro Tyr Ser Phe Gly Gln Gly Thr Lys
        35                  40                  45
Leu Glu Ile Lys Arg Thr Glu Val Gln Leu Leu Glu Ser Gly Gly Gly
    50                  55                  60
Leu Val Gln Pro Gly Gly Ser Leu Arg Leu Ser Cys Ala Ala Ser Gly
65                  70                  75                  80
Phe Thr Phe Ser His Tyr Gly Met Ser Trp Val Arg Gln Ala Pro Gly
                85                  90                  95
Lys Gly Leu Glu Trp Val Ser Val Ile Ser Pro Ser Gly Gly Arg Thr
            100                 105                 110
Leu Tyr Ala Asp Ser Val Lys Gly
        115                 120
```

<210> SEQ ID NO 27
<211> LENGTH: 105
<212> TYPE: PRT

<213> ORGANISM: Homo sapiens

<400> SEQUENCE: 27

```
Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ala Lys
                20                  25                  30
His Tyr Ser Tyr Ala Met Asp Val Trp Gly Gln Gly Thr Thr Val Thr
            35                  40                  45
Val Ser Ser Ser Val Leu Thr Gln Pro Pro Ser Val Ser Val Ser Pro
50                  55                  60
Gly Gln Thr Ala Ser Val Thr Cys Ser Gly Asp Ala Leu Gly Gln Lys
65                  70                  75                  80
Tyr Ala Ser Trp Tyr Gln Gln Lys Pro Gly Gln Ser Pro Val Leu Val
                85                  90                  95
Ile Phe Gln Asp Ser Lys Arg Pro Ser
                100                 105
```

<210> SEQ ID NO 28
<211> LENGTH: 117
<212> TYPE: PRT
<213> ORGANISM: Homo sapiens

<400> SEQUENCE: 28

```
Gly Ile Pro Glu Arg Phe Ser Gly Ser Asn Ser Gly Asn Thr Ala Thr
1               5                   10                  15
Leu Thr Ile Ser Gly Thr Gln Ala Val Asp Glu Ala Asp Tyr Tyr Cys
                20                  25                  30
Gln Ala Trp Asp Thr Thr Ala Tyr Val Phe Gly Thr Gly Thr Lys Val
            35                  40                  45
Thr Val Leu Glu Val Gln Leu Leu Glu Ser Gly Gly Gly Leu Val Gln
50                  55                  60
Pro Gly Gly Ser Leu Arg Leu Ser Cys Ala Ala Ser Gly Phe Thr Phe
65                  70                  75                  80
Ser His Tyr Ser Met Gln Trp Val Arg Gln Ala Pro Gly Lys Gly Leu
                85                  90                  95
Glu Trp Val Ser Tyr Ile Gly Ser Ser Gly Gly Asn Thr Tyr Tyr Ala
                100                 105                 110
Asp Ser Val Lys Gly
        115
```

<210> SEQ ID NO 29
<211> LENGTH: 53
<212> TYPE: PRT
<213> ORGANISM: Homo sapiens

<400> SEQUENCE: 29

```
Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ala Arg
                20                  25                  30
Gly Thr Tyr Asn Thr Ser Pro Phe Asp Tyr Trp Gly Gln Gly Thr Leu
            35                  40                  45
Val Thr Val Ser Ser
        50
```

<210> SEQ ID NO 30
<211> LENGTH: 1170

<212> TYPE: PRT
<213> ORGANISM: Homo sapiens

<400> SEQUENCE: 30

```
Met Lys Asp Ser Cys Ile Thr Val Met Ala Met Ala Leu Leu Ser Gly
1               5                   10                  15

Phe Phe Phe Phe Ala Pro Ala Ser Ser Tyr Asn Leu Asp Val Arg Gly
                20                  25                  30

Ala Arg Ser Phe Ser Pro Pro Arg Ala Gly Arg His Phe Gly Tyr Arg
            35                  40                  45

Val Leu Gln Val Gly Asn Gly Val Ile Val Gly Ala Pro Gly Glu Gly
        50                  55                  60

Asn Ser Thr Gly Ser Leu Tyr Gln Cys Gln Ser Gly Thr Gly His Cys
65              70                  75                  80

Leu Pro Val Thr Leu Arg Gly Ser Asn Tyr Thr Ser Lys Tyr Leu Gly
                85                  90                  95

Met Thr Leu Ala Thr Asp Pro Thr Asp Gly Ser Ile Leu Ala Cys Asp
                100                 105                 110

Pro Gly Leu Ser Arg Thr Cys Asp Gln Asn Thr Tyr Leu Ser Gly Leu
            115                 120                 125

Cys Tyr Leu Phe Arg Gln Asn Leu Gln Gly Pro Met Leu Gln Gly Arg
130             135                 140

Pro Gly Phe Gln Glu Cys Ile Lys Gly Asn Val Asp Leu Val Phe Leu
145                 150                 155                 160

Phe Asp Gly Ser Met Ser Leu Gln Pro Asp Glu Phe Gln Lys Ile Leu
                165                 170                 175

Asp Phe Met Lys Asp Val Met Lys Lys Leu Ser Asn Thr Ser Tyr Gln
            180                 185                 190

Phe Ala Ala Val Gln Phe Ser Thr Ser Tyr Lys Thr Glu Phe Asp Phe
        195                 200                 205

Ser Asp Tyr Val Lys Trp Lys Asp Pro Asp Ala Leu Leu Lys His Val
210                 215                 220

Lys His Met Leu Leu Leu Thr Asn Thr Phe Gly Ala Ile Asn Tyr Val
225                 230                 235                 240

Ala Thr Glu Val Phe Arg Glu Glu Leu Gly Ala Arg Pro Asp Ala Thr
                245                 250                 255

Lys Val Leu Ile Ile Thr Asp Gly Glu Ala Thr Asp Ser Gly Asn
            260                 265                 270

Ile Asp Ala Ala Lys Asp Ile Ile Arg Tyr Ile Ile Gly Ile Gly Lys
        275                 280                 285

His Phe Gln Thr Lys Glu Ser Gln Glu Thr Leu His Lys Phe Ala Ser
290                 295                 300

Lys Pro Ala Ser Glu Phe Val Lys Ile Leu Asp Thr Phe Glu Lys Leu
305                 310                 315                 320

Lys Asp Leu Phe Thr Glu Leu Gln Lys Lys Ile Tyr Val Ile Glu Gly
                325                 330                 335

Thr Ser Lys Gln Asp Leu Thr Ser Phe Asn Met Glu Leu Ser Ser Ser
            340                 345                 350

Gly Ile Ser Ala Asp Leu Ser Arg Gly His Ala Val Val Gly Ala Val
        355                 360                 365

Gly Ala Lys Asp Trp Ala Gly Gly Phe Leu Asp Leu Lys Ala Asp Leu
    370                 375                 380

Gln Asp Asp Thr Phe Ile Gly Asn Glu Pro Leu Thr Pro Glu Val Arg
385                 390                 395                 400
```

-continued

Ala Gly Tyr Leu Gly Tyr Thr Val Thr Trp Leu Pro Ser Arg Gln Lys
                405                 410                 415

Thr Ser Leu Leu Ala Ser Gly Ala Pro Arg Tyr Gln His Met Gly Arg
            420                 425                 430

Val Leu Leu Phe Gln Glu Pro Gln Gly Gly His Trp Ser Gln Val
            435                 440                 445

Gln Thr Ile His Gly Thr Gln Ile Gly Ser Tyr Phe Gly Gly Glu Leu
        450                 455                 460

Cys Gly Val Asp Val Asp Gln Asp Gly Glu Thr Glu Leu Leu Leu Ile
465                 470                 475                 480

Gly Ala Pro Leu Phe Tyr Gly Glu Gln Arg Gly Gly Arg Val Phe Ile
                485                 490                 495

Tyr Gln Arg Arg Gln Leu Gly Phe Glu Glu Val Ser Glu Leu Gln Gly
            500                 505                 510

Asp Pro Gly Tyr Pro Leu Gly Arg Phe Gly Glu Ala Ile Thr Ala Leu
        515                 520                 525

Thr Asp Ile Asn Gly Asp Gly Leu Val Asp Val Ala Val Gly Ala Pro
    530                 535                 540

Leu Glu Glu Gln Gly Ala Val Tyr Ile Phe Asn Gly Arg His Gly Gly
545                 550                 555                 560

Leu Ser Pro Gln Pro Ser Gln Arg Ile Glu Gly Thr Gln Val Leu Ser
                565                 570                 575

Gly Ile Gln Trp Phe Gly Arg Ser Ile His Gly Val Lys Asp Leu Glu
            580                 585                 590

Gly Asp Gly Leu Ala Asp Val Ala Val Gly Ala Glu Ser Gln Met Ile
        595                 600                 605

Val Leu Ser Ser Arg Pro Val Val Asp Met Val Thr Leu Met Ser Phe
    610                 615                 620

Ser Pro Ala Glu Ile Pro Val His Glu Val Glu Cys Ser Tyr Ser Thr
625                 630                 635                 640

Ser Asn Lys Met Lys Glu Gly Val Asn Ile Thr Ile Cys Phe Gln Ile
                645                 650                 655

Lys Ser Leu Tyr Pro Gln Phe Gln Gly Arg Leu Val Ala Asn Leu Thr
            660                 665                 670

Tyr Thr Leu Gln Leu Asp Gly His Arg Thr Arg Arg Arg Gly Leu Phe
        675                 680                 685

Pro Gly Gly Arg His Glu Leu Arg Arg Asn Ile Ala Val Thr Thr Ser
    690                 695                 700

Met Ser Cys Thr Asp Phe Ser Phe His Phe Pro Val Cys Val Gln Asp
705                 710                 715                 720

Leu Ile Ser Pro Ile Asn Val Ser Leu Asn Phe Ser Leu Trp Glu Glu
                725                 730                 735

Glu Gly Thr Pro Arg Asp Gln Arg Ala Gln Gly Lys Asp Ile Pro Pro
            740                 745                 750

Leu Leu Arg Pro Ser Leu His Ser Glu Thr Trp Glu Ile Pro Phe Glu
        755                 760                 765

Lys Asn Cys Gly Glu Asp Lys Lys Cys Glu Ala Asn Leu Arg Val Ser
    770                 775                 780

Phe Ser Pro Ala Arg Ser Arg Ala Leu Arg Leu Thr Ala Phe Ala Ser
785                 790                 795                 800

Leu Ser Val Glu Leu Ser Leu Ser Asn Leu Glu Glu Asp Ala Tyr Trp
                805                 810                 815

Val Gln Leu Asp Leu His Phe Pro Pro Gly Leu Ser Phe Arg Lys Val
            820                 825                 830

```
Glu Met Leu Lys Pro His Ser Gln Ile Pro Val Ser Cys Glu Glu Leu
        835                 840                 845

Pro Glu Glu Ser Arg Leu Leu Ser Arg Ala Leu Ser Cys Asn Val Ser
850                 855                 860

Ser Pro Ile Phe Lys Ala Gly His Ser Val Ala Leu Gln Met Met Phe
865                 870                 875                 880

Asn Thr Leu Val Asn Ser Ser Trp Gly Asp Ser Val Glu Leu His Ala
                885                 890                 895

Asn Val Thr Cys Asn Asn Glu Asp Ser Asp Leu Leu Glu Asp Asn Ser
                900                 905                 910

Ala Thr Thr Ile Ile Pro Ile Leu Tyr Pro Ile Asn Ile Leu Ile Gln
                915                 920                 925

Asp Gln Glu Asp Ser Thr Leu Tyr Val Ser Phe Thr Pro Lys Gly Pro
                930                 935                 940

Lys Ile His Gln Val Lys His Met Tyr Gln Val Arg Ile Gln Pro Ser
945                 950                 955                 960

Ile His Asp His Asn Ile Pro Thr Leu Glu Ala Val Val Gly Val Pro
                965                 970                 975

Gln Pro Pro Ser Glu Gly Pro Ile Thr His Gln Trp Ser Val Gln Met
                980                 985                 990

Glu Pro Pro Val Pro Cys His Tyr Glu Asp Leu Glu Arg Leu Pro Asp
                995                 1000                1005

Ala Ala Glu Pro Cys Leu Pro Gly Ala Leu Phe Arg Cys Pro Val
        1010                1015                1020

Val Phe Arg Gln Glu Ile Leu Val Gln Val Ile Gly Thr Leu Glu
        1025                1030                1035

Leu Val Gly Glu Ile Glu Ala Ser Ser Met Phe Ser Leu Cys Ser
        1040                1045                1050

Ser Leu Ser Ile Ser Phe Asn Ser Ser Lys His Phe His Leu Tyr
        1055                1060                1065

Gly Ser Asn Ala Ser Leu Ala Gln Val Val Met Lys Val Asp Val
        1070                1075                1080

Val Tyr Glu Lys Gln Met Leu Tyr Leu Tyr Val Leu Ser Gly Ile
        1085                1090                1095

Gly Gly Leu Leu Leu Leu Leu Ile Phe Ile Val Leu Tyr Lys
        1100                1105                1110

Val Gly Phe Phe Lys Arg Asn Leu Lys Glu Lys Met Glu Ala Gly
        1115                1120                1125

Arg Gly Val Pro Asn Gly Ile Pro Ala Glu Asp Ser Glu Gln Leu
        1130                1135                1140

Ala Ser Gly Gln Glu Ala Gly Asp Pro Gly Cys Leu Lys Pro Leu
        1145                1150                1155

His Glu Lys Asp Ser Glu Ser Gly Gly Gly Lys Asp
        1160                1165                1170

<210> SEQ ID NO 31
<211> LENGTH: 769
<212> TYPE: PRT
<213> ORGANISM: Homo sapiens

<400> SEQUENCE: 31

Met Leu Gly Leu Arg Pro Pro Leu Leu Ala Leu Val Gly Leu Leu Ser
1               5                   10                  15

Leu Gly Cys Val Leu Ser Gln Glu Cys Thr Lys Phe Lys Val Ser Ser
                20                  25                  30
```

```
Cys Arg Glu Cys Ile Glu Ser Gly Pro Gly Cys Thr Trp Cys Gln Lys
            35                  40                  45

Leu Asn Phe Thr Gly Pro Gly Asp Pro Asp Ser Ile Arg Cys Asp Thr
 50                  55                  60

Arg Pro Gln Leu Leu Met Arg Gly Cys Ala Ala Asp Asp Ile Met Asp
 65                  70                  75                  80

Pro Thr Ser Leu Ala Glu Thr Gln Glu Asp His Asn Gly Gly Gln Lys
                 85                  90                  95

Gln Leu Ser Pro Gln Lys Val Thr Leu Tyr Leu Arg Pro Gly Gln Ala
                100                 105                 110

Ala Ala Phe Asn Val Thr Phe Arg Arg Ala Lys Gly Tyr Pro Ile Asp
                115                 120                 125

Leu Tyr Tyr Leu Met Asp Leu Ser Tyr Ser Met Leu Asp Asp Leu Arg
                130                 135                 140

Asn Val Lys Lys Leu Gly Gly Asp Leu Leu Arg Ala Leu Asn Glu Leu
145                 150                 155                 160

Thr Glu Ser Gly Arg Ile Gly Phe Gly Ser Phe Val Asp Lys Thr Val
                165                 170                 175

Leu Pro Phe Val Asn Thr Ile Ile Pro Asp Lys Leu Arg Asn Pro Cys
                180                 185                 190

Pro Asn Lys Glu Lys Glu Cys Gln Pro Pro Phe Ala Phe Arg His Val
                195                 200                 205

Leu Lys Leu Thr Asn Asn Ser Asn Gln Phe Gln Thr Glu Val Gly Lys
                210                 215                 220

Gln Leu Ile Ser Gly Asn Leu Asp Ala Pro Glu Gly Gly Leu Asp Ala
225                 230                 235                 240

Met Met Gln Val Ala Ala Cys Pro Glu Glu Ile Gly Trp Arg Asn Val
                245                 250                 255

Thr Arg Leu Leu Val Phe Ala Thr Asp Asp Gly Phe His Phe Ala Gly
                260                 265                 270

Asp Gly Lys Leu Gly Ala Ile Leu Thr Pro Asn Asp Gly Arg Cys His
                275                 280                 285

Leu Glu Asp Asn Leu Tyr Lys Arg Ser Asn Glu Phe Asp Val Pro Ser
                290                 295                 300

Val Gly Gln Leu Ala His Lys Leu Ala Glu Asn Asn Ile Gln Pro Ile
305                 310                 315                 320

Phe Ala Val Thr Ser Arg Met Val Lys Thr Tyr Glu Lys Leu Thr Glu
                325                 330                 335

Ile Ile Pro Lys Ser Ala Val Gly Glu Leu Ser Glu Asp Ser Ser Asn
                340                 345                 350

Val Val His Leu Ile Lys Asn Ala Tyr Asn Lys Leu Ser Ser Arg Val
                355                 360                 365

Phe Leu Asp His Asn Ala Leu Pro Asp Thr Leu Lys Val Thr Tyr Asp
                370                 375                 380

Ser Phe Cys Ser Asn Gly Val Thr His Arg Asn Gln Pro Arg Gly Asp
385                 390                 395                 400

Cys Asp Gly Val Gln Ile Asn Val Pro Ile Thr Phe Gln Val Lys Val
                405                 410                 415

Thr Ala Thr Glu Cys Ile Gln Glu Gln Ser Phe Val Ile Arg Ala Leu
                420                 425                 430

Gly Phe Thr Asp Ile Val Thr Val Gln Val Leu Pro Gln Cys Glu Cys
                435                 440                 445

Arg Cys Arg Asp Gln Ser Arg Asp Arg Ser Leu Cys His Gly Lys Gly
```

```
                    450                 455                 460
Phe Leu Glu Cys Gly Ile Cys Arg Cys Asp Thr Gly Tyr Ile Gly Lys
465                 470                 475                 480

Asn Cys Glu Cys Gln Thr Gln Gly Arg Ser Ser Gln Glu Leu Glu Gly
                485                 490                 495

Ser Cys Arg Lys Asp Asn Ser Ile Ile Cys Ser Gly Leu Gly Asp
                500                 505                 510

Cys Val Cys Gly Gln Cys Leu Cys His Thr Ser Asp Val Pro Gly Lys
                515                 520                 525

Leu Ile Tyr Gly Gln Tyr Cys Glu Cys Asp Thr Ile Asn Cys Glu Arg
530                 535                 540

Tyr Asn Gly Gln Val Cys Gly Pro Gly Arg Gly Leu Cys Phe Cys
545                 550                 555                 560

Gly Lys Cys Arg Cys His Pro Gly Phe Glu Gly Ser Ala Cys Gln Cys
                565                 570                 575

Glu Arg Thr Thr Glu Gly Cys Leu Asn Pro Arg Arg Val Glu Cys Ser
                580                 585                 590

Gly Arg Gly Arg Cys Arg Cys Asn Val Cys Glu Cys His Ser Gly Tyr
                595                 600                 605

Gln Leu Pro Leu Cys Gln Glu Cys Pro Gly Cys Pro Ser Pro Cys Gly
                610                 615                 620

Lys Tyr Ile Ser Cys Ala Glu Cys Leu Lys Phe Glu Lys Gly Pro Phe
625                 630                 635                 640

Gly Lys Asn Cys Ser Ala Ala Cys Pro Gly Leu Gln Leu Ser Asn Asn
                645                 650                 655

Pro Val Lys Gly Arg Thr Cys Lys Glu Arg Asp Ser Glu Gly Cys Trp
                660                 665                 670

Val Ala Tyr Thr Leu Glu Gln Gln Asp Gly Met Asp Arg Tyr Leu Ile
                675                 680                 685

Tyr Val Asp Glu Ser Arg Glu Cys Val Ala Gly Pro Asn Ile Ala Ala
                690                 695                 700

Asn Gly Gly Thr Val Ala Gly Ile Val Leu Ile Gly Ile Leu Leu Leu
705                 710                 715                 720

Val Ile Trp Lys Ala Leu Ile His Leu Ser Asp Leu Arg Glu Tyr Arg
                725                 730                 735

Arg Phe Glu Lys Glu Lys Leu Lys Ser Gln Trp Asn Asn Asp Asn Pro
                740                 745                 750

Leu Phe Lys Ser Ala Thr Thr Thr Val Met Asn Pro Lys Phe Ala Glu
                755                 760                 765

Ser

<210> SEQ ID NO 32
<211> LENGTH: 323
<212> TYPE: PRT
<213> ORGANISM: Homo sapiens

<400> SEQUENCE: 32

Gly Asn Val Asp Leu Val Phe Leu Phe Asp Gly Ser Met Ser Leu Gln
1                 5                  10                  15

Pro Asp Glu Phe Gln Lys Ile Leu Asp Phe Met Lys Asp Val Met Lys
                20                  25                  30

Lys Leu Ser Asn Thr Ser Tyr Gln Phe Ala Ala Val Gln Phe Ser Thr
                35                  40                  45

Ser Glu Glu Glu Glu Glu Glu Glu Asx Thr Thr Ser His His His
                50                  55                  60
```

```
His His His His His His His His His His His Thr Thr
65                  70                  75                  80

Thr Ser Ser Glu Glu Glu Glu Glu Glu Glu Ser Ser Ser Tyr Lys
                85                  90                  95

Thr Glu Phe Asp Phe Ser Asp Tyr Val Lys Arg Lys Asp Pro Asp Ala
            100                 105                 110

Leu Leu Lys His Val Lys His Met Leu Leu Thr Asn Thr Phe Gly
        115                 120                 125

Ala Ile Asn Tyr Val Ala Thr Glu Val Phe Arg Glu Glu Leu Gly Ala
    130                 135                 140

Glu Glu Glu Ser Asx His His His His His Thr Thr His His
145                 150                 155                 160

His His Thr Ser Ser Asx His His His His His His His His
            165                 170                 175

His Thr Thr Thr Gly Gly Gly Thr Arg Pro Asp Ala Thr Lys Val Leu
        180                 185                 190

Ile Ile Ile Thr Asp Gly Glu Ala Thr Asp Ser Gly Asn Ile Asp Ala
        195                 200                 205

Ala Lys Asp Ile Ile Arg Tyr Ile Ile Gly Ile Gly Lys His Phe Gln
    210                 215                 220

Thr Lys Glu Ser Gln Glu Thr Leu His Lys Thr Thr Ser Glu Glu
225                 230                 235                 240

Glu Glu Glu Glu Glu Ser Ser Gly Gly Gly Thr Thr Ser Glu Glu
                245                 250                 255

Glu Glu Glu Ser Ser Ser Thr Thr Gly Gly Gly Thr Thr Phe
            260                 265                 270

Ala Ser Lys Pro Ala Ser Glu Phe Val Lys Ile Leu Asp Thr Phe Glu
    275                 280                 285

Lys Leu Lys Asp Leu Phe Thr Glu Leu Gln Lys Lys Ile Thr Ser Ser
        290                 295                 300

Ser His His His His Glu Glu Glu Thr Thr Thr Thr Thr Thr Thr
305                 310                 315                 320

Thr Thr Thr

<210> SEQ ID NO 33
<211> LENGTH: 115
<212> TYPE: PRT
<213> ORGANISM: Homo sapiens
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid

<400> SEQUENCE: 33

Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Gly Ser
            20                  25                  30

Tyr Leu Asn Trp Tyr Gln Gln Lys Thr Gly Lys Ala Pro Lys Ala Leu
        35                  40                  45

Ile Tyr Ala Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
```

```
                65                  70                  75                  80
Leu Glu Asp Phe Ala Thr Tyr Tyr Cys Gln Gln Ser Tyr Ser Thr Pro
                    85                  90                  95

Xaa Ala Ala Xaa Ala Ala Ser Phe Gly Gln Gly Thr Lys Val Glu Ile
            100                 105                 110

Lys Arg Thr
        115

<210> SEQ ID NO 34
<211> LENGTH: 110
<212> TYPE: PRT
<213> ORGANISM: Homo sapiens

<400> SEQUENCE: 34

Gln Asp Ile Gln Met Thr Gln Ser Pro Ala Thr Leu Ser Val Ser Pro
1               5                   10                  15

Gly Glu Arg Val Thr Leu Ser Cys Thr Ala Ser Gln Ser Val Asp Ser
            20                  25                  30

Asn Leu Ala Trp Tyr Gln Gln Lys Pro Gly Gln Ala Pro Arg Leu Leu
        35                  40                  45

Val Tyr Gly Ala Ser Thr Arg Ala Thr Gly Val Pro Ala Arg Phe Ser
50                  55                  60

Gly Ser Gly Ser Gly Thr Ala Phe Thr Leu Thr Ile Asp Ser Leu Gln
65                  70                  75                  80

Ser Glu Asp Phe Ala Val Tyr Tyr Cys Gln Tyr Asn Lys Trp Pro Pro
                85                  90                  95

Tyr Ser Phe Gly Gln Gly Thr Lys Leu Glu Ile Lys Arg Thr
            100                 105                 110

<210> SEQ ID NO 35
<211> LENGTH: 114
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid

<400> SEQUENCE: 35

Gln Ser Val Xaa Ala Ala Leu Thr Gln Xaa Ala Ala Pro Pro Ser Val
1               5                   10                  15

Ser Val Ser Pro Gly Gln Thr Ala Ser Val Thr Cys Ser Gly Asp Ala
            20                  25                  30

Leu Gly Gln Lys Tyr Ala Ser Trp Tyr Gln Gln Lys Pro Gly Gln Ser
        35                  40                  45

Pro Val Leu Val Ile Phe Gln Asp Ser Lys Arg Pro Ser Gly Ile Pro
50                  55                  60

Glu Arg Phe Ser Gly Ser Asn Ser Gly Asn Thr Ala Thr Leu Thr Ile
65                  70                  75                  80

Ser Gly Thr Gln Ala Val Asp Glu Ala Asp Tyr Tyr Cys Gln Ala Trp
                85                  90                  95

Asp Thr Thr Xaa Ala Ala Ala Tyr Val Gly Thr Gly Thr Lys Val Thr
            100                 105                 110
```

Val Leu

<210> SEQ ID NO 36
<211> LENGTH: 120
<212> TYPE: PRT
<213> ORGANISM: Homo sapiens

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Met Trp Val Arg Gln Ala Pro Gly Lys Gly Leu Glu Trp Val
        35                  40                  45

Ser Tyr Ile Trp Pro Ser Gly Gly Asn Thr Thr Ile Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Ser Tyr Asp Phe Trp Ser Asn Ala Phe Asp Ile Trp Gly Gln
            100                 105                 110

Gly Thr Met Val Thr Val Ser Ser
        115                 120

<210> SEQ ID NO 37
<211> LENGTH: 120
<212> TYPE: PRT
<213> ORGANISM: Homo sapiens
<220> FEATURE:
<221> NAME/KEY: misc_feature
<222> LOCATION: (103)..(103)
<223> OTHER INFORMATION: Xaa can be any naturally occurring amino acid

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Gly Met Ser Trp Val Arg Gln Ala Pro Gly Lys Gly Leu Glu Trp Val
        35                  40                  45

Ser Val Ile Ser Pro Ser Gly Gly Arg Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Tyr Ser Tyr Xaa Ala Ala Ala Met Asp Val Trp Gly Gln
            100                 105                 110

Gly Thr Thr Val Thr Val Ser Ser
        115                 120

<210> SEQ ID NO 38
<211> LENGTH: 122
<212> TYPE: PRT
<213> ORGANISM: Homo sapiens
<220> FEATURE:
<221> NAME/KEY: misc_feature
<222> LOCATION: (100)..(100)
<223> OTHER INFORMATION: Xaa can be any naturally occurring amino acid

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Ser Met Gln Trp Val Arg Gln Ala Pro Gly Lys Gly Leu Glu Trp Val
        35                  40                  45

Ser Tyr Ile Gly Ser Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Xaa Ala Ala Thr Tyr Asn Thr Ser Pro Phe Asp Tyr Trp
            100                 105                 110

Gly Gln Gly Thr Leu Val Thr Val Ser Ser
        115                 120

<210> SEQ ID NO 39
<211> LENGTH: 320
<212> TYPE: DNA
<213> ORGANISM: Homo sapiens

<400> SEQUENCE: 39
caagacatcc agatgaccca gtctccatcc tccctgtctg catctgtagg agacagagtc     60
accatcactt gccgggcaag tcagagcatt ggcagctact taaactggta tcagcagaaa    120
acagggaaag cccctaaggc cctgatctat ctgcatccag tttgcaaagt ggggtcccat    180
caaggttcag tggcagtggg tctgggacag atttcactct caccatcagt agtctgcaac    240
ttgaagattt tgcaacttac tactgtcaac agagttacag taccccctcg ttcggccaag    300
ggaccaaggt ggaaatcaaa                                                320

<210> SEQ ID NO 40
<211> LENGTH: 327
<212> TYPE: DNA
<213> ORGANISM: Homo sapiens

<400> SEQUENCE: 40
caagacatcc agatgaccca gtctccagcc accctgtctg tgtctccagg ggaaagagtc     60
accctctcct gcacggccag tcagagtgtt gacagcaact tagcctggta tcagcaaaaa    120
cctggccagg ctcccagact cctcgtctat ggtgcatcca ctagggccac tggtgtccca    180
gccaggttca gtggcagtgg gtctgggaca gcgttcactc tcaccatcga cagcctgcag    240
tctgaagatt ttgcagttta ttactgtcag cagtataata gtggcctcc gtactccttt     300 ggccagggga ccaagctgga gatcaag                                        327

<210> SEQ ID NO 41
<211> LENGTH: 319
<212> TYPE: PRT
<213> ORGANISM: Homo sapiens

<400> SEQUENCE: 41

Cys Ala Gly Ala Gly Cys Gly Thr Cys Thr Thr Gly Ala Cys Thr Cys
1               5                   10                  15

Ala Gly Cys Cys Ala Cys Cys Cys Thr Cys Ala Gly Thr Gly Thr Cys
            20                  25                  30

```
Cys Gly Thr Cys Thr Cys Cys Cys Cys Ala Gly Gly Ala Cys Ala Gly
        35                  40                  45

Ala Cys Ala Gly Cys Cys Ala Gly Cys Gly Thr Cys Ala Cys Thr Thr
    50                  55                  60

Gly Cys Thr Cys Thr Gly Gly Ala Gly Ala Thr Gly Cys Ala Thr Thr
65                  70                  75                  80

Gly Gly Gly Ala Cys Ala Ala Ala Ala Ala Thr Ala Thr Gly Cys Thr
                85                  90                  95

Thr Cys Cys Thr Gly Gly Thr Ala Thr Cys Ala Ala Cys Ala Gly Ala
            100                 105                 110

Ala Gly Cys Cys Ala Gly Gly Cys Cys Ala Gly Thr Cys Cys Cys Cys
        115                 120                 125

Thr Gly Thr Ala Cys Thr Gly Gly Thr Cys Ala Thr Cys Thr Thr Thr
    130                 135                 140

Cys Ala Ala Gly Ala Thr Thr Cys Cys Ala Ala Gly Cys Gly Gly Cys
145                 150                 155                 160

Cys Cys Thr Cys Ala Gly Gly Gly Ala Thr Cys Cys Cys Thr Gly Ala
                165                 170                 175

Gly Cys Gly Gly Thr Thr Cys Thr Cys Thr Gly Gly Cys Thr Cys Cys
            180                 185                 190

Ala Ala Thr Thr Cys Thr Gly Gly Gly Ala Ala Cys Ala Cys Ala Gly
        195                 200                 205

Cys Cys Ala Cys Thr Cys Thr Gly Ala Cys Cys Ala Thr Cys Ala Gly
    210                 215                 220

Cys Gly Gly Gly Ala Cys Cys Cys Ala Gly Gly Cys Thr Gly Thr Gly
225                 230                 235                 240

Gly Ala Thr Gly Ala Gly Gly Cys Cys Gly Ala Cys Thr Ala Thr Thr
                245                 250                 255

Ala Thr Thr Gly Thr Cys Ala Gly Gly Cys Gly Thr Gly Gly Gly Ala
            260                 265                 270

Cys Ala Cys Thr Ala Cys Ala Gly Cys Thr Thr Ala Thr Gly Thr Cys
        275                 280                 285

Thr Thr Cys Gly Gly Ala Ala Gly Cys Thr Gly Gly Gly Ala Cys Cys
    290                 295                 300

Ala Ala Gly Gly Thr Cys Ala Cys Cys Gly Thr Cys Cys Thr Ala
305                 310                 315

<210> SEQ ID NO 42
<211> LENGTH: 360
<212> TYPE: PRT
<213> ORGANISM: Homo sapiens

<400> SEQUENCE: 42

Gly Ala Ala Gly Thr Thr Cys Ala Ala Thr Thr Gly Thr Thr Ala Gly
1               5                   10                  15

Ala Gly Thr Cys Thr Gly Gly Thr Gly Gly Cys Gly Gly Thr Cys Thr
            20                  25                  30

Thr Gly Thr Thr Cys Ala Gly Cys Cys Thr Gly Gly Thr Gly Gly Thr
        35                  40                  45

Thr Cys Thr Thr Thr Ala Cys Gly Thr Cys Thr Thr Thr Cys Thr Thr
    50                  55                  60

Gly Cys Gly Cys Thr Gly Cys Thr Thr Cys Cys Gly Gly Ala Thr Thr
65                  70                  75                  80

Cys Ala Cys Thr Thr Thr Cys Thr Cys Thr Cys Gly Thr Thr Ala Cys
                85                  90                  95
```

Gly Thr Thr Ala Thr Gly Thr Gly Thr Gly Gly Thr Thr Cys
            100                 105                 110
Gly Cys Cys Ala Ala Gly Cys Thr Cys Thr Gly Gly Thr Ala Ala
        115                 120                 125
Ala Gly Gly Thr Thr Gly Gly Ala Gly Thr Gly Gly Thr Thr
    130                 135                 140
Thr Cys Thr Thr Ala Thr Ala Thr Cys Thr Gly Gly Cys Cys Thr
145                 150                 155                 160
Cys Thr Gly Gly Thr Gly Gly Cys Ala Ala Thr Ala Cys Thr Ala
            165                 170                 175
Thr Thr Ala Thr Gly Cys Thr Gly Ala Cys Thr Cys Cys Gly Thr Thr
            180                 185                 190
Ala Ala Ala Gly Gly Thr Cys Gly Cys Thr Thr Cys Ala Cys Thr Ala
        195                 200                 205
Thr Cys Thr Cys Thr Ala Gly Ala Gly Ala Cys Ala Ala Cys Thr Cys
    210                 215                 220
Thr Ala Ala Gly Ala Ala Thr Ala Cys Thr Cys Thr Cys Thr Ala Cys
225                 230                 235                 240
Thr Thr Gly Cys Ala Gly Ala Thr Gly Ala Ala Cys Ala Gly Cys Thr
            245                 250                 255
Thr Ala Ala Gly Gly Cys Thr Gly Ala Gly Gly Ala Cys Ala Cys
            260                 265                 270
Thr Gly Cys Ala Gly Thr Cys Thr Ala Cys Thr Ala Thr Thr Gly Thr
            275                 280                 285
Gly Cys Gly Ala Gly Thr Ala Cys Thr Ala Cys Gly Ala Thr Thr
        290                 295                 300
Thr Thr Thr Gly Gly Ala Gly Thr Ala Ala Thr Gly Cys Thr Thr Thr
305                 310                 315                 320
Thr Gly Ala Thr Ala Thr Cys Thr Gly Gly Gly Gly Cys Cys Ala Ala
            325                 330                 335
Gly Gly Gly Ala Cys Ala Ala Thr Gly Gly Thr Cys Ala Cys Cys Gly
            340                 345                 350
Thr Cys Thr Cys Ala Ala Gly Cys
            355                 360

<210> SEQ ID NO 43
<211> LENGTH: 351
<212> TYPE: DNA
<213> ORGANISM: Homo sapiens

<400> SEQUENCE: 43
gaagttcaat tgttagagtc tggtggcggt cttgttcagc ctggtggttc tttacgtctt    60
tcttgcgctg cttccggatt cactttctct cattacggta tgtcttgggt tcgccaagct   120
cctggtaaag gtttggagtg gtttctgtt atctctcctt ctggtggccg tactctttat   180
gctgactccg ttaaaggtcg cttcactatc tctagagaca actctaagaa tactctctac   240
ttgcagatga acagcttaag ggctgaggac actgcagtct actattgtgc gaaacattac   300
tcctacgcta tggacgtctg gggccaaggg accacggtca ccgtctcaag c            351

<210> SEQ ID NO 44
<211> LENGTH: 357
<212> TYPE: DNA
<213> ORGANISM: Homo sapiens

<400> SEQUENCE: 44

```
gaagttcaat tgttagagtc tggtggcggt cttgttcagc ctggtggttc tttacgtctt        60
tcttgcgctg cttccggatt cactttctct cattactcta tgcagtgggt tcgccaagct       120
cctggtaaag gtttggagtg ggtttcttat atcggttctt ctggtggcaa tacttattat       180
gctgactccg ttaaaggtcg cttcactatc tctagagaca actctaagaa tactctctac       240
ttgcagatga acagcttaag ggctgaggac actgcagtct actattgtgc gagagggacc       300
tataacacct cccctttga ctactggggc cagggaaccc tggtcaccgt ctcaagc          357
```

<210> SEQ ID NO 45
<211> LENGTH: 17
<212> TYPE: PRT
<213> ORGANISM: Homo sapiens

<400> SEQUENCE: 45

Ala Glu Tyr Phe Gln His Trp Gly Gln Gly Thr Leu Val Thr Val Ser
1               5                   10                  15

Ser

<210> SEQ ID NO 46
<211> LENGTH: 17
<212> TYPE: PRT
<213> ORGANISM: Homo sapiens

<400> SEQUENCE: 46

Tyr Trp Tyr Phe Asp Leu Trp Gly Arg Gly Thr Leu Val Thr Val Ser
1               5                   10                  15

Ser

<210> SEQ ID NO 47
<211> LENGTH: 15
<212> TYPE: PRT
<213> ORGANISM: Homo sapiens

<400> SEQUENCE: 47

Ala Phe Asp Ile Trp Gly Gln Gly Thr Met Val Thr Val Ser Ser
1               5                   10                  15

<210> SEQ ID NO 48
<211> LENGTH: 29
<212> TYPE: PRT
<213> ORGANISM: Homo sapiens

<400> SEQUENCE: 48

Tyr Phe Asp Tyr Trp Gly Gln Gly Thr Leu Val Thr Val Ser Ser Phe
1               5                   10                  15

Asp Tyr Trp Gly Gln Gly Thr Leu Val Thr Val Ser Ser
            20                  25

<210> SEQ ID NO 49
<211> LENGTH: 16
<212> TYPE: PRT
<213> ORGANISM: Homo sapiens

<400> SEQUENCE: 49

Asn Trp Phe Asp Pro Trp Gly Gln Gly Thr Leu Val Thr Val Ser Ser
1               5                   10                  15

<210> SEQ ID NO 50
<211> LENGTH: 20
<212> TYPE: PRT
<213> ORGANISM: Homo sapiens -continued

<400> SEQUENCE: 50

Tyr Tyr Tyr Tyr Gly Met Asp Val Trp Gly Gln Gly Thr Thr Val
1               5                   10                  15

Thr Val Ser Ser
            20

<210> SEQ ID NO 51
<211> LENGTH: 120
<212> TYPE: PRT
<213> ORGANISM: Homo sapiens

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Met Trp Trp Val Arg Gln Ala Pro Gly Lys Gly Leu Glu Trp Val
        35                  40                  45

Ser Tyr Ile Trp Pro Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Ser Tyr Asp Tyr Trp Ser Asn Ala Phe Asp Ser Trp Gly Gln
            100                 105                 110

Gly Thr Met Val Thr Val Ser Ser
        115                 120

<210> SEQ ID NO 52
<211> LENGTH: 120
<212> TYPE: PRT
<213> ORGANISM: Homo sapiens

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Met Trp Trp Val Arg Gln Ala Pro Gly Lys Gly Leu Glu Trp Val
        35                  40                  45

Ser Tyr Ile Trp Pro Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Ser Phe Asp Phe Trp Ser Asn Ala Phe Asp Met Trp Gly Gln
            100                 105                 110

Gly Thr Met Val Thr Val Ser Ser
        115                 120

<210> SEQ ID NO 53
<211> LENGTH: 120
<212> TYPE: PRT
<213> ORGANISM: Homo sapiens

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Met Trp Trp Val Arg Gln Ala Pro Gly Lys Gly Leu Glu Trp Val
        35                  40                  45

Ser Tyr Ile Trp Pro Ser Gly Gly Asn Thr Tyr Tyr Ala Asp Ser Val
    50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Ser Tyr Asp Leu Trp Ser Asn Ala Phe Asp Lys Trp Gly Gln
                100                 105                 110

Gly Thr Met Val Thr Val Ser Ser
            115                 120

<210> SEQ ID NO 54
<211> LENGTH: 120
<212> TYPE: PRT
<213> ORGANISM: Homo sapiens

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Met Trp Trp Val Arg Gln Ala Pro Gly Lys Gly Leu Glu Trp Val
        35                  40                  45

Ser Tyr Ile Trp Pro Ser Gly Gly Asn Thr Tyr Tyr Ala Asp Ser Val
    50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Ser Tyr Asp Phe Arg Ser Asn Ala Phe Ala Val Trp Gly Gln
                100                 105                 110

Gly Thr Met Val Thr Val Ser Ser
            115                 120

<210> SEQ ID NO 55
<211> LENGTH: 120
<212> TYPE: PRT
<213> ORGANISM: Homo sapiens

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Met Trp Trp Val Arg Gln Ala Pro Gly Lys Gly Leu Glu Trp Val
        35                  40                  45

Ser Tyr Ile Trp Pro Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                85                  90                  95
Ala Ser Ser Tyr Asp Phe Trp Ser Asn Ala Tyr Ala Asn Trp Gly Gln
            100                 105                 110

Gly Thr Met Val Thr Val Ser Ser
        115                 120

<210> SEQ ID NO 56
<211> LENGTH: 120
<212> TYPE: PRT
<213> ORGANISM: Homo sapiens

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Met Trp Trp Val Arg Gln Ala Pro Gly Lys Gly Leu Glu Trp Val
        35                  40                  45

Ser Tyr Ile Trp Pro Ser Gly Gly Asn Thr Tyr Tyr Ala Asp Ser Val
    50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Ser Tyr Asp Leu Trp Ser Tyr Ala Phe Glu Ile Trp Gly Gln
            100                 105                 110

Gly Thr Met Val Thr Val Ser Ser
        115                 120

<210> SEQ ID NO 57
<211> LENGTH: 120
<212> TYPE: PRT
<213> ORGANISM: Homo sapiens

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Met Trp Trp Val Arg Gln Ala Pro Gly Lys Gly Leu Glu Trp Val
        35                  40                  45

Ser Tyr Ile Trp Pro Ser Gly Gly Asn Thr Tyr Tyr Ala Asp Ser Val
    50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Ser Phe Asp Phe Trp Ser Asn Ala Phe Glu Leu Trp Gly Gln
            100                 105                 110

Gly Thr Met Val Thr Val Ser Ser
        115                 120

<210> SEQ ID NO 58
<211> LENGTH: 639
<212> TYPE: DNA
<213> ORGANISM: Homo sapiens

<400> SEQUENCE: 58
```

```
gacatccaga tgacccagtc tccatcctcc ctgtctgcat ctgtaggaga cagagtcacc    60
atcacttgcc gggcaagtca gagcattggc agctacttaa actggtatca gcagaaacca   120
gggaaagccc ctaaggccct gatctatgct gcatccagtt tgcaaagtgg ggtcccatca   180
aggttcagtg gcagtgggtc tgggacagat ttcactctca ccatcagtag tctgcaacct   240
gaagattttg caacttacta ctgtcaacag agttacagta ccccctcgtt cggccaaggg   300
accaaggtgg aaatcaaaag aactgtggct gcaccatctg tcttcatctt cccgccatct   360
gatgagcagt tgaaatctgg aactgcctct gttgtgtgcc tgctgaataa cttctatccc   420
agagaggcca aagtacagtg gaaggtggat aacgccctcc aatcgggtaa ctcccaggag   480
agtgtcacag agcaggacag caaggacagc acctacagcc tcagcagcac cctgacgctg   540
agcaaagcag actacgagaa acacaaagtc tacgcctgcg aagtcaccca tcagggcctg   600
agctcgcccg tcacaaagag cttcaacagg ggagagtgt                         639

<210> SEQ ID NO 59
<211> LENGTH: 1344
<212> TYPE: DNA
<213> ORGANISM: Homo sapiens

<400> SEQUENCE: 59
gaagttcaat tgttagagtc tggtggcggt cttgttcagc ctggtggttc tttacgtctt    60
tcttgcgctg cttccggatt cactttctct cgttacgtta tgtggtgggt tcgccaagct   120
cctggtaaag gtttggagtg gtttcttat atctggcctt ctggtggcaa tacttattat   180
gctgactccg ttaaaggtcg cttcactatc tctagagaca actctaagaa tactctctac   240
ttgcagatga acagcttaag ggctgaggac actgcagtct actattgtgc gagtagctac   300
gattttggga gtaatgcttt tgatatctgg ggccaaggga caatggtcac cgtctcaagc   360
gcctccacca agggcccatc ggtcttcccg ctagcgccct gctccaggag cacctccgag   420
agcacagccg ccctgggctg cctggtcaag gactacttcc ccgaaccggt gacggtgtcg   480
tggaactcag gcgccctgac cagcggcgtc cacaccttcc cggctgtcct acagtcctcc   540
ggactctact ccctcagcag cgtagtgacc gtgccctcca gcagcttggg cacgaagacc   600
tacacctgca acgtagatca caagcccagc aacaccaagg tggacaagag agttgagtcc   660
aaatatggtc ccccatgccc atcatgccca gcacctgagt tcctgggggg accatcagtc   720
ttcctgttcc ccccaaaacc caaggacact ctcatgatct cccggacccc tgaggtcacg   780
tgcgtggtgg tggacgtgag ccaggaagac cccgaggtcc agttcaactg gtacgtggat   840
ggcgtggagg tgcataatgc caagacaaag ccgcgggagg agcagttcaa cagcacgtac   900
cgtgtggtca gcgtcctcac cgtcctgcac caggactggc tgaacggcaa ggagtacaag   960
tgcaaggtct ccaacaaagg cctcccgtcc tccatcgaga aaaccatctc caaagccaaa  1020
gggcagcccc gagagccaca ggtgtacacc ctgcccccat cccaggagga gatgaccaag  1080
aaccaggtca gcctgacctg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggcta accgtggaca gagcaggtg gcaggagggg  1260 aatgtcttct catgctccgt gatgcatgag gctctgcaca accactacac acagaagagc  1320
ctctccctgt ctctgggtaa atga                                        1344

<210> SEQ ID NO 60
<211> LENGTH: 213
<212> TYPE: PRT
```

<213> ORGANISM: Homo sapiens

<400> SEQUENCE: 60

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Tyr
            20                  25                  30

Leu Asn Trp Tyr Gln Gln Lys Pro Gly Lys Ala Pro Lys Ala Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ser
                85                  90                  95

Phe Gly Gln Gly Thr Lys Val Glu Ile Lys Arg Thr Val Ala Ala Pro
            100                 105                 110

Ser Val Phe Leu Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 61
<211> LENGTH: 446
<212> TYPE: PRT
<213> ORGANISM: Homo sapiens

<400> SEQUENCE: 61

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Met Trp Trp Val Arg Gln Ala Pro Gly Lys Gly Leu Glu Trp Val
        35                  40                  45

Ser Tyr Ile Trp Pro Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Ser Tyr Asp Phe Trp Ser Asn Ala Phe Asp Ile Trp Gly Gln
            100                 105                 110

Gly Thr Asn Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140
```

-continued

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445
```